United States Patent
Hedhammar et al.

(10) Patent No.: US 9,856,308 B2
(45) Date of Patent: *Jan. 2, 2018

(54) SPIDER SILK FUSION PROTEIN STRUCTURES INCORPORATING IMMUNOGLOBULIN FRAGMENTS AS AFFINITY LIGANDS

(71) Applicant: SPIBER TECHNOLOGIES AB, Stockholm (SE)

(72) Inventors: My Hedhammar, Stockholm (SE); Jan Johansson, Stockholm (SE); Anna Rising, Uppsala (SE); Per Åke Nygren, Ekerö (SE)

(73) Assignee: SPIBER TECHNOLOGIES AB, Stockholm (SE)

( * ) Notice: Subject to any disclaimer, the term of this patent is extended or adjusted under 35 U.S.C. 154(b) by 295 days.

This patent is subject to a terminal disclaimer.

(21) Appl. No.: 14/398,361

(22) PCT Filed: May 2, 2013

(86) PCT No.: PCT/EP2013/059145
§ 371 (c)(1),
(2) Date: Oct. 31, 2014

(87) PCT Pub. No.: WO2013/164404
PCT Pub. Date: Nov. 7, 2013

(65) Prior Publication Data
US 2015/0119554 A1     Apr. 30, 2015

(30) Foreign Application Priority Data

May 2, 2012     (EP) .................................. 12166392.6

(51) Int. Cl.
   *C07K 14/78*     (2006.01)
   *C07K 14/43*     (2006.01)
   *C07K 16/00*     (2006.01)
   *C07K 16/44*     (2006.01)
   *C07K 14/435*    (2006.01)

(52) U.S. Cl.
   CPC ........ *C07K 14/78* (2013.01); *C07K 14/43518* (2013.01); *C07K 16/00* (2013.01); *C07K 16/44* (2013.01); *C07K 2317/35* (2013.01); *C07K 2317/56* (2013.01); *C07K 2317/569* (2013.01); *C07K 2317/622* (2013.01); *C07K 2319/00* (2013.01); *C07K 2319/30* (2013.01); *C07K 2319/70* (2013.01)

(58) Field of Classification Search
   None
   See application file for complete search history.

(56) References Cited

U.S. PATENT DOCUMENTS

2005/0261479 A1     11/2005     Hoffmann et al.

FOREIGN PATENT DOCUMENTS

| WO | WO 2005/111068 A2 | 11/2005 |
| WO | WO 2007/078239 A2 | 7/2007 |
| WO | WO 2010/097385 A1 | 9/2010 |
| WO | WO 2012/055854 A1 | 5/2012 |

OTHER PUBLICATIONS

U.S. Appl. No. 13/880,628, filed Aug. 6, 2013.
U.S. Appl. No. 14/398,370, filed Oct. 31, 2014.
Hedhammar et al., "Structural Properties of Recombinant Nonrepetitive and Repetitive Parts of Major Ampullate Spidroin 1 from Euprosthenops australis: Implications for Fiber Formation", Biochemistry, American Chemical Society, vol. 47, No. 11, Mar. 1, 2008, pp. 3407-3417.
International Search Report, issued in PCT/EP2013/059145, dated Jul. 31, 2013.
Morgan et al., "Characterization and optimization of RGD-containing silk blends to support osteoblastic differentiation", Biomaterials, vol. 29, No. 16, Mar. 5, 2008, pp. 2556-2563.
Rising et al., "Spider silk proteins: recent advances in recombinant production, structure-function relationships and biomedical applications", Cellular and Molecular Life Sciences, vol. 68, No. 2, Jul. 29, 2010, pp. 169-184.
Written Opinion of the International Searching Authority, issued in PCT/EP2013/059145, dated Jul. 31, 2013.
Russian Office Action, dated Oct. 29, 2015, for Russian Application No. 2013123270, along with an English translation.

Primary Examiner — Suzanne M Noakes
Assistant Examiner — Jae W Lee
(74) Attorney, Agent, or Firm — Birch, Stewart, Kolasch & Birch, LLP

(57) ABSTRACT

A recombinant fusion protein comprising the moieties B and CT, and optionally REP, wherein B is comprising at least one immunoglobulin fragment, which provides the capacity of selective interaction with an organic target; CT is a moiety of from 70 to 120 amino acid residues and is derived from the C-terminal fragment of a spider silk protein; and REP is a moiety of from 70 to 300 amino acid residues and is derived from the repetitive fragment of a spider silk protein.

21 Claims, 6 Drawing Sheets

| SEQ ID NO | | |
|---|---|---|
| 14 | CThyb_Esp | SRLSSPEASS RVSSAVSNLV SSG-PTNSAA LSSTISNVVS QIGASNPGLS |
| 15 | CTnat_Eau | SRLSSPSAVS RVSSAVSSLV SNG-QVNMAA LPNIISNISS SVSASAPGAS |
| 16 | AF350266_At1 | SRLSSPGAAS RVSSAVTSLV SSGGPTNSAA LSNTISNVVS QISSSNPGLS |
| 17 | AY666062_Cm1 | SHLSSPEASS RVSSAVSNLV SSG-STNSAA LPNTISNVVS QISSSNPGLS |
| 18 | AF350273_Lg1 | SALAAPATSA RISSHASTLL SNG-PTNPAS ISNVISNAVS QISSSNPGAS |
| 19 | AY953074_Lh1 | SALSAPATSA RISSHASALL SSG-PTNPAS ISNVISNAVS QISSSNPGAS |
| 20 | AY666068_Mh1 | SHLSSPEASS RVSSAVSNLV SGG-STNSAA LPNTISNVVS QISSSNPGLS |
| 21 | U20329_Nc1 | SRLSSPQASS RVSSAVSNLV ASG-PTNSAA LSSTISNVVS QIGASNPGLS |
| 22 | AY666076_Np1 | SRLSSPEASS RVSSAVSNLV SSG-PTNSAA LSNTISNVVS QISSSNPGLS |
| 23 | AF350277_Nm1 | SRLSSPQASS RVSSAVSNLV ASG-PTNSAA LSSTISNAVS QIGASNPGLS |
| 24 | AF350279_Ns1 | SRLSSPEASS RVSSAVSNLV SSG-PTNSAA LSSTISNVVS QIGASNPGLS |
| 25 | AY666057_Ov1 | SRLSSPEASS RVSSAVSNLV SSG-PTNSAA LSNTISNVVS QISSSNPGLS |
| 26 | AY666064_Ps1 | SRLSSPEASS RVSSAVSNLV SSG-PTNSAA LPNTISNVVS QISSSNPGLS |
| 27 | AF350285_Tk1 | SLLSSPASNA RISSAVSALA SGA-ASGPGY LSSVISNVVS QVSSNSGGLV |
| 28 | AF350286_Tv1 | SRLSSPASNA RISSAVSALA SGG-ASSPGY LSSIISNVVS QVSSNDGLS |
| 29 | ABU20328_Ab2 | SRLSSSAASS RVSSAVSSLV SSG-PTTPAA LSNTISSAVS QISASNPGLS |
| 30 | AY365016_Aam2 | -RLSSPQASS RVSSAVSTLV SSG-PTNPAS LSNAIGSVVS QVSASNPGLP |
| 31 | AF350263_Aau2 | SRLSSPQASS RVSSAVSTLV SSG-PTNPAA LSNAISSVVS QVSASNPGLS |
| 32 | AF350267_At2 | SRLSSPQASS RVSSAVSTLV SSG-PTNPAS LSNAISSVVS QVSSSNPGLS |
| 33 | AF350272_Gm2 | SRLSSPQAGA RVSSAVSALV ASG-PTSPAA VSSAISNVAS QISASNPGLS |
| 34 | AF350275_Lg2 | SALSSPTTHA RISSHASTLL SSG-PTNSAA ISNVISNAVS QVSASNPGSS |
| 35 | AY953075_Lh2 | SALSSPTTHA RISSHASTLL SSG-PTNAAA LSNVISNAVS QVSASNPGSS |
| 36 | AY654293_Nc2 | SRLASPDSGA RVASAVSNLV SSG-PTSSAA LSSVISNAVS QIGASNPGLS |
| 37 | AF350278_Nm2 | SRLASPDSGA RVASAVSNLV SSG-PTSSAA LSSVISNAVS QIGASNPGLS |
| 38 | AF350280_Ns2 | SRLASPDSGA RVASAVSNLV SSG-PTSSAA LSSVIXNAVS QIGASNPGLS |
| 39 | AF350269_DtFb1 | SRLSSPEAAS RVSSAVSSLV SNG-QVNVDA LPSIISNLSS SISASATTAS |
| 40 | AF350270_DtFb2 | SRLSSPQAAS RVSSAVSSLV SNG-QVNVAA LPSIISSLSS SISASSTAAS |
| 41 | U47853_ADF1 | NRLSSAGAAS RVSSNVAAIA SAG----AAA LPNVISNIYS GVLSS--GVS |
| 42 | U47854_ADF2 | SRLSSPSAAA RVSSAVS-LV SNGGPTSPAA LSSSISNVVS QISASNPGLS |
| 43 | U47855_ADF3 | SRLSSPAASS RVSSAVSSLV SSG-PTKHAA LSNTISSVVS QVSASNPGLS |
| 44 | U47856_ADF4 | SVYLRLQPRL EVSSAVSSLV SSG-PTNGAA VSGALNSLVS QISASNPGLS |
| 9 | Consensus | SRLSSPQASS RVSSAVSNLV SSG-PTNSAA LSNTISNVVS QISASNPGLS |

Fig 1

| SEQ ID NO | | |
|---|---|---|
| 14 | CThyb_Esp | GCDVLVQALL EVVSALIHIL GSSSIGQVNY GSAGQATQLV GQSVYQALGE F |
| 15 | CTnat_Eau | GCEVIVQALL EVITALVQIV SSSSVGYINP SAVNQITNVV ANAMAQVMG- - |
| 16 | AF350266_At1 | GCDVLVQALL EIVSALVHIL GSANIGQVNS SGVGRSASIV GQSINQAFS- - |
| 17 | AY666062_Cm1 | GCDVLVQALL EVVSALIHIL GSSSIGQVNY GSAGQATQIV ---------- - |
| 18 | AF350273_Lg1 | SCDVLVQALL ELVTALLTII GSSNVGNVNY DSSGQYAQVV SQSVQNAFV- - |
| 19 | AY953074_Lh1 | ACDVLVQALL ELVTALLTII GSSNIGSVNY DSSGQYAQVV TQSVQNVFG- - |
| 20 | AY666068_Mh1 | GCDVLVQALL EVVSALIHIL GSSSIGQVDY GSAGQATQIV GQSA------ - |
| 21 | U20329_Nc1 | GCDVLIQALL EVVSALIQIL GSSSIGQVNY GSAGQATQIV GQSVYQALG- - |
| 22 | AY666076_Np1 | GCDVLVQALL EVVSALIHIL GSSSIGQVNY GSAGQATQIV ---------- - |
| 23 | AF350277_Nm1 | GCDVLIQALL EVVSALIHIL GSSSIGQVNY GSAGQATQ-- ---------- - |
| 24 | AF350279_Ns1 | GCDVLIQALL EVVSALVHIL GSSSIGQVNY GSAGQATQ-- ---------- - |
| 25 | AY666057_Ov1 | GCDVLVQALL EVVSAPIHIL GSSSIGQVNY GSAGQATQIV ---------- - |
| 26 | AY666064_Ps1 | GCDVLVQALL EVVSALIHIL GSSSIGQVNY GSAGQATQIV ---------- - |
| 27 | AF350285_Tk1 | GCDTLVQALL EAAAALVHVL ASSSGGQVNL NTAGYTSQL- ---------- - |
| 28 | AF350286_Tv1 | GCDTVVQALL EVAAALVHVL ASSNIGQVNL NTAGYTSQL- ---------- - |
| 29 | ABU20328_Ab2 | GCDVLVQALL EVVSALVHIL GSSSVGQINY GASAQYAQMV ---------- - |
| 30 | AY365016_Aam2 | SCDVLVQALL EIVSALVHIL GSSSIGQINY SASSQYARLV GQSIAQALG- - |
| 31 | AF350263_Aau2 | GCDVLVQALL ELVSALVHIL GSSSIGQINY AAS------- ---------- - |
| 32 | AF350267_At2 | GCDVLVQALL EIVSALVHIL GSSSIGQINY AASSQYAQLV GQSLTQALG- - |
| 33 | AF350272_Gm2 | GCDVLVQALL EIVSALVSIL SSASIGQINY GASGQYAAMI ---------- - |
| 34 | AF350275_Lg2 | SCDVLVQALL ELITALISIV DSSNIGQVNY GSSGQYAQMV G--------- - |
| 35 | AY953075_Lh2 | SCDVLVQALL EIITALISIL DSSSVGQVNY GSSGQYAQIV GQSMQQAMG- - |
| 36 | AY654293_Nc2 | GCDVLIQALL EIVSACVTIL SSSSIGQVNY GAASQFAQVV GQSVLSAF-- - |
| 37 | AF350278_Nm2 | GCDVLIQALL EIVSACVTIL SSSSIGQVNY GAA------- ---------- - |
| 38 | AF350280_Ns2 | GCDVLIXALL EIVSACVTIL SSSSIGQVNY GAA------- ---------- - |
| 39 | AF350269_DtFb1 | DCEVLVQVLL EVVSALVQIV CS-------- ---------- ---------- - |
| 40 | AF350270_DtFb2 | DCEVLVQVLL EIVSALVQIV SSANVGYINP EASGSLN-AV GSALAAAMG- - |
| 41 | U47853_ADF1 | SSEALIQALL EVISALIHVL GSASIGNVSS VGVNSALNAV QNAVGAYAG- - |
| 42 | U47854_ADF2 | GCDILVQALL EIISALVHIL GSANIGPVNS SSAGQSASIV GQSVYRALS- - |
| 43 | U47855_ADF3 | GCDVLVQALL EVVSALVSIL GSSSIGQINY GASAQYTQMV GQSVAQALA- - |
| 44 | U47856_ADF4 | GCDALVQALL ELVSALVAIL SSASIGQVNV SSVSQSTQMI SQALS----- - |
| 9 | Consensus | GCDVLVQALL EVVSALVHIL GSSSIGQVNY GSAGQATQIV GQSVAQALGE F |

Fig 1 (continued)

```
SEQ
ID NO
  45  Ea MaSp1     SHTTPWTNPGLAENFMNSFMQGLSSMPGFTASQLDDMSTIAQSMVQSIQSLAAQGRTSPNKLQALNMAFA
  46  Lg MaSp1     QANTPWSSKANADAFINSFISSAQNTGSFSQDQMDDMSLIGNTLMTAMDNMG--GRITPSKLQALDMAFA
  47  Lh MaSp1     QANTPWSSKANADAFINSFISAASNTGSFSQDQMEDMSLIGNTLMAAMDNMG--GRITPSKLQALDMAFA
  48  Nc MaSp1     -QNTPWSSTELADAFINAFMNEAGRTGAFTADQLDDMSTIGDTIKTAMDKMARSNKSSKGKLQALNMAFA
  49  At MaSp2     QGATPWENSQLAESFISRFLRFIGQSGAFSPNQLDDMSSIGDTLKTAIEKMAQSRKSSKSKLQALNMAFA
  50  Lg MaSp2     ---LRWSSKDNADRFINAFLQAASNSGAFSSDQVDDMSVIGNTLMTAMDNMG--GRITPSKLQALDMAFA
  51  Lh MaSp2     QANTPWSSKENADAFIGAFMNAASQSGAFSSDQIDDMSVISNTLMAAMDNMG--GRITQSKLQALDMAFA
  52  Nim MaSp2    QANTPWSDTATADAFIQNFLGAVSGSGAFTPDQLDDMSTVGDTIMSAMDKMARSNKSSKSKLQALNMAFA
  53  Nc MaSp2     QARSPWSDTATADAFIQNFLAAVSGSGAFTSDQLDDMSTIGDTIMSAMDKMARSNKSSQHKLQALNMAFA
  54  Ab CySp1     AVPSVFSSPNLASGFLQCLTFGIGNSPAFPTQEQQLDLAIAQVILNAVSSNTGATASAR--AQALSTALA
  55  Ncl CySp1    PVPSVFSSPSLASGFLGCLTTGIGLSPAFPFQEQQLDDLAKVILSAVTSNTDTSKSAR--AQALSTALA
  56  Lh TuSp1     ASVNIFNSPNAATSFLNCLRSNIESSPAFFSNIVSSGEFGAQGAEDFDDIIQSLIQAQ-SMGKGRHDTKAKAKAMQVALA
  57  Nc flag      IANSPFSNPNTAEAFARSFVSNIVSSGEFGAQGAEDFDDIIQSLIQAQ-SMGKGRHDTKAKAKAMQVALA
  58  Nlm flag     IVNSPFSNPNTAEAFARSFVSNVVSSGEFGAQGAEDFDDIIQSLIQAQ-SMGKGRHDTKAKAKAMQVALA 45  Ea MaSp1     SSMAEIAASEEGGGSLSTKTSSIASAMSNAFLQTTGVVNQPFINEITQLVSMFAQAGMNDV
  46  Lg MaSp1     SSVAEIAASEG--GDLGVTTNAIADALTSAFYQTTGVVNNRFISEIRSLISMFAQASANDV
  47  Lh MaSp1     SSVAEIAASEG--GDLGVTTNAIADALTSAFYQTTGVVNSRFISEIRSLIGMFAQASANDV
  48  Nc MaSp1     SSMAEIAAVEQGGLSVDAKTNAIADSLNSAFYQTTGAANPQFVNEIRSLINMFAQSSANEV
  49  At MaSp2     SSMAEIAVAEQGGLSIEAKTNAIASALSAAFLETTGYVNQQFVNEIKTLIFMIAQASSNEI
  50  Lg MaSp2     SSVAEIAVADG--QNVGGATNAISNALRSAFYQTTGVVNNQFISEISNLINMFAQVSANEV
  51  Lh MaSp2     SSVAEIAVADG--QNVGGATNAISDALRSAFYQTTGVVNNQFITGISSLIGMFAQVSGNEV
  52  Nim MaSp2    SSMAEIAAVEQGGQSMDVKTNAIANALDSAFYMTTGSTNQQFVNEMRSLINMLSAAAVNEV
  53  Nc MaSp2     SSMAEIAAVEQGGMSMAVKTNAIVDGLNSAFYMTTGAANPQFVNEMRSLISMISAASANEV
  54  Ab CySp1     SSLTDLLIAESAESNYSNQLSELTGILSDCFIQTTGSDNPAFVSRIQSLISVLSQNADTNI
  55  Ncl CySp1    SSLADLLISESSGSSYQTQISALTNILSDCFVTTTGSNNPAFVSRVQTLIGVLSQSSSNAI
  56  Lh TuSp1     SSIAELLVTESAEEDIDNQVALSTILSQCFVETTGSPNPAFVASVKSLLGVLSQSASNYE
  57  Nc flag      SSIAELVIAESSGGDVQRKTNVISNALRNALMSTTGSPNEEFVHEVQDLIQMLSQEQINEV
  58  Nlm flag     SSIAELVIAESSGGDVQRKTNVISNALRNALMSTTGSPNEEFVHEVQDLIQMLSQEQINEV
```

Fig 2

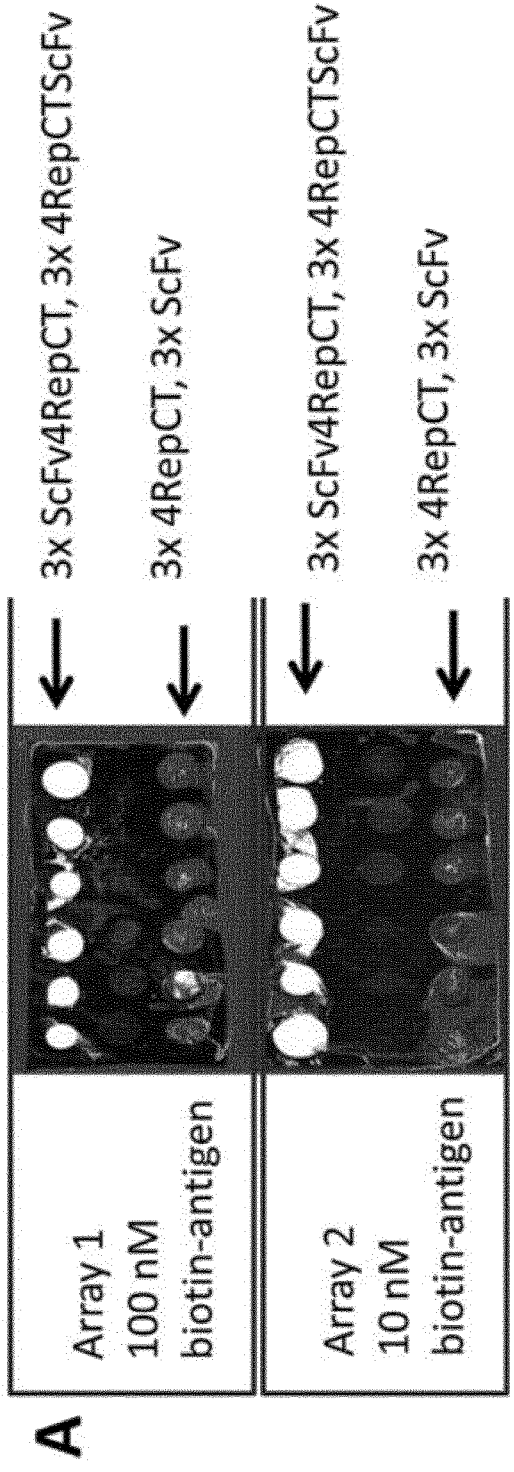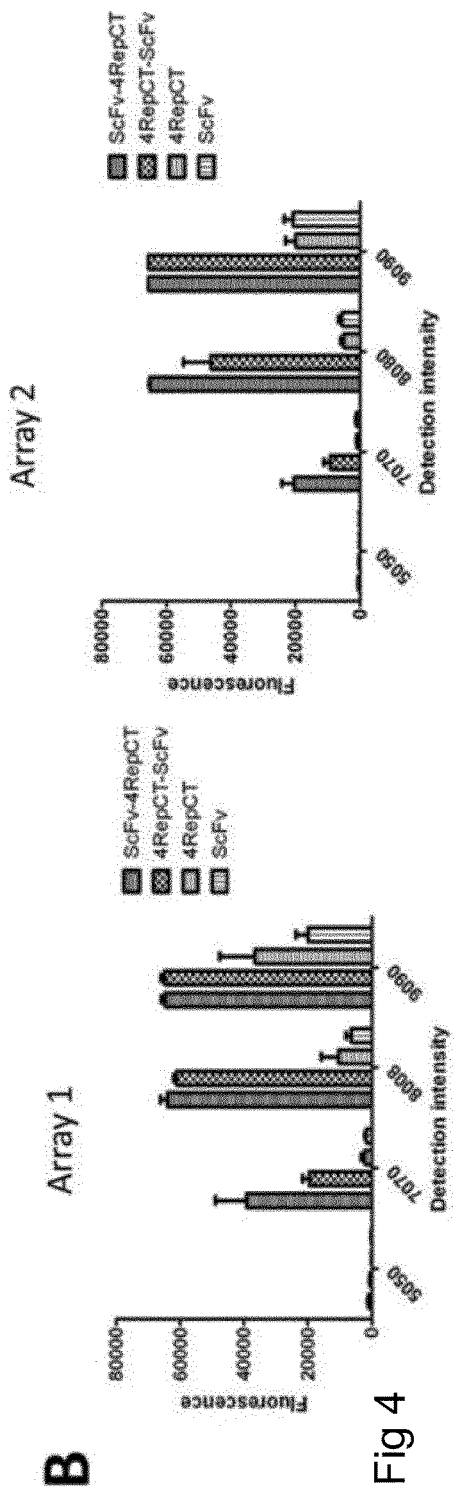
Fig 4

SEQUENCE LISTING

<160> NUMBER OF SEQ ID NOS: 74

<210> SEQ ID NO 1
<211> LENGTH: 149
<212> TYPE: PRT
<213> ORGANISM: Euprosthenops australis

<400> SEQUENCE: 1

Gly Ser Gly Asn Ser Gly Ile Gln Gly Gln Gly Gly Tyr Gly Gly Leu
1               5                   10                  15

Gly Gln Gly Gly Tyr Gly Gln Gly Ala Gly Ser Ser Ala Ala Ala Ala
            20                  25                  30

Ala Ala Ala Ala Ala Ala Ala Gly Gly Gln Gly Gly Gln Gly Gln
        35                  40                  45

Gly Tyr Gly Gln Gly Ser Gly Ser Ala Ala Ala Ala Ala
    50                  55                  60

Ala Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala Ala
                85                  90                  95

Ala Ala Ala Ala Gly Gln Gly Gly Gln Gly Gly Tyr Gly Arg Gln
            100                 105                 110

Ser Gln Gly Ala Gly Ser Ala Ala Ala Ala Ala Ala Ala Ala Ala
            115                 120                 125

Ala Ala Ala Ala Gly Ser Gly Gln Gly Gly Tyr Gly Gln Gly Gln Gly
            130                 135                 140

Gly Tyr Gly Gln Ser
145

<210> SEQ ID NO 2
<211> LENGTH: 265
<212> TYPE: PRT
<213> ORGANISM: Euprosthenops australis
<220> FEATURE:
<221> NAME/KEY: DOMAIN
<222> LOCATION: (1)..(167)
<223> OTHER INFORMATION: REP fragment
<220> FEATURE:
<221> NAME/KEY: DOMAIN
<222> LOCATION: (168)..(265)
<223> OTHER INFORMATION: CT fragment

<400> SEQUENCE: 2

Gly Ser Gly Asn Ser Gly Ile Gln Gly Gln Gly Gly Tyr Gly Gly Leu
1               5                   10                  15

Gly Gln Gly Gly Tyr Gly Gln Gly Ala Gly Ser Ser Ala Ala Ala Ala
            20                  25                  30

Ala Ala Ala Ala Ala Ala Ala Gly Gly Gln Gly Gly Gln Gly Gln
        35                  40                  45

Gly Tyr Gly Gln Gly Ser Gly Ser Ala Ala Ala Ala Ala
    50                  55                  60

Ala Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala Ala
                85                  90                  95

Ala Ala Ala Ala Gly Gln Gly Gly Gln Gly Gly Tyr Gly Arg Gln
            100                 105                 110

Ser Gln Gly Ala Gly Ser Ala Ala Ala Ala Ala Ala Ala Ala Ala
            115                 120                 125

```
Ala Ala Ala Ala Gly Ser Gly Gln Gly Gly Tyr Gly Gln Gly
    130             135             140

Gly Tyr Gly Gln Ser Ser Ala Ser Ala Ser Ala Ala Ser Ala Ala
145             150             155             160

Ser Thr Val Ala Asn Ser Val Ser Arg Leu Ser Ser Pro Ser Ala Val
            165             170             175

Ser Arg Val Ser Ser Ala Val Ser Ser Leu Val Ser Asn Gly Gln Val
        180             185             190

Asn Met Ala Ala Leu Pro Asn Ile Ile Ser Asn Ile Ser Ser Ser Val
        195             200             205

Ser Ala Ser Ala Pro Gly Ala Ser Gly Cys Glu Val Ile Val Gln Ala
        210             215             220

Leu Leu Glu Val Ile Thr Ala Leu Val Gln Ile Val Ser Ser Ser Ser
225             230             235             240

Val Gly Tyr Ile Asn Pro Ser Ala Val Asn Gln Ile Thr Asn Val Val
            245             250             255

Ala Asn Ala Met Ala Gln Val Met Gly
        260             265

<210> SEQ ID NO 3
<211> LENGTH: 296
<212> TYPE: PRT
<213> ORGANISM: Euprosthenops australis
<220> FEATURE:
<221> NAME/KEY: DOMAIN
<222> LOCATION: (1)..(137)
<223> OTHER INFORMATION: NT fragment
<220> FEATURE:
<221> NAME/KEY: DOMAIN
<222> LOCATION: (138)..(296)
<223> OTHER INFORMATION: REP fragment

<400> SEQUENCE: 3

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
    50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
        115                 120                 125

Gln Ala Gly Met Asn Asp Val Ser Ala Ser Ala Ser Ala Gly Ala Ser
    130                 135                 140

Ala Ala Ala Ser Ala Gly Ala Ser Gly Gln Gly Gly Tyr Gly Gly
145                 150                 155                 160

Leu Gly Gln Gly Gly Tyr Gly Gln Gly Ala Gly Ser Ser Ala Ala Ala
                165                 170                 175

Ala Ala Ala Ala Ala Ala Ala Ala Gly Gly Gln Gly Gly Gln Gly
            180                 185                 190
```

-continued

Gln Gly Gly Tyr Gly Gln Gly Ser Gly Gly Ser Ala Ala Ala Ala
        195                 200                 205

Ala Ala Ala Ala Ala Ala Ala Ala Ala Gly Arg Gly Gln Gly Gly
    210                 215                 220

Tyr Gly Gln Gly Ser Gly Gly Asn Ala Ala Ala Ala Ala Ala Ala
225                 230                 235                 240

Ala Ala Ala Ala Ala Ala Gly Gln Gly Gly Gln Gly Gly Tyr Gly
            245                 250                 255

Arg Gln Ser Gln Gly Ala Gly Ser Ala Ala Ala Ala Ala Ala Ala
            260                 265                 270

Ala Ala Ala Ala Ala Gly Ser Gly Gln Gly Gly Tyr Gly Gly Gln
        275                 280                 285

Gly Gln Gly Gly Tyr Gly Gln Ser
        290                 295

<210> SEQ ID NO 4
<211> LENGTH: 340
<212> TYPE: PRT
<213> ORGANISM: Euprosthenops australis
<220> FEATURE:
<221> NAME/KEY: DOMAIN
<222> LOCATION: (1)..(137)
<223> OTHER INFORMATION: NT fragment
<220> FEATURE:
<221> NAME/KEY: DOMAIN
<222> LOCATION: (138)..(340)
<223> OTHER INFORMATION: REP fragment

<400> SEQUENCE: 4

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
    50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
        115                 120                 125

Gln Ala Gly Met Asn Asp Val Ser Ala Ser Ala Gly Ala Ser
    130                 135                 140

Ala Ala Ser Ala Gly Ala Pro Gly Tyr Ser Pro Ala Pro Ser Tyr
145                 150                 155                 160

Ser Ser Gly Gly Tyr Ala Ser Ser Ala Ala Ser Ala Ala Ala Ala
                165                 170                 175

Gly Gln Gly Gly Pro Gly Tyr Gly Pro Ala Pro Asn Gln Gly Ala
            180                 185                 190

Ser Ser Ala Ala Ala Ala Ala Ala Gly Ser Gly Gln Gly Pro Ser Gly
        195                 200                 205

Pro Tyr Gly Thr Ser Tyr Gln Ile Ser Thr Gln Tyr Thr Gln Thr Thr
    210                 215                 220

-continued

```
Thr Ser Gln Gly Gln Gly Tyr Gly Ser Ser Ala Gly Ala Ala
225                 230                 235                 240

Ala Gly Ala Ala Gly Ala Gly Gln Gly Gly Tyr Gly Gln Gly Gln
            245                 250                 255

Gly Gly Tyr Gly Gln Gly Ala Gly Ala Ala Ala Ala Ala
        260                 265                 270

Ala Ala Ala Ala Ala Ala Gly Gln Gly Gly Gln Gly Gly
    275                 280                 285

Gly Tyr Gly Gln Gly Gly Gln Gly Gln Gly Gln Gly Gln Gly
        290                 295                 300

Gly Tyr Gly Gln Gly Ala Gly Ser Ser Ala Ala Ala Ala Ala Ala
305                 310                 315                 320

Ala Ala Ala Ala Ala Ala Gly Arg Gly Gln Gly Gly Tyr Gly Pro
            325                 330                 335

Gly Ser Gly Gly
            340

<210> SEQ ID NO 5
<211> LENGTH: 424
<212> TYPE: PRT
<213> ORGANISM: Euprosthenops australis
<220> FEATURE:
<221> NAME/KEY: DOMAIN
<222> LOCATION: (1)..(136)
<223> OTHER INFORMATION: NT fragment
<220> FEATURE:
<221> NAME/KEY: DOMAIN
<222> LOCATION: (137)..(313)
<223> OTHER INFORMATION: REP fragment
<220> FEATURE:
<221> NAME/KEY: DOMAIN
<222> LOCATION: (314)..(411)
<223> OTHER INFORMATION: CT fragment
<220> FEATURE:
<221> NAME/KEY: DOMAIN
<222> LOCATION: (412)..(424)
<223> OTHER INFORMATION: His tag

<400> SEQUENCE: 5

Met Lys Ala Ser His Thr Thr Pro Trp Thr Asn Pro Gly Leu Ala Glu
1               5                   10                  15

Asn Phe Met Asn Ser Phe Met Gln Gly Leu Ser Ser Met Pro Gly Phe
            20                  25                  30

Thr Ala Ser Gln Leu Asp Asp Met Ser Thr Ile Ala Gln Ser Met Val
        35                  40                  45

Gln Ser Ile Gln Ser Leu Ala Ala Gln Gly Arg Thr Ser Pro Asn Lys
    50                  55                  60

Leu Gln Ala Leu Asn Met Ala Phe Ala Ser Ser Met Ala Glu Ile Ala
65                  70                  75                  80

Ala Ser Glu Glu Gly Gly Gly Ser Leu Ser Thr Lys Thr Ser Ser Ile
                85                  90                  95

Ala Ser Ala Met Ser Asn Ala Phe Leu Gln Thr Thr Gly Val Val Asn
            100                 105                 110

Gln Pro Phe Ile Asn Glu Ile Thr Gln Leu Val Ser Met Phe Ala Gln
        115                 120                 125

Ala Gly Met Asn Asp Val Ser Ala Ser Ala Gly Ala Ser Ala
    130                 135                 140

Ala Ala Ser Ala Gly Ala Ala Ser Gly Gln Gly Gly Tyr Gly Gly Leu
145                 150                 155                 160
```

```
Gly Gln Gly Gly Tyr Gly Gln Gly Ala Gly Ser Ser Ala Ala Ala
                165                 170                 175
Ala Ala Ala Ala Ala Ala Ala Gly Gly Gln Gly Gly Gln Gly Gln
            180                 185                 190
Gly Gly Tyr Gly Gln Gly Ser Gly Ser Ala Ala Ala Ala Ala
        195                 200                 205
Ala Ala Ala Ala Ala Ala Ala Gly Arg Gly Gln Gly Gly Tyr
    210                 215                 220
Gly Gln Gly Ser Gly Asn Ala Ala Ala Ala Ala Ala Ala Ala
225                 230                 235                 240
Ala Ala Ala Ala Ala Gly Gln Gly Gln Gly Gly Tyr Gly Arg
                245                 250                 255
Gln Ser Gln Gly Ala Gly Ser Ala Ala Ala Ala Ala Ala Ala
                260                 265                 270
Ala Ala Ala Ala Ala Gly Ser Gly Gln Gly Tyr Gly Gln Gly
        275                 280                 285
Gln Gly Gly Tyr Gly Gln Ser Ser Ala Ser Ala Ser Ala Ala Ser
            290                 295                 300
Ala Ala Ser Thr Val Ala Asn Ser Val Ser Arg Leu Ser Ser Pro Ser
305                 310                 315                 320
Ala Val Ser Arg Val Ser Ser Ala Val Ser Ser Leu Val Ser Asn Gly
                325                 330                 335
Gln Val Asn Met Ala Ala Leu Pro Asn Ile Ile Ser Asn Ile Ser Ser
                340                 345                 350
Ser Val Ser Ala Ser Ala Pro Gly Ala Ser Gly Cys Glu Val Ile Val
            355                 360                 365
Gln Ala Leu Leu Glu Val Ile Thr Ala Leu Val Gln Ile Val Ser Ser
    370                 375                 380
Ser Ser Val Gly Tyr Ile Asn Pro Ser Ala Val Asn Gln Ile Thr Asn
385                 390                 395                 400
Val Val Ala Asn Ala Met Ala Gln Val Met Gly Lys Leu Ala Ala Ala
                405                 410                 415
Leu Glu His His His His His His
            420

<210> SEQ ID NO 6
<211> LENGTH: 137
<212> TYPE: PRT
<213> ORGANISM: Euprosthenops australis
<220> FEATURE:
<221> NAME/KEY: VARIANT
<222> LOCATION: (6)..(6)
<223> OTHER INFORMATION: deletion (deltaHis)

<400> SEQUENCE: 6

Gly Ser Gly Asn Ser His Thr Thr Pro Trp Thr Asn Pro Gly Leu Ala
1               5                   10                  15
Glu Asn Phe Met Asn Ser Phe Met Gln Gly Leu Ser Ser Met Pro Gly
                20                  25                  30
Phe Thr Ala Ser Gln Leu Asp Asp Met Ser Thr Ile Ala Gln Ser Met
            35                  40                  45
Val Gln Ser Ile Gln Ser Leu Ala Ala Gln Gly Arg Thr Ser Pro Asn
        50                  55                  60
Lys Leu Gln Ala Leu Asn Met Ala Phe Ala Ser Ser Met Ala Glu Ile
65                  70                  75                  80
Ala Ala Ser Glu Glu Gly Gly Gly Ser Leu Ser Thr Lys Thr Ser Ser
```

```
                        85                  90                  95

Ile Ala Ser Ala Met Ser Asn Ala Phe Leu Gln Thr Thr Gly Val Val
                100                 105                 110

Asn Gln Pro Phe Ile Asn Glu Ile Thr Gln Leu Val Ser Met Phe Ala
        115                 120                 125

Gln Ala Gly Met Asn Asp Val Ser Ala
        130                 135

<210> SEQ ID NO 7
<211> LENGTH: 98
<212> TYPE: PRT
<213> ORGANISM: Euprosthenops australis

<400> SEQUENCE: 7

Ser Arg Leu Ser Ser Pro Ser Ala Val Ser Arg Val Ser Ser Ala Val
1               5                   10                  15

Ser Ser Leu Val Ser Asn Gly Gln Val Asn Met Ala Ala Leu Pro Asn
            20                  25                  30

Ile Ile Ser Asn Ile Ser Ser Val Ser Ala Ser Ala Pro Gly Ala
        35                  40                  45

Ser Gly Cys Glu Val Ile Val Gln Ala Leu Leu Glu Val Ile Thr Ala
    50                  55                  60

Leu Val Gln Ile Val Ser Ser Ser Val Gly Tyr Ile Asn Pro Ser
65                  70                  75                  80

Ala Val Asn Gln Ile Thr Asn Val Val Ala Asn Ala Met Ala Gln Val
                85                  90                  95

Met Gly

<210> SEQ ID NO 8
<211> LENGTH: 131
<212> TYPE: PRT
<213> ORGANISM: Artificial Sequence
<220> FEATURE:
<223> OTHER INFORMATION: Consensus sequence derived from spidroin NT
      fragments
<220> FEATURE:
<221> NAME/KEY: VARIANT
<222> LOCATION: (20)..(20)
<223> OTHER INFORMATION: Leu
<220> FEATURE:
<221> NAME/KEY: VARIANT
<222> LOCATION: (42)..(42)
<223> OTHER INFORMATION: Asn
<220> FEATURE:
<221> NAME/KEY: VARIANT
<222> LOCATION: (42)..(42)
<223> OTHER INFORMATION: Gln
<220> FEATURE:
<221> NAME/KEY: VARIANT
<222> LOCATION: (50)..(50)
<223> OTHER INFORMATION: Ser
<220> FEATURE:
<221> NAME/KEY: VARIANT
<222> LOCATION: (50)..(50)
<223> OTHER INFORMATION: Lys
<220> FEATURE:
<221> NAME/KEY: VARIANT
<222> LOCATION: (56)..(56)
<223> OTHER INFORMATION: Arg
<220> FEATURE:
<221> NAME/KEY: VARIANT
<222> LOCATION: (84)..(84)
<223> OTHER INFORMATION: Leu
<220> FEATURE:
<221> NAME/KEY: VARIANT
<222> LOCATION: (114)..(114)
<223> OTHER INFORMATION: Ser
```

```
<220> FEATURE:
<221> NAME/KEY: VARIANT
<222> LOCATION: (121)..(121)
<223> OTHER INFORMATION: Asn
<220> FEATURE:
<221> NAME/KEY: VARIANT
<222> LOCATION: (123)..(123)
<223> OTHER INFORMATION: Leu
<220> FEATURE:
<221> NAME/KEY: VARIANT
<222> LOCATION: (124)..(124)
<223> OTHER INFORMATION: Ser

<400> SEQUENCE: 8

Gln Ala Asn Thr Pro Trp Ser Ser Pro Asn Leu Ala Asp Ala Phe Ile
1               5                   10                  15

Asn Ser Phe Met Ser Ala Ala Ser Ser Ser Gly Ala Phe Ser Ala Asp
            20                  25                  30

Gln Leu Asp Asp Met Ser Thr Ile Gly Asp Thr Leu Met Ser Ala Met
        35                  40                  45

Asp Asn Met Gly Arg Ser Gly Lys Ser Thr Lys Ser Lys Leu Gln Ala
    50                  55                  60

Leu Asn Met Ala Phe Ala Ser Ser Met Ala Glu Ile Ala Ala Ala Glu
65                  70                  75                  80

Ser Gly Gly Gly Ser Val Gly Val Lys Thr Asn Ala Ile Ser Asp Ala
                85                  90                  95

Leu Ser Ser Ala Phe Tyr Gln Thr Thr Gly Ser Val Asn Pro Gln Phe
            100                 105                 110

Val Asn Glu Ile Arg Ser Leu Ile Gly Met Phe Ala Gln Ala Ser Ala
        115                 120                 125

Asn Glu Val
    130

<210> SEQ ID NO 9
<211> LENGTH: 100
<212> TYPE: PRT
<213> ORGANISM: Artificial Sequence
<220> FEATURE:
<223> OTHER INFORMATION: Consensus sequence derived from known MaSp1
      and MaSp2 proteins
<220> FEATURE:
<221> NAME/KEY: MISC_FEATURE
<222> LOCATION: (1)..(71)
<223> OTHER INFORMATION: Sequence length present in known species
      variants
<220> FEATURE:
<221> NAME/KEY: VARIANT
<222> LOCATION: (7)..(7)
<223> OTHER INFORMATION: Glu

<400> SEQUENCE: 9

Ser Arg Leu Ser Ser Pro Gln Ala Ser Ser Arg Val Ser Ser Ala Val
1               5                   10                  15

Ser Asn Leu Val Ser Ser Gly Pro Thr Asn Ser Ala Ala Leu Ser Asn
            20                  25                  30

Thr Ile Ser Asn Val Val Ser Gln Ile Ser Ala Ser Asn Pro Gly Leu
        35                  40                  45

Ser Gly Cys Asp Val Leu Val Gln Ala Leu Leu Glu Val Val Ser Ala
    50                  55                  60

Leu Val His Ile Leu Gly Ser Ser Ser Ile Gly Gln Val Asn Tyr Gly
65                  70                  75                  80

Ser Ala Gly Gln Ala Thr Gln Ile Val Gly Ser Val Ala Gln Ala
                85                  90                  95
```

Leu Gly Glu Phe
        100

<210> SEQ ID NO 10
<211> LENGTH: 1110
<212> TYPE: PRT
<213> ORGANISM: Euprosthenops australis
<220> FEATURE:
<221> NAME/KEY: REPEAT
<222> LOCATION: (7)..(19)
<220> FEATURE:
<221> NAME/KEY: REPEAT
<222> LOCATION: (20)..(42)
<220> FEATURE:
<221> NAME/KEY: REPEAT
<222> LOCATION: (43)..(56)
<220> FEATURE:
<221> NAME/KEY: REPEAT
<222> LOCATION: (57)..(70)
<220> FEATURE:
<221> NAME/KEY: REPEAT
<222> LOCATION: (71)..(83)
<220> FEATURE:
<221> NAME/KEY: REPEAT
<222> LOCATION: (84)..(106)
<220> FEATURE:
<221> NAME/KEY: REPEAT
<222> LOCATION: (107)..(120)
<220> FEATURE:
<221> NAME/KEY: REPEAT
<222> LOCATION: (121)..(134)
<220> FEATURE:
<221> NAME/KEY: REPEAT
<222> LOCATION: (135)..(147)
<220> FEATURE:
<221> NAME/KEY: REPEAT
<222> LOCATION: (148)..(170)
<220> FEATURE:
<221> NAME/KEY: REPEAT
<222> LOCATION: (171)..(183)
<220> FEATURE:
<221> NAME/KEY: REPEAT
<222> LOCATION: (184)..(197)
<220> FEATURE:
<221> NAME/KEY: REPEAT
<222> LOCATION: (198)..(211)
<220> FEATURE:
<221> NAME/KEY: REPEAT
<222> LOCATION: (212)..(234)
<220> FEATURE:
<221> NAME/KEY: REPEAT
<222> LOCATION: (235)..(248)
<220> FEATURE:
<221> NAME/KEY: REPEAT
<222> LOCATION: (249)..(265)
<220> FEATURE:
<221> NAME/KEY: REPEAT
<222> LOCATION: (266)..(279)
<220> FEATURE:
<221> NAME/KEY: REPEAT
<222> LOCATION: (280)..(293)
<220> FEATURE:
<221> NAME/KEY: REPEAT
<222> LOCATION: (294)..(306)
<220> FEATURE:
<221> NAME/KEY: REPEAT
<222> LOCATION: (307)..(329)
<220> FEATURE:
<221> NAME/KEY: REPEAT
<222> LOCATION: (330)..(342)
<220> FEATURE:
<221> NAME/KEY: REPEAT
<222> LOCATION: (343)..(356)
<220> FEATURE:
<221> NAME/KEY: REPEAT
<222> LOCATION: (357)..(370)
<220> FEATURE:

```
-continued

<221> NAME/KEY: REPEAT
<222> LOCATION: (371)..(393)
<220> FEATURE:
<221> NAME/KEY: REPEAT
<222> LOCATION: (394)..(406)
<220> FEATURE:
<221> NAME/KEY: REPEAT
<222> LOCATION: (407)..(420)
<220> FEATURE:
<221> NAME/KEY: REPEAT
<222> LOCATION: (421)..(434)
<220> FEATURE:
<221> NAME/KEY: REPEAT
<222> LOCATION: (435)..(457)
<220> FEATURE:
<221> NAME/KEY: REPEAT
<222> LOCATION: (458)..(470)
<220> FEATURE:
<221> NAME/KEY: REPEAT
<222> LOCATION: (471)..(488)
<220> FEATURE:
<221> NAME/KEY: REPEAT
<222> LOCATION: (489)..(502)
<220> FEATURE:
<221> NAME/KEY: REPEAT
<222> LOCATION: (503)..(516)
<220> FEATURE:
<221> NAME/KEY: REPEAT
<222> LOCATION: (517)..(529)
<220> FEATURE:
<221> NAME/KEY: REPEAT
<222> LOCATION: (530)..(552)
<220> FEATURE:
<221> NAME/KEY: REPEAT
<222> LOCATION: (553)..(566)
<220> FEATURE:
<221> NAME/KEY: REPEAT
<222> LOCATION: (567)..(580)
<220> FEATURE:
<221> NAME/KEY: REPEAT
<222> LOCATION: (581)..(594)
<220> FEATURE:
<221> NAME/KEY: REPEAT
<222> LOCATION: (595)..(617)
<220> FEATURE:
<221> NAME/KEY: REPEAT
<222> LOCATION: (618)..(630)
<220> FEATURE:
<221> NAME/KEY: REPEAT
<222> LOCATION: (631)..(647)
<220> FEATURE:
<221> NAME/KEY: REPEAT
<222> LOCATION: (648)..(661)
<220> FEATURE:
<221> NAME/KEY: REPEAT
<222> LOCATION: (662)..(675)
<220> FEATURE:
<221> NAME/KEY: REPEAT
<222> LOCATION: (676)..(688)
<220> FEATURE:
<221> NAME/KEY: REPEAT
<222> LOCATION: (689)..(711)
<220> FEATURE:
<221> NAME/KEY: REPEAT
<222> LOCATION: (712)..(725)
<220> FEATURE:
<221> NAME/KEY: REPEAT
<222> LOCATION: (726)..(739)
<220> FEATURE:
<221> NAME/KEY: REPEAT
<222> LOCATION: (740)..(752)
<220> FEATURE:
<221> NAME/KEY: REPEAT
<222> LOCATION: (753)..(775)
<220> FEATURE:
<221> NAME/KEY: REPEAT
<222> LOCATION: (776)..(789)
<220> FEATURE:
<221> NAME/KEY: REPEAT
```

```
<222> LOCATION: (790)..(803)
<220> FEATURE:
<221> NAME/KEY: REPEAT
<222> LOCATION: (804)..(816)
<220> FEATURE:
<221> NAME/KEY: REPEAT
<222> LOCATION: (817)..(839)
<220> FEATURE:
<221> NAME/KEY: REPEAT
<222> LOCATION: (840)..(853)
<220> FEATURE:
<221> NAME/KEY: REPEAT
<222> LOCATION: (854)..(867)
<220> FEATURE:
<221> NAME/KEY: REPEAT
<222> LOCATION: (868)..(880)
<220> FEATURE:
<221> NAME/KEY: REPEAT
<222> LOCATION: (881)..(903)
<220> FEATURE:
<221> NAME/KEY: REPEAT
<222> LOCATION: (904)..(917)
<220> FEATURE:
<221> NAME/KEY: REPEAT
<222> LOCATION: (918)..(931)
<220> FEATURE:
<221> NAME/KEY: REPEAT
<222> LOCATION: (932)..(945)
<220> FEATURE:
<221> NAME/KEY: REPEAT
<222> LOCATION: (946)..(968)
<220> FEATURE:
<221> NAME/KEY: REPEAT
<222> LOCATION: (969)..(981)
<220> FEATURE:
<221> NAME/KEY: REPEAT
<222> LOCATION: (982)..(998)
<220> FEATURE:
<221> NAME/KEY: REPEAT
<222> LOCATION: (999)..(1013)
<220> FEATURE:
<221> NAME/KEY: REPEAT
<222> LOCATION: (1014)..(1027)
<220> FEATURE:
<221> NAME/KEY: REPEAT
<222> LOCATION: (1028)..(1042)
<220> FEATURE:
<221> NAME/KEY: REPEAT
<222> LOCATION: (1043)..(1059)
<220> FEATURE:
<221> NAME/KEY: REPEAT
<222> LOCATION: (1060)..(1073)
<220> FEATURE:
<221> NAME/KEY: REPEAT
<222> LOCATION: (1074)..(1092)

<400> SEQUENCE: 10

Gln Gly Ala Gly Gly Asn Ala Ala Ala Ala Ala Ala Ala Ala Ala
 1               5                  10                  15

Ala Ala Ala Gly Gln Gly Gly Gln Gly Gly Tyr Gly Gly Leu Gly Gln
            20                  25                  30

Gly Gly Tyr Gly Gln Gly Ala Gly Ser Ser Ala Ala Ala Ala Ala
         35                  40                  45

Ala Ala Ala Ala Ala Ala Ala Gly Arg Gly Gln Gly Gly Tyr Gly
        50                   55                  60

Gln Gly Ser Gly Gly Asn Ala Ala Ala Ala Ala Ala Ala Ala Ala
65                  70                  75                  80

Ala Ala Ser Gly Gln Gly Gly Gln Gly Gln Gly Gln Gly Gly Gln
                85                  90                  95

Gly Gly Tyr Gly Gln Gly Ala Gly Ser Ser Ala Ala Ala Ala Ala
            100                 105                 110
```

```
Ala Ala Ala Ala Ala Ala Ala Gly Gln Gly Gln Gly Arg Tyr Gly
            115                 120                 125
Gln Gly Ala Gly Gly Asn Ala Ala Ala Ala Ala Ala Ala Ala Ala
        130                 135                 140
Ala Ala Ala Gly Gln Gly Gly Gln Gly Gly Gln Gly Gly Leu Gly Gln
145                 150                 155                 160
Gly Gly Tyr Gly Gln Gly Ala Gly Ser Ser Ala Ala Ala Ala Ala
            165                 170                 175
Ser Ala Ala Ala Ala Ala Ala Gly Arg Gly Gln Gly Gly Tyr Gly Gln
        180                 185                 190
Gly Ala Gly Gly Asn Ala Ala Ala Ala Ala Ala Ala Ala Ala Ala
            195                 200                 205
Ala Ala Ala Gly Gln Gly Gly Gln Gly Gly Tyr Gly Gly Leu Gly Gln
        210                 215                 220
Gly Gly Tyr Gly Gln Gly Ala Gly Ser Ser Ala Ala Ala Ala Ala
225                 230                 235                 240
Ala Ala Ala Ala Ala Ala Ala Gly Gly Gln Gly Gly Gln Gly Gln Gly
            245                 250                 255
Arg Tyr Gly Gln Gly Ala Gly Ser Ser Ala Ala Ala Ala Ala Ala
        260                 265                 270
Ala Ala Ala Ala Ala Ala Ala Gly Gln Gly Gln Gly Gly Tyr Gly Gln
        275                 280                 285
Gly Ala Gly Gly Asn Ala Ala Ala Ala Ala Ala Ala Ala Ala Ala
            290                 295                 300
Ala Ala Gly Gln Gly Gly Gln Gly Gly Gln Gly Gly Leu Gly Gln Gly
305                 310                 315                 320
Gly Tyr Gly Gln Gly Ala Gly Ser Ser Ala Ala Ala Ala Ala Ala
            325                 330                 335
Ala Ala Ala Ala Ala Ala Gly Arg Gly Gln Gly Gly Tyr Gly Gln Gly
        340                 345                 350
Ala Gly Gly Asn Ala Ala Ala Ala Ala Ala Ala Ala Glu Ala Ala
            355                 360                 365
Ala Ala Gly Gln Gly Gly Gln Gly Gly Tyr Gly Gly Leu Gly Gln Gly
        370                 375                 380
Gly Tyr Gly Gln Gly Ala Gly Ser Ser Ala Ala Ala Ala Ala Ala
385                 390                 395                 400
Ala Ala Ala Ala Ala Ala Gly Arg Gly Gln Gly Gly Tyr Gly Gln Gly
            405                 410                 415
Ala Gly Gly Asn Ala Ala Ala Ala Ala Ala Ala Ala Ala Ala Ala
        420                 425                 430
Ala Ala Gly Gln Gly Gly Gln Gly Gly Tyr Gly Gly Leu Gly Gln Gly
        435                 440                 445
Gly Tyr Gly Gln Gly Ala Gly Ser Ser Ala Ala Ala Ala Ala Ala
    450                 455                 460
Ala Ala Ala Ala Ala Ala Gly Gly Gln Gly Gly Gln Gly Gln Gly Arg
465                 470                 475                 480
Tyr Gly Gln Gly Ala Gly Ser Ser Ala Ala Ala Ala Ala Ala Ala
            485                 490                 495
Ala Ala Ala Ala Ala Ala Gly Arg Gly Gln Gly Gly Tyr Gly Gln Gly
        500                 505                 510
Ser Gly Gly Asn Ala Ala Ala Ala Ala Ala Ala Ala Ala Ala Ala
        515                 520                 525
Ser Gly Gln Gly Ser Gln Gly Gly Gln Gly Gly Gln Gly Gln Gly Gly
```

```
                530             535             540
Tyr Gly Gln Gly Ala Gly Ser Ser Ala Ala Ala Ala Ala Ala Ala Ala
545                 550             555                 560

Ala Ala Ala Ala Ala Ser Gly Arg Gly Gln Gly Gly Tyr Gly Gln Gly
                565             570                 575

Ala Gly Gly Asn Ala Ala Ala Ala Ala Ala Ala Ala Ala Ala Ala Ala
                580             585                 590

Ala Ala Gly Gln Gly Gly Gln Gly Gly Tyr Gly Gly Leu Gly Gln Gly
            595             600             605

Gly Tyr Gly Gln Gly Ala Gly Ser Ser Ala Ala Ala Ala Ala Ala Ala
    610             615             620

Ala Ala Ala Ala Ala Gly Gly Gln Gly Gly Gln Gly Gly Gln Gly Gly Tyr
625                 630             635             640

Gly Gln Gly Ala Gly Ser Ser Ala Ala Ala Ala Ala Ala Ala Ala
            645             650                 655

Ala Ala Ala Ala Ala Gly Arg Gly Gln Gly Gly Tyr Gly Gln Gly Ser
                660             665             670

Gly Gly Asn Ala Ala Ala Ala Ala Ala Ala Ala Ala Ala Ala Ala Ser
    675             680                 685

Gly Gln Gly Gly Gln Gly Gly Gln Gly Gly Gln Gly Gly Gly Gly Tyr
    690             695             700

Gly Gln Gly Ala Gly Ser Ser Ala Ala Ala Ala Ala Ala Ala Ala
705             710             715                 720

Ala Ala Ala Ala Ala Gly Gln Gly Gln Gly Gly Tyr Gly Gln Gly Ala
                725             730             735

Gly Gly Asn Ala Ala Ala Ala Ala Ala Ala Ala Ala Ala Ala Ala Ala
    740             745             750

Gly Gln Gly Gly Gln Gly Gly Gln Gly Gly Leu Gly Gln Gly Gly Tyr
            755             760             765

Gly Gln Gly Ala Gly Ser Ser Ala Ala Ala Ala Ala Ala Ala Ala
    770             775             780

Ala Ala Ala Ala Ala Gly Arg Gly Gln Gly Gly Tyr Gly Gln Gly Val
785                 790             795                 800

Gly Gly Asn Ala Ala Ala Ala Ala Ala Ala Ala Ala Ala Ala Ala Ala
    805             810                 815

Gly Gln Gly Gly Gln Gly Gly Gln Gly Gly Leu Gly Gln Gly Gly Tyr
            820             825             830

Gly Gln Gly Ala Gly Ser Ser Ala Ala Ala Ala Ala Ala Ala Ala
    835             840             845

Ala Ala Ala Ala Ala Gly Arg Gly Gln Gly Gly Tyr Gly Gln Gly Ser
850                 855             860

Gly Gly Asn Ala Ala Ala Ala Ala Ala Ala Ala Ala Ala Ala Ala Ser
865                 870             875                 880

Gly Gln Gly Ser Gln Gly Gly Gln Gly Gly Gln Gly Gly Gly Gly Tyr
            885             890             895

Gly Gln Gly Ala Gly Ser Ser Ala Ala Ala Ala Ala Ala Ala Ala
    900             905             910

Ala Ala Ala Ala Ser Gly Arg Gly Gln Gly Gly Tyr Gly Gln Gly Ala
            915             920             925

Gly Gly Asn Ala Ala Ala Ala Ala Ala Ala Ala Ala Ala Ala Ala
    930             935             940

Ala Gly Gln Gly Gly Gln Gly Gly Tyr Gly Gly Leu Gly Gln Gly Gly
945             950             955             960
```

-continued

```
Tyr Gly Gln Gly Ala Gly Ser Ser Ala Ala Ala Ala Ala Ala Ala
                965                 970                 975

Ala Ala Ala Ala Gly Gly Gln Gly Gly Gln Gly Gly Gly Tyr Gly
            980                 985                 990

Gln Gly Ser Gly Gly Ser Ala Ala Ala Ala Ala Ala Ala Ala Ala
        995                 1000                1005

Ala Ala Ala Ala Ala Gly Arg Gly Gln Gly Gly Tyr Gly Gln Gly
    1010                1015                1020

Ser Gly Gly Asn Ala Ala Ala Ala Ala Ala Ala Ala Ala Ala Ala
    1025                1030                1035

Ala Ala Ala Ala Gly Gln Gly Gly Gln Gly Gly Tyr Gly Arg Gln
    1040                1045                1050

Ser Gln Gly Ala Gly Ser Ala Ala Ala Ala Ala Ala Ala Ala Ala
    1055                1060                1065

Ala Ala Ala Ala Ala Gly Ser Gly Gln Gly Gly Tyr Gly Gly Gln
    1070                1075                1080

Gly Gln Gly Gly Tyr Gly Gln Ser Ser Ala Ser Ala Ser Ala Ala
    1085                1090                1095

Ala Ser Ala Ala Ser Thr Val Ala Asn Ser Val Ser
    1100                1105                1110

<210> SEQ ID NO 11
<211> LENGTH: 23
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (4)..(4)
<223> OTHER INFORMATION: Ser
<220> FEATURE:
<221> NAME/KEY: VARIANT
<222> LOCATION: (8)..(8)
<223> OTHER INFORMATION: Tyr
<220> FEATURE:
<221> NAME/KEY: VARIANT
<222> LOCATION: (11)..(11)
<223> OTHER INFORMATION: Gln

<400> SEQUENCE: 11

Gly Gln Gly Gly Gln Gly Gly Gln Gly Gly Leu Gly Gln Gly Gly Tyr
1               5                   10                  15

Gly Gln Gly Ala Gly Ser Ser
            20

<210> SEQ ID NO 12
<211> LENGTH: 17
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (9)..(9)
<223> OTHER INFORMATION: Arg
<220> FEATURE:
<221> NAME/KEY: VARIANT
<222> LOCATION: (14)..(14)
<223> OTHER INFORMATION: Ser
<220> FEATURE:
<221> NAME/KEY: VARIANT
<222> LOCATION: (16)..(16)
```

-continued

```
<223> OTHER INFORMATION: Gly

<400> SEQUENCE: 12

Gly Gln Gly Gly Gln Gly Gln Gly Gly Tyr Gly Gln Gly Ala Gly Ser
1               5                   10                  15

Ser

<210> SEQ ID NO 13
<211> LENGTH: 14
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (2)..(2)
<223> OTHER INFORMATION: Gln
<220> FEATURE:
<221> NAME/KEY: VARIANT
<222> LOCATION: (6)..(6)
<223> OTHER INFORMATION: Arg
<220> FEATURE:
<221> NAME/KEY: VARIANT
<222> LOCATION: (11)..(11)
<223> OTHER INFORMATION: Ser
<220> FEATURE:
<221> NAME/KEY: VARIANT
<222> LOCATION: (11)..(11)
<223> OTHER INFORMATION: Val

<400> SEQUENCE: 13

Gly Arg Gly Gln Gly Gly Tyr Gly Gln Gly Ala Gly Gly Asn
1               5                   10

<210> SEQ ID NO 14
<211> LENGTH: 100
<212> TYPE: PRT
<213> ORGANISM: Euprosthenops sp

<400> SEQUENCE: 14

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Ser
                20                  25                  30

Thr Ile Ser Asn Val Val Ser Gln Ile Gly Ala Ser Asn Pro Gly Leu
            35                  40                  45

Ser Gly Cys Asp Val Leu Val Gln Ala Leu Leu Glu Val Val Ser Ala
        50                  55                  60

Leu Ile His Ile Leu Gly Ser Ser Ser Ile Gly Gln Val Asn Tyr Gly
65                  70                  75                  80

Ser Ala Gly Gln Ala Thr Gln Leu Val Gly Gln Ser Val Tyr Gln Ala
                85                  90                  95

Leu Gly Glu Phe
            100

<210> SEQ ID NO 15
<211> LENGTH: 98
<212> TYPE: PRT
<213> ORGANISM: Euprosthenops australis

<400> SEQUENCE: 15

Ser Arg Leu Ser Ser Pro Ser Ala Val Ser Arg Val Ser Ser Ala Val
1               5                   10                  15
```

```
Ser Ser Leu Val Ser Asn Gly Gln Val Asn Met Ala Ala Leu Pro Asn
            20                  25                  30

Ile Ile Ser Asn Ile Ser Ser Val Ser Ala Ser Pro Gly Ala
            35                  40                  45

Ser Gly Cys Glu Val Ile Val Gln Ala Leu Leu Glu Val Ile Thr Ala
 50                  55                  60

Leu Val Gln Ile Val Ser Ser Ser Val Gly Tyr Ile Asn Pro Ser
 65                  70                  75                  80

Ala Val Asn Gln Ile Thr Asn Val Val Ala Asn Ala Met Ala Gln Val
                 85                  90                  95

Met Gly

<210> SEQ ID NO 16
<211> LENGTH: 99
<212> TYPE: PRT
<213> ORGANISM: Argiope trifasciata

<400> SEQUENCE: 16

Ser Arg Leu Ser Ser Pro Gly Ala Ala Ser Arg Val Ser Ser Ala Val
 1               5                  10                  15

Thr Ser Leu Val Ser Ser Gly Gly Pro Thr Asn Ser Ala Ala Leu Ser
            20                  25                  30

Asn Thr Ile Ser Asn Val Val Ser Gln Ile Ser Ser Ser Asn Pro Gly
            35                  40                  45

Leu Ser Gly Cys Asp Val Leu Val Gln Ala Leu Leu Glu Ile Val Ser
 50                  55                  60

Ala Leu Val His Ile Leu Gly Ser Ala Asn Ile Gly Gln Val Asn Ser
 65                  70                  75                  80

Ser Gly Val Gly Arg Ser Ala Ser Ile Val Gly Gln Ser Ile Asn Gln
                 85                  90                  95

Ala Phe Ser

<210> SEQ ID NO 17
<211> LENGTH: 89
<212> TYPE: PRT
<213> ORGANISM: Cyrtophora moluccensis

<400> SEQUENCE: 17

Ser His Leu Ser Ser Pro Glu Ala Ser Ser Arg Val Ser Ala Val
 1               5                  10                  15

Ser Asn Leu Val Ser Ser Gly Ser Thr Asn Ser Ala Ala Leu Pro Asn
            20                  25                  30

Thr Ile Ser Asn Val Val Ser Gln Ile Ser Ser Ser Asn Pro Gly Leu
            35                  40                  45

Ser Gly Cys Asp Val Leu Val Gln Ala Leu Leu Glu Val Val Ser Ala
 50                  55                  60

Leu Ile His Ile Leu Gly Ser Ser Ser Ile Gly Gln Val Asn Tyr Gly
 65                  70                  75                  80

Ser Ala Gly Gln Ala Thr Gln Ile Val
                 85

<210> SEQ ID NO 18
<211> LENGTH: 98
<212> TYPE: PRT
<213> ORGANISM: Latrodectus geometricus

<400> SEQUENCE: 18
```

```
Ser Ala Leu Ala Ala Pro Ala Thr Ser Ala Arg Ile Ser Ser His Ala
1               5                   10                  15

Ser Thr Leu Leu Ser Asn Gly Pro Thr Asn Pro Ala Ser Ile Ser Asn
                20                  25                  30

Val Ile Ser Asn Ala Val Ser Gln Ile Ser Ser Asn Pro Gly Ala
            35                  40                  45

Ser Ser Cys Asp Val Leu Val Gln Ala Leu Leu Glu Leu Val Thr Ala
    50                  55                  60

Leu Leu Thr Ile Ile Gly Ser Ser Asn Val Gly Asn Val Asn Tyr Asp
65                  70                  75                  80

Ser Ser Gly Gln Tyr Ala Gln Val Val Ser Gln Ser Val Gln Asn Ala
                85                  90                  95

Phe Val
```

<210> SEQ ID NO 19
<211> LENGTH: 98
<212> TYPE: PRT
<213> ORGANISM: Latrodectus hesperus

<400> SEQUENCE: 19

```
Ser Ala Leu Ser Ala Pro Ala Thr Ser Ala Arg Ile Ser Ser His Ala
1               5                   10                  15

Ser Ala Leu Leu Ser Ser Gly Pro Thr Asn Pro Ala Ser Ile Ser Asn
                20                  25                  30

Val Ile Ser Asn Ala Val Ser Gln Ile Ser Ser Asn Pro Gly Ala
            35                  40                  45

Ser Ala Cys Asp Val Leu Val Gln Ala Leu Leu Glu Leu Val Thr Ala
    50                  55                  60

Leu Leu Thr Ile Ile Gly Ser Ser Asn Ile Gly Ser Val Asn Tyr Asp
65                  70                  75                  80

Ser Ser Gly Gln Tyr Ala Gln Val Val Thr Gln Ser Val Gln Asn Val
                85                  90                  95

Phe Gly
```

<210> SEQ ID NO 20
<211> LENGTH: 93
<212> TYPE: PRT
<213> ORGANISM: Macrothele holsti

<400> SEQUENCE: 20

```
Ser His Leu Ser Ser Pro Glu Ala Ser Ser Arg Val Ser Ser Ala Val
1               5                   10                  15

Ser Asn Leu Val Ser Gly Gly Ser Thr Asn Ser Ala Ala Leu Pro Asn
                20                  25                  30

Thr Ile Ser Asn Val Val Ser Gln Ile Ser Ser Ser Asn Pro Gly Leu
            35                  40                  45

Ser Gly Cys Asp Val Leu Val Gln Ala Leu Leu Glu Val Val Ser Ala
    50                  55                  60

Leu Ile His Ile Leu Gly Ser Ser Ser Ile Gly Gln Val Asp Tyr Gly
65                  70                  75                  80

Ser Ala Gly Gln Ala Thr Gln Ile Val Gly Gln Ser Ala
                85                  90
```

<210> SEQ ID NO 21
<211> LENGTH: 98
<212> TYPE: PRT
<213> ORGANISM: Nephila clavipes

<400> SEQUENCE: 21

Ser Arg Leu Ser Ser Pro Gln Ala Ser Ser Arg Val Ser Ala Val
1               5                   10                  15

Ser Asn Leu Val Ala Ser Gly Pro Thr Asn Ser Ala Ala Leu Ser Ser
            20                  25                  30

Thr Ile Ser Asn Val Val Ser Gln Ile Gly Ala Ser Asn Pro Gly Leu
        35                  40                  45

Ser Gly Cys Asp Val Leu Ile Gln Ala Leu Leu Glu Val Val Ser Ala
    50                  55                  60

Leu Ile Gln Ile Leu Gly Ser Ser Ile Gly Gln Val Asn Tyr Gly
65                  70                  75                  80

Ser Ala Gly Gln Ala Thr Gln Ile Val Gly Gln Ser Val Tyr Gln Ala
                85                  90                  95

Leu Gly

<210> SEQ ID NO 22
<211> LENGTH: 89
<212> TYPE: PRT
<213> ORGANISM: Nephila pilipes

<400> SEQUENCE: 22

Ser Arg Leu Ser Ser Pro Glu Ala Ser Ser Arg Val Ser Ala Val
1               5                   10                  15

Ser Asn Leu Val Ser Ser Gly Pro Thr Asn Ser Ala Ala Leu Ser Asn
            20                  25                  30

Thr Ile Ser Asn Val Val Ser Gln Ile Ser Ser Ser Asn Pro Gly Leu
        35                  40                  45

Ser Gly Cys Asp Val Leu Val Gln Ala Leu Leu Glu Val Val Ser Ala
    50                  55                  60

Leu Ile His Ile Leu Gly Ser Ser Ile Gly Gln Val Asn Tyr Gly
65                  70                  75                  80

Ser Ala Gly Gln Ala Thr Gln Ile Val
                85

<210> SEQ ID NO 23
<211> LENGTH: 87
<212> TYPE: PRT
<213> ORGANISM: Nephila madagascariensis

<400> SEQUENCE: 23

Ser Arg Leu Ser Ser Pro Gln Ala Ser Ser Arg Val Ser Ala Val
1               5                   10                  15

Ser Asn Leu Val Ala Ser Gly Pro Thr Asn Ser Ala Ala Leu Ser Ser
            20                  25                  30

Thr Ile Ser Asn Ala Val Ser Gln Ile Gly Ala Ser Asn Pro Gly Leu
        35                  40                  45

Ser Gly Cys Asp Val Leu Ile Gln Ala Leu Leu Glu Val Val Ser Ala
    50                  55                  60

Leu Ile His Ile Leu Gly Ser Ser Ile Gly Gln Val Asn Tyr Gly
65                  70                  75                  80

Ser Ala Gly Gln Ala Thr Gln
                85

<210> SEQ ID NO 24
<211> LENGTH: 87
<212> TYPE: PRT

<213> ORGANISM: Nephila senegalensis

<400> SEQUENCE: 24

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Ser
                20                  25                  30

Thr Ile Ser Asn Val Val Ser Gln Ile Gly Ala Ser Asn Pro Gly Leu
            35                  40                  45

Ser Gly Cys Asp Val Leu Ile Gln Ala Leu Leu Glu Val Val Ser Ala
        50                  55                  60

Leu Val His Ile Leu Gly Ser Ser Ile Gly Gln Val Asn Tyr Gly
65                  70                  75                  80

Ser Ala Gly Gln Ala Thr Gln
                85

<210> SEQ ID NO 25
<211> LENGTH: 89
<212> TYPE: PRT
<213> ORGANISM: Octonoba varians

<400> SEQUENCE: 25

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Asn
                20                  25                  30

Thr Ile Ser Asn Val Val Ser Gln Ile Ser Ser Asn Pro Gly Leu
            35                  40                  45

Ser Gly Cys Asp Val Leu Val Gln Ala Leu Leu Glu Val Val Ser Ala
        50                  55                  60

Pro Ile His Ile Leu Gly Ser Ser Ile Gly Gln Val Asn Tyr Gly
65                  70                  75                  80

Ser Ala Gly Gln Ala Thr Gln Ile Val
                85

<210> SEQ ID NO 26
<211> LENGTH: 89
<212> TYPE: PRT
<213> ORGANISM: Psechrus sinensis

<400> SEQUENCE: 26

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Pro Asn
                20                  25                  30

Thr Ile Ser Asn Val Val Ser Gln Ile Ser Ser Ser Asn Pro Gly Leu
            35                  40                  45

Ser Gly Cys Asp Val Leu Val Gln Ala Leu Leu Glu Val Val Ser Ala
        50                  55                  60

Leu Ile His Ile Leu Gly Ser Ser Ile Gly Gln Val Asn Tyr Gly
65                  70                  75                  80

Ser Ala Gly Gln Ala Thr Gln Ile Val
                85

<210> SEQ ID NO 27
<211> LENGTH: 88
<212> TYPE: PRT
<213> ORGANISM: Tetragnatha kauaiensis

```
<400> SEQUENCE: 27

Ser Leu Leu Ser Ser Pro Ala Ser Asn Ala Arg Ile Ser Ser Ala Val
1               5                   10                  15

Ser Ala Leu Ala Ser Gly Ala Ala Ser Gly Pro Gly Tyr Leu Ser Ser
            20                  25                  30

Val Ile Ser Asn Val Val Ser Gln Val Ser Ser Asn Ser Gly Gly Leu
        35                  40                  45

Val Gly Cys Asp Thr Leu Val Gln Ala Leu Leu Glu Ala Ala Ala Ala
    50                  55                  60

Leu Val His Val Leu Ala Ser Ser Ser Gly Gly Gln Val Asn Leu Asn
65                  70                  75                  80

Thr Ala Gly Tyr Thr Ser Gln Leu
                85

<210> SEQ ID NO 28
<211> LENGTH: 88
<212> TYPE: PRT
<213> ORGANISM: Tetragnatha versicolor

<400> SEQUENCE: 28

Ser Arg Leu Ser Ser Pro Ala Ser Asn Ala Arg Ile Ser Ser Ala Val
1               5                   10                  15

Ser Ala Leu Ala Ser Gly Gly Ala Ser Ser Pro Gly Tyr Leu Ser Ser
            20                  25                  30

Ile Ile Ser Asn Val Val Ser Gln Val Ser Ser Asn Asn Asp Gly Leu
        35                  40                  45

Ser Gly Cys Asp Thr Val Val Gln Ala Leu Leu Glu Val Ala Ala Ala
    50                  55                  60

Leu Val His Val Leu Ala Ser Ser Asn Ile Gly Gln Val Asn Leu Asn
65                  70                  75                  80

Thr Ala Gly Tyr Thr Ser Gln Leu
                85

<210> SEQ ID NO 29
<211> LENGTH: 89
<212> TYPE: PRT
<213> ORGANISM: Araneus bicentenarius

<400> SEQUENCE: 29

Ser Arg Leu Ser Ser Ser Ala Ala Ser Ser Arg Val Ser Ser Ala Val
1               5                   10                  15

Ser Ser Leu Val Ser Ser Gly Pro Thr Thr Pro Ala Ala Leu Ser Asn
            20                  25                  30

Thr Ile Ser Ser Ala Val Ser Gln Ile Ser Ala Ser Asn Pro Gly Leu
        35                  40                  45

Ser Gly Cys Asp Val Leu Val Gln Ala Leu Leu Glu Val Val Ser Ala
    50                  55                  60

Leu Val His Ile Leu Gly Ser Ser Ser Val Gly Gln Ile Asn Tyr Gly
65                  70                  75                  80

Ala Ser Ala Gln Tyr Ala Gln Met Val
                85

<210> SEQ ID NO 30
<211> LENGTH: 97
<212> TYPE: PRT
<213> ORGANISM: Argiope amoena
```

-continued

```
<400> SEQUENCE: 30

Arg Leu Ser Ser Pro Gln Ala Ser Ser Arg Val Ser Ser Ala Val Ser
1               5                   10                  15

Thr Leu Val Ser Ser Gly Pro Thr Asn Pro Ala Ser Leu Ser Asn Ala
            20                  25                  30

Ile Gly Ser Val Val Ser Gln Val Ser Ala Ser Asn Pro Gly Leu Pro
        35                  40                  45

Ser Cys Asp Val Leu Val Gln Ala Leu Leu Glu Ile Val Ser Ala Leu
50                  55                  60

Val His Ile Leu Gly Ser Ser Ile Gly Gln Ile Asn Tyr Ser Ala
65                  70                  75                  80

Ser Ser Gln Tyr Ala Arg Leu Val Gly Gln Ser Ile Ala Gln Ala Leu
                85                  90                  95

Gly

<210> SEQ ID NO 31
<211> LENGTH: 82
<212> TYPE: PRT
<213> ORGANISM: Argiope aurantia

<400> SEQUENCE: 31

Ser Arg Leu Ser Ser Pro Gln Ala Ser Ser Arg Val Ser Ser Ala Val
1               5                   10                  15

Ser Thr Leu Val Ser Ser Gly Pro Thr Asn Pro Ala Ala Leu Ser Asn
            20                  25                  30

Ala Ile Ser Ser Val Val Ser Gln Val Ser Ala Ser Asn Pro Gly Leu
        35                  40                  45

Ser Gly Cys Asp Val Leu Val Gln Ala Leu Leu Glu Leu Val Ser Ala
50                  55                  60

Leu Val His Ile Leu Gly Ser Ser Ile Gly Gln Ile Asn Tyr Ala
65                  70                  75                  80

Ala Ser

<210> SEQ ID NO 32
<211> LENGTH: 98
<212> TYPE: PRT
<213> ORGANISM: Argiope trifasciata

<400> SEQUENCE: 32

Ser Arg Leu Ser Ser Pro Gln Ala Ser Ser Arg Val Ser Ser Ala Val
1               5                   10                  15

Ser Thr Leu Val Ser Ser Gly Pro Thr Asn Pro Ala Ser Leu Ser Asn
            20                  25                  30

Ala Ile Ser Ser Val Val Ser Gln Val Ser Ser Asn Pro Gly Leu
        35                  40                  45

Ser Gly Cys Asp Val Leu Val Gln Ala Leu Leu Glu Ile Val Ser Ala
50                  55                  60

Leu Val His Ile Leu Gly Ser Ser Ile Gly Gln Ile Asn Tyr Ala
65                  70                  75                  80

Ala Ser Ser Gln Tyr Ala Gln Leu Val Gly Gln Ser Leu Thr Gln Ala
                85                  90                  95

Leu Gly

<210> SEQ ID NO 33
<211> LENGTH: 89
<212> TYPE: PRT
```

<213> ORGANISM: Gasteracantha mammosa

<400> SEQUENCE: 33

Ser Arg Leu Ser Ser Pro Gln Ala Gly Ala Arg Val Ser Ser Ala Val
1               5                   10                  15

Ser Ala Leu Val Ala Ser Gly Pro Thr Ser Pro Ala Ala Val Ser Ser
            20                  25                  30

Ala Ile Ser Asn Val Ala Ser Gln Ile Ser Ala Ser Asn Pro Gly Leu
        35                  40                  45

Ser Gly Cys Asp Val Leu Val Gln Ala Leu Leu Glu Ile Val Ser Ala
    50                  55                  60

Leu Val Ser Ile Leu Ser Ser Ala Ser Ile Gly Gln Ile Asn Tyr Gly
65                  70                  75                  80

Ala Ser Gly Gln Tyr Ala Ala Met Ile
                85

<210> SEQ ID NO 34
<211> LENGTH: 90
<212> TYPE: PRT
<213> ORGANISM: Latrodectus geometricus

<400> SEQUENCE: 34

Ser Ala Leu Ser Ser Pro Thr Thr His Ala Arg Ile Ser Ser His Ala
1               5                   10                  15

Ser Thr Leu Leu Ser Ser Gly Pro Thr Asn Ser Ala Ala Ile Ser Asn
            20                  25                  30

Val Ile Ser Asn Ala Val Ser Gln Val Ser Ala Ser Asn Pro Gly Ser
        35                  40                  45

Ser Ser Cys Asp Val Leu Val Gln Ala Leu Leu Glu Leu Ile Thr Ala
    50                  55                  60

Leu Ile Ser Ile Val Asp Ser Ser Asn Ile Gly Gln Val Asn Tyr Gly
65                  70                  75                  80

Ser Ser Gly Gln Tyr Ala Gln Met Val Gly
                85                  90

<210> SEQ ID NO 35
<211> LENGTH: 98
<212> TYPE: PRT
<213> ORGANISM: Latrodectus hesperus

<400> SEQUENCE: 35

Ser Ala Leu Ser Ser Pro Thr Thr His Ala Arg Ile Ser Ser His Ala
1               5                   10                  15

Ser Thr Leu Leu Ser Ser Gly Pro Thr Asn Ala Ala Ala Leu Ser Asn
            20                  25                  30

Val Ile Ser Asn Ala Val Ser Gln Val Ser Ala Ser Asn Pro Gly Ser
        35                  40                  45

Ser Ser Cys Asp Val Leu Val Gln Ala Leu Leu Glu Ile Ile Thr Ala
    50                  55                  60

Leu Ile Ser Ile Leu Asp Ser Ser Ser Val Gly Gln Val Asn Tyr Gly
65                  70                  75                  80

Ser Ser Gly Gln Tyr Ala Gln Ile Val Gly Gln Ser Met Gln Gln Ala
                85                  90                  95

Met Gly

<210> SEQ ID NO 36
<211> LENGTH: 97

```
<212> TYPE: PRT
<213> ORGANISM: Nephila clavipes

<400> SEQUENCE: 36

Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
            20                  25                  30

Val Ile Ser Asn Ala Val Ser Gln Ile Gly Ala Ser Asn Pro Gly Leu
        35                  40                  45

Ser Gly Cys Asp Val Leu Ile Gln Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala Ser Gln Phe Ala Gln Val Val Gly Gln Ser Val Leu Ser Ala
                85                  90                  95

Phe

<210> SEQ ID NO 37
<211> LENGTH: 82
<212> TYPE: PRT
<213> ORGANISM: Nephila madagascariensis

<400> SEQUENCE: 37

Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
            20                  25                  30

Val Ile Ser Asn Ala Val Ser Gln Ile Gly Ala Ser Asn Pro Gly Leu
        35                  40                  45

Ser Gly Cys Asp Val Leu Ile Gln Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala

<210> SEQ ID NO 38
<211> LENGTH: 82
<212> TYPE: PRT
<213> ORGANISM: Nephila senegalensis
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid

<400> SEQUENCE: 38

Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
            20                  25                  30

Val Ile Xaa Asn Ala Val Ser Gln Ile Gly Ala Ser Asn Pro Gly Leu
        35                  40                  45

Ser Gly Cys Asp Val Leu Ile Xaa Ala Leu Leu Glu Ile Val Ser Ala
    50                  55                  60

Cys Val Thr Ile Leu Ser Ser Ser Ile Gly Gln Val Asn Tyr Gly
```

```
65                  70                  75                  80

Ala Ala

<210> SEQ ID NO 39
<211> LENGTH: 71
<212> TYPE: PRT
<213> ORGANISM: Dolomedes tenebrosus

<400> SEQUENCE: 39

Ser Arg Leu Ser Ser Pro Glu Ala Ala Ser Arg Val Ser Ser Ala Val
1               5                   10                  15

Ser Ser Leu Val Ser Asn Gly Gln Val Asn Val Asp Ala Leu Pro Ser
            20                  25                  30

Ile Ile Ser Asn Leu Ser Ser Ser Ile Ser Ala Ser Ala Thr Thr Ala
        35                  40                  45

Ser Asp Cys Glu Val Leu Val Gln Val Leu Leu Glu Val Val Ser Ala
    50                  55                  60

Leu Val Gln Ile Val Cys Ser
65                  70

<210> SEQ ID NO 40
<211> LENGTH: 97
<212> TYPE: PRT
<213> ORGANISM: Dolomedes tenebrosus

<400> SEQUENCE: 40

Ser Arg Leu Ser Ser Pro Gln Ala Ala Ser Arg Val Ser Ser Ala Val
1               5                   10                  15

Ser Ser Leu Val Ser Asn Gly Gln Val Asn Val Ala Ala Leu Pro Ser
            20                  25                  30

Ile Ile Ser Ser Leu Ser Ser Ser Ile Ser Ala Ser Ser Thr Ala Ala
        35                  40                  45

Ser Asp Cys Glu Val Leu Val Gln Val Leu Leu Glu Ile Val Ser Ala
    50                  55                  60

Leu Val Gln Ile Val Ser Ser Ala Asn Val Gly Tyr Ile Asn Pro Glu
65                  70                  75                  80

Ala Ser Gly Ser Leu Asn Ala Val Gly Ser Ala Leu Ala Ala Ala Met
                85                  90                  95

Gly

<210> SEQ ID NO 41
<211> LENGTH: 93
<212> TYPE: PRT
<213> ORGANISM: Araneus diadematus

<400> SEQUENCE: 41

Asn Arg Leu Ser Ser Ala Gly Ala Ala Ser Arg Val Ser Ser Asn Val
1               5                   10                  15

Ala Ala Ile Ala Ser Ala Gly Ala Ala Leu Pro Asn Val Ile Ser
            20                  25                  30

Asn Ile Tyr Ser Gly Val Leu Ser Ser Gly Val Ser Ser Ser Glu Ala
        35                  40                  45

Leu Ile Gln Ala Leu Leu Glu Val Ile Ser Ala Leu Ile His Val Leu
    50                  55                  60

Gly Ser Ala Ser Ile Gly Asn Val Ser Ser Val Gly Val Asn Ser Ala
65                  70                  75                  80

Leu Asn Ala Val Gln Asn Ala Val Gly Ala Tyr Ala Gly
```

<210> SEQ ID NO 42
<211> LENGTH: 98
<212> TYPE: PRT
<213> ORGANISM: Araneus diadematus

<400> SEQUENCE: 42

Ser Arg Leu Ser Ser Pro Ser Ala Ala Arg Val Ser Ser Ala Val
1               5                   10                  15

Ser Leu Val Ser Asn Gly Gly Pro Thr Ser Pro Ala Ala Leu Ser Ser
            20                  25                  30

Ser Ile Ser Asn Val Val Ser Gln Ile Ser Ala Ser Asn Pro Gly Leu
        35                  40                  45

Ser Gly Cys Asp Ile Leu Val Gln Ala Leu Leu Glu Ile Ile Ser Ala
    50                  55                  60

Leu Val His Ile Leu Gly Ser Ala Asn Ile Gly Pro Val Asn Ser Ser
65                  70                  75                  80

Ser Ala Gly Gln Ser Ala Ser Ile Val Gly Gln Ser Val Tyr Arg Ala
                85                  90                  95

Leu Ser

<210> SEQ ID NO 43
<211> LENGTH: 98
<212> TYPE: PRT
<213> ORGANISM: Araneus diadematus

<400> SEQUENCE: 43

Ser Arg Leu Ser Ser Pro Ala Ala Ser Ser Arg Val Ser Ser Ala Val
1               5                   10                  15

Ser Ser Leu Val Ser Ser Gly Pro Thr Lys His Ala Ala Leu Ser Asn
            20                  25                  30

Thr Ile Ser Ser Val Val Ser Gln Val Ser Ala Ser Asn Pro Gly Leu
        35                  40                  45

Ser Gly Cys Asp Val Leu Val Gln Ala Leu Leu Glu Val Val Ser Ala
    50                  55                  60

Leu Val Ser Ile Leu Gly Ser Ser Ser Ile Gly Gln Ile Asn Tyr Gly
65                  70                  75                  80

Ala Ser Ala Gln Tyr Thr Gln Met Val Gly Gln Ser Val Ala Gln Ala
                85                  90                  95

Leu Ala

<210> SEQ ID NO 44
<211> LENGTH: 94
<212> TYPE: PRT
<213> ORGANISM: Araneus diadematus

<400> SEQUENCE: 44

Ser Val Tyr Leu Arg Leu Gln Pro Arg Leu Glu Val Ser Ser Ala Val
1               5                   10                  15

Ser Ser Leu Val Ser Ser Gly Pro Thr Asn Gly Ala Ala Val Ser Gly
            20                  25                  30

Ala Leu Asn Ser Leu Val Ser Gln Ile Ser Ala Ser Asn Pro Gly Leu
        35                  40                  45

Ser Gly Cys Asp Ala Leu Val Gln Ala Leu Leu Glu Leu Val Ser Ala
    50                  55                  60

Leu Val Ala Ile Leu Ser Ser Ala Ser Ile Gly Gln Val Asn Val Ser

```
                65                  70                  75                  80
Ser Val Ser Gln Ser Thr Gln Met Ile Ser Gln Ala Leu Ser
                85                  90

<210> SEQ ID NO 45
<211> LENGTH: 131
<212> TYPE: PRT
<213> ORGANISM: Euprosthenops australis

<400> SEQUENCE: 45

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
                20                  25                  30

Gln Leu Asp Asp Met Ser Thr Ile Ala Gln Ser Met Val Gln Ser Ile
            35                  40                  45

Gln Ser Leu Ala Ala Gln Gly Arg Thr Ser Pro Asn Lys Leu Gln Ala
        50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
                85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Val
    130

<210> SEQ ID NO 46
<211> LENGTH: 127
<212> TYPE: PRT
<213> ORGANISM: Latrodectus geometricus

<400> SEQUENCE: 46

Gln Ala Asn Thr Pro Trp Ser Ser Lys Gln Asn Ala Asp Ala Phe Ile
1               5                   10                  15

Ser Ala Phe Met Thr Ala Ala Ser Gln Ser Gly Ala Phe Ser Ser Asp
                20                  25                  30

Gln Ile Asp Asp Met Ser Val Ile Ser Asn Thr Leu Met Ala Ala Met
            35                  40                  45

Asp Asn Met Gly Gly Arg Ile Thr Pro Ser Lys Leu Gln Ala Leu Asp
        50                  55                  60

Met Ala Phe Ala Ser Ser Val Ala Glu Ile Ala Ala Val Glu Gly Gln
65                  70                  75                  80

Asn Ile Gly Val Thr Thr Asn Ala Ile Ser Asp Ala Leu Thr Ser Ala
                85                  90                  95

Phe Tyr Gln Thr Thr Gly Val Val Asn Asn Lys Phe Ile Ser Glu Ile
            100                 105                 110

Arg Ser Leu Ile Asn Met Phe Ala Gln Ala Ser Ala Asn Asp Val
        115                 120                 125

<210> SEQ ID NO 47
<211> LENGTH: 127
<212> TYPE: PRT
<213> ORGANISM: Latrodectus hesperus

<400> SEQUENCE: 47
```

Gln Ala Asn Thr Pro Trp Ser Ser Lys Ala Asn Ala Asp Ala Phe Ile
1               5                   10                  15

Asn Ser Phe Ile Ser Ala Ala Ser Asn Thr Gly Ser Phe Ser Gln Asp
            20                  25                  30

Gln Met Glu Asp Met Ser Leu Ile Gly Asn Thr Leu Met Ala Ala Met
        35                  40                  45

Asp Asn Met Gly Gly Arg Ile Thr Pro Ser Lys Leu Gln Ala Leu Asp
50                  55                  60

Met Ala Phe Ala Ser Ser Val Ala Glu Ile Ala Ala Ser Glu Gly Gly
65                  70                  75                  80

Asp Leu Gly Val Thr Thr Asn Ala Ile Ala Asp Ala Leu Thr Ser Ala
                85                  90                  95

Phe Tyr Gln Thr Thr Gly Val Val Asn Ser Arg Phe Ile Ser Glu Ile
            100                 105                 110

Arg Ser Leu Ile Gly Met Phe Ala Gln Ala Ser Ala Asn Asp Val
        115                 120                 125

<210> SEQ ID NO 48
<211> LENGTH: 130
<212> TYPE: PRT
<213> ORGANISM: Nephila clavipes

<400> SEQUENCE: 48

Gln Asn Thr Pro Trp Ser Ser Thr Glu Leu Ala Asp Ala Phe Ile Asn
1               5                   10                  15

Ala Phe Met Asn Glu Ala Gly Arg Thr Gly Ala Phe Thr Ala Asp Gln
            20                  25                  30

Leu Asp Asp Met Ser Thr Ile Gly Asp Thr Ile Lys Thr Ala Met Asp
        35                  40                  45

Lys Met Ala Arg Ser Asn Lys Ser Lys Gly Lys Leu Gln Ala Leu
50                  55                  60

Asn Met Ala Phe Ala Ser Ser Met Ala Glu Ile Ala Ala Val Glu Gln
65                  70                  75                  80

Gly Gly Leu Ser Val Asp Ala Lys Thr Asn Ala Ile Ala Asp Ser Leu
                85                  90                  95

Asn Ser Ala Phe Tyr Gln Thr Thr Gly Ala Ala Asn Pro Gln Phe Val
            100                 105                 110

Asn Glu Ile Arg Ser Leu Ile Asn Met Phe Ala Gln Ser Ser Ala Asn
        115                 120                 125

Glu Val
130

<210> SEQ ID NO 49
<211> LENGTH: 131
<212> TYPE: PRT
<213> ORGANISM: Argiope trifasciata

<400> SEQUENCE: 49

Gln Gly Ala Thr Pro Trp Glu Asn Ser Gln Leu Ala Glu Ser Phe Ile
1               5                   10                  15

Ser Arg Phe Leu Arg Phe Ile Gly Gln Ser Gly Ala Phe Ser Pro Asn
            20                  25                  30

Gln Leu Asp Asp Met Ser Ser Ile Gly Asp Thr Leu Lys Thr Ala Ile
        35                  40                  45

Glu Lys Met Ala Gln Ser Arg Lys Ser Ser Lys Ser Lys Leu Gln Ala
50                  55                  60

Leu Asn Met Ala Phe Ala Ser Ser Met Ala Glu Ile Ala Val Ala Glu
65                  70                  75                  80

Gln Gly Gly Leu Ser Leu Glu Ala Lys Thr Asn Ala Ile Ala Ser Ala
                85                  90                  95

Leu Ser Ala Ala Phe Leu Glu Thr Thr Gly Tyr Val Asn Gln Gln Phe
            100                 105                 110

Val Asn Glu Ile Lys Thr Leu Ile Phe Met Ile Ala Gln Ala Ser Ser
        115                 120                 125

Asn Glu Ile
    130

<210> SEQ ID NO 50
<211> LENGTH: 124
<212> TYPE: PRT
<213> ORGANISM: Latrodectus geometricus

<400> SEQUENCE: 50

Leu Arg Trp Ser Ser Lys Asp Asn Ala Asp Arg Phe Ile Asn Ala Phe
1               5                   10                  15

Leu Gln Ala Ala Ser Asn Ser Gly Ala Phe Ser Ser Asp Gln Val Asp
            20                  25                  30

Asp Met Ser Val Ile Gly Asn Thr Leu Met Thr Ala Met Asp Asn Met
        35                  40                  45

Gly Gly Arg Ile Thr Pro Ser Lys Leu Gln Ala Leu Asp Met Ala Phe
    50                  55                  60

Ala Ser Ser Val Ala Glu Ile Ala Val Ala Asp Gly Gln Asn Val Gly
65                  70                  75                  80

Gly Ala Thr Asn Ala Ile Ser Asn Ala Leu Arg Ser Ala Phe Tyr Gln
                85                  90                  95

Thr Thr Gly Val Val Asn Asn Gln Phe Ile Ser Glu Ile Ser Asn Leu
            100                 105                 110

Ile Asn Met Phe Ala Gln Val Ser Ala Asn Glu Val
        115                 120

<210> SEQ ID NO 51
<211> LENGTH: 127
<212> TYPE: PRT
<213> ORGANISM: Latrodectus hesperus

<400> SEQUENCE: 51

Gln Ala Asn Thr Pro Trp Ser Ser Lys Glu Asn Ala Asp Ala Phe Ile
1               5                   10                  15

Gly Ala Phe Met Asn Ala Ala Ser Gln Ser Gly Ala Phe Ser Ser Asp
            20                  25                  30

Gln Ile Asp Asp Met Ser Val Ile Ser Asn Thr Leu Met Ala Ala Met
        35                  40                  45

Asp Asn Met Gly Gly Arg Ile Thr Gln Ser Lys Leu Gln Ala Leu Asp
    50                  55                  60

Met Ala Phe Ala Ser Ser Val Ala Glu Ile Ala Val Ala Asp Gly Gln
65                  70                  75                  80

Asn Val Gly Ala Ala Thr Asn Ala Ile Ser Asp Ala Leu Arg Ser Ala
                85                  90                  95

Phe Tyr Gln Thr Thr Gly Val Val Asn Asn Gln Phe Ile Thr Gly Ile
            100                 105                 110

Ser Ser Leu Ile Gly Met Phe Ala Gln Val Ser Gly Asn Glu Val
        115                 120                 125

<210> SEQ ID NO 52
<211> LENGTH: 131
<212> TYPE: PRT
<213> ORGANISM: Nephila inaurata madagascariensis

<400> SEQUENCE: 52

```
Gln Ala Asn Thr Pro Trp Ser Asp Thr Ala Thr Ala Asp Ala Phe Ile
1               5                   10                  15

Gln Asn Phe Leu Gly Ala Val Ser Gly Ser Gly Ala Phe Thr Pro Asp
            20                  25                  30

Gln Leu Asp Asp Met Ser Thr Val Gly Asp Thr Ile Met Ser Ala Met
        35                  40                  45

Asp Lys Met Ala Arg Ser Asn Lys Ser Ser Lys Ser Lys Leu Gln Ala
    50                  55                  60

Leu Asn Met Ala Phe Ala Ser Ser Met Ala Glu Ile Ala Ala Val Glu
65                  70                  75                  80

Gln Gly Gly Gln Ser Met Asp Val Lys Thr Asn Ala Ile Ala Asn Ala
                85                  90                  95

Leu Asp Ser Ala Phe Tyr Met Thr Thr Gly Ser Thr Asn Gln Gln Phe
            100                 105                 110

Val Asn Glu Met Arg Ser Leu Ile Asn Met Leu Ser Ala Ala Ala Val
        115                 120                 125

Asn Glu Val
    130
```

<210> SEQ ID NO 53
<211> LENGTH: 131
<212> TYPE: PRT
<213> ORGANISM: Nephila clavipes

<400> SEQUENCE: 53

```
Gln Ala Arg Ser Pro Trp Ser Asp Thr Ala Thr Ala Asp Ala Phe Ile
1               5                   10                  15

Gln Asn Phe Leu Ala Ala Val Ser Gly Ser Gly Ala Phe Thr Ser Asp
            20                  25                  30

Gln Leu Asp Asp Met Ser Thr Ile Gly Asp Thr Ile Met Ser Ala Met
        35                  40                  45

Asp Lys Met Ala Arg Ser Asn Lys Ser Ser Gln His Lys Leu Gln Ala
    50                  55                  60

Leu Asn Met Ala Phe Ala Ser Ser Met Ala Glu Ile Ala Ala Val Glu
65                  70                  75                  80

Gln Gly Gly Met Ser Met Ala Val Lys Thr Asn Ala Ile Val Asp Gly
                85                  90                  95

Leu Asn Ser Ala Phe Tyr Met Thr Thr Gly Ala Ala Asn Pro Gln Phe
            100                 105                 110

Val Asn Glu Met Arg Ser Leu Ile Ser Met Ile Ser Ala Ala Ser Ala
        115                 120                 125

Asn Glu Val
    130
```

<210> SEQ ID NO 54
<211> LENGTH: 129
<212> TYPE: PRT
<213> ORGANISM: Argiope bruennichi

<400> SEQUENCE: 54

```
Ala Val Pro Ser Val Phe Ser Ser Pro Asn Leu Ala Ser Gly Phe Leu
1               5                   10                  15

Gln Cys Leu Thr Phe Gly Ile Gly Asn Ser Pro Ala Phe Pro Thr Gln
            20                  25                  30

Glu Gln Gln Asp Leu Asp Ala Ile Ala Gln Val Ile Leu Asn Ala Val
        35                  40                  45

Ser Ser Asn Thr Gly Ala Thr Ala Ser Ala Arg Ala Gln Ala Leu Ser
    50                  55                  60

Thr Ala Leu Ala Ser Ser Leu Thr Asp Leu Leu Ile Ala Glu Ser Ala
65                  70                  75                  80

Glu Ser Asn Tyr Ser Asn Gln Leu Ser Glu Leu Thr Gly Ile Leu Ser
                85                  90                  95

Asp Cys Phe Ile Gln Thr Thr Gly Ser Asp Asn Pro Ala Phe Val Ser
            100                 105                 110

Arg Ile Gln Ser Leu Ile Ser Val Leu Ser Gln Asn Ala Asp Thr Asn
            115                 120                 125

Ile
```

<210> SEQ ID NO 55
<211> LENGTH: 129
<212> TYPE: PRT
<213> ORGANISM: Nephila clavata

<400> SEQUENCE: 55

```
Pro Val Pro Ser Val Phe Ser Ser Pro Ser Leu Ala Ser Gly Phe Leu
1               5                   10                  15

Gly Cys Leu Thr Thr Gly Ile Gly Leu Ser Pro Ala Phe Pro Phe Gln
            20                  25                  30

Glu Gln Gln Asp Leu Asp Asp Leu Ala Lys Val Ile Leu Ser Ala Val
        35                  40                  45

Thr Ser Asn Thr Asp Thr Ser Lys Ser Ala Arg Ala Gln Ala Leu Ser
    50                  55                  60

Thr Ala Leu Ala Ser Ser Leu Ala Asp Leu Leu Ile Ser Glu Ser Ser
65                  70                  75                  80

Gly Ser Ser Tyr Gln Thr Gln Ile Ser Ala Leu Thr Asn Ile Leu Ser
                85                  90                  95

Asp Cys Phe Val Thr Thr Thr Gly Ser Asn Asn Pro Ala Phe Val Ser
            100                 105                 110

Arg Val Gln Thr Leu Ile Gly Val Leu Ser Gln Ser Ser Ser Asn Ala
            115                 120                 125

Ile
```

<210> SEQ ID NO 56
<211> LENGTH: 128
<212> TYPE: PRT
<213> ORGANISM: Latrodectus hesperus

<400> SEQUENCE: 56

```
Ala Ser Val Asn Ile Phe Asn Ser Pro Asn Ala Ala Thr Ser Phe Leu
1               5                   10                  15

Asn Cys Leu Arg Ser Asn Ile Glu Ser Ser Pro Ala Phe Pro Phe Gln
            20                  25                  30

Glu Gln Ala Asp Leu Asp Ser Ile Ala Glu Val Ile Leu Ser Asp Val
        35                  40                  45

Ser Ser Val Asn Thr Ala Ser Ser Ala Thr Ser Leu Ala Leu Ser Thr
    50                  55                  60
```

```
Ala Leu Ala Ser Ser Leu Ala Glu Leu Leu Val Thr Glu Ser Ala Glu
 65                  70                  75                  80

Glu Asp Ile Asp Asn Gln Val Val Ala Leu Ser Thr Ile Leu Ser Gln
             85                  90                  95

Cys Phe Val Glu Thr Thr Gly Ser Pro Asn Pro Ala Phe Val Ala Ser
            100                 105                 110

Val Lys Ser Leu Leu Gly Val Leu Ser Gln Ser Ala Ser Asn Tyr Glu
        115                 120                 125
```

<210> SEQ ID NO 57
<211> LENGTH: 130
<212> TYPE: PRT
<213> ORGANISM: Nephila clavipes

<400> SEQUENCE: 57

```
Ile Ala Asn Ser Pro Phe Ser Asn Pro Asn Thr Ala Glu Ala Phe Ala
 1               5                  10                  15

Arg Ser Phe Val Ser Asn Ile Val Ser Ser Gly Glu Phe Gly Ala Gln
             20                  25                  30

Gly Ala Glu Asp Phe Asp Asp Ile Ile Gln Ser Leu Ile Gln Ala Gln
             35                  40                  45

Ser Met Gly Lys Gly Arg His Asp Thr Lys Ala Lys Ala Lys Ala Met
 50                  55                  60

Gln Val Ala Leu Ala Ser Ser Ile Ala Glu Leu Val Ile Ala Glu Ser
 65                  70                  75                  80

Ser Gly Gly Asp Val Gln Arg Lys Thr Asn Val Ile Ser Asn Ala Leu
             85                  90                  95

Arg Asn Ala Leu Met Ser Thr Thr Gly Ser Pro Asn Glu Glu Phe Val
            100                 105                 110

His Glu Val Gln Asp Leu Ile Gln Met Leu Ser Gln Glu Gln Ile Asn
        115                 120                 125

Glu Val
    130
```

<210> SEQ ID NO 58
<211> LENGTH: 130
<212> TYPE: PRT
<213> ORGANISM: Nephila inaurata madagascariensis

<400> SEQUENCE: 58

```
Ile Val Asn Ser Pro Phe Ser Asn Pro Asn Thr Ala Glu Ala Phe Ala
 1               5                  10                  15

Arg Ser Phe Val Ser Asn Val Val Ser Ser Gly Glu Phe Gly Ala Gln
             20                  25                  30

Gly Ala Glu Asp Phe Asp Asp Ile Ile Gln Ser Leu Ile Gln Ala Gln
             35                  40                  45

Ser Met Gly Lys Gly Arg His Asp Thr Lys Ala Lys Ala Lys Ala Met
 50                  55                  60

Gln Val Ala Leu Ala Ser Ser Ile Ala Glu Leu Val Ile Ala Glu Ser
 65                  70                  75                  80

Ser Gly Gly Asp Val Gln Arg Lys Thr Asn Val Ile Ser Asn Ala Leu
             85                  90                  95

Arg Asn Ala Leu Met Ser Thr Thr Gly Ser Pro Asn Glu Glu Phe Val
            100                 105                 110

His Glu Val Gln Asp Leu Ile Gln Met Leu Ser Gln Glu Gln Ile Asn
        115                 120                 125
```

Glu Val
    130

<210> SEQ ID NO 59
<211> LENGTH: 1778
<212> TYPE: DNA
<213> ORGANISM: Artificial Sequence
<220> FEATURE:
<223> OTHER INFORMATION: Fusion protein

<400> SEQUENCE: 59

| | | | | | |
|---|---|---|---|---|---|
| atgggcagca | gcggccatca | tcatcatcat | catatggagg | tgcagctgtt | ggagtctggg | 60 |
| ggaggcttgg | tacagcctgg | ggggtccctg | agactctcct | gtgcagcctc | tggattcacc | 120 |
| ttcagtagtt | atgaaatgaa | ctgggtccgc | caggctccag | gaaggggct | ggagtgggtc | 180 |
| tcaggcatta | gtggtagtgg | tggtttcaca | tactacgcag | actccgtgaa | gggccgattc | 240 |
| accatctcca | gagacaattc | caagaacacg | ctgtatctgc | aaatgaacag | cctgagagcc | 300 |
| gaggacactg | ccatgtatta | ctgtgcgaga | gaggggtacc | aggatgcttt | tgatatctgg | 360 |
| ggccagggta | cactggtcac | cgtgagcagc | ggtggaggcg | gttcaggcgg | aggtggatcc | 420 |
| ggcggtggcg | gatcgcagtc | tgtgctgact | cagccaccct | cagcgtctgg | gacccccggg | 480 |
| cagagggtca | ccatctcctg | cactgggagc | agctccaaca | tcggggcagg | ttatgatgta | 540 |
| cactggtatc | agcagctccc | aggaacggcc | cccaaactcc | tcatctatag | taataatcag | 600 |
| cggccctcag | gggtccctga | ccgattctct | ggctccaagt | ctggcacctc | agcctccctg | 660 |
| gccatcagtg | ggctccggtc | cgaggatgag | gctgattatt | actgtgcagc | atgggatgac | 720 |
| agcctgagtg | gtccgccttg | cgtgttcggc | ggaggaacca | agctgacggt | cctaggtgaa | 780 |
| caaaaactca | tctcagaaga | ggatctgtct | ggatcagcgg | ctgcagggaa | ttcaggtcaa | 840 |
| ggtggatatg | gtggactagg | tcaaggagga | tatggacaag | gtgcaggaag | ttctgcagcc | 900 |
| gctgccgccg | ccgcagcagc | cgccgcagca | ggtggacaag | gtggacaagg | tcaaggagga | 960 |
| tatggacaag | gttcaggagg | ttctgcagcc | gccgccgccg | ccgcagcagc | agcagcagct | 1020 |
| gcagcagctg | gacgaggtca | aggaggatat | ggtcaaggtt | ctggaggtaa | tgctgctgcc | 1080 |
| gcagccgctg | ccgccgccgc | cgccgctgca | gcagccggac | agggaggtca | aggtggatat | 1140 |
| ggtagacaaa | gccaaggtgc | tggttccgct | gctgctgctg | ctgctgctgc | tgccgctgct | 1200 |
| gctgctgcag | gatctggaca | aggtggatac | ggtggacaag | gtcaaggagg | ttatggtcag | 1260 |
| agtagtgctt | ctgcttcagc | tgctgcgtca | gctgctagta | ctgtagctaa | ttcggtgagt | 1320 |
| cgcctctcat | cgccttccgc | agtatctcga | gtttcttcag | cagtttctag | cttggtttca | 1380 |
| aatggtcaag | tgaatatggc | agcgttacct | aatatcattt | ccaacatttc | ttcttctgtc | 1440 |
| agtgcatctg | ctcctggtgc | ttctggatgt | gaggtcatag | tgcaagctct | actcgaagtc | 1500 |
| atcactgctc | ttgttcaaat | cgttagttct | tctagtgttg | gatatattaa | tccatctgct | 1560 |
| gtgaaccaaa | ttactaatgt | tgttgctaat | gccatggctc | aagtaatggg | ctaatgataa | 1620 |
| gcttctcgag | ggcctcccag | gccggcgcgc | cccaccgctg | agcaataact | agcataaccc | 1680 |
| cttgggccct | ctaaacgggt | cttgaggggt | tttttgctga | aaggaggaac | tatatccgga | 1740 |
| ttggcgaatg | ggacgcgccc | tgtagcggcg | cattaagc | | | 1778 |

<210> SEQ ID NO 60
<211> LENGTH: 1599
<212> TYPE: DNA
<213> ORGANISM: Artificial Sequence

```
<220> FEATURE:
<223> OTHER INFORMATION: Fusion protein

<400> SEQUENCE: 60
atgcatcatc atcatcatca tggtcaaggt ggatatggtg gactaggtca aggaggatat      60
ggacaaggtg caggaagttc tgcagccgct gccgccgccg cagcagccgc cgcagcaggt    120
ggacaaggtg gacaaggtca aggaggatat ggacaaggtt caggaggttc tgcagccgcc    180
gccgccgccg cagcagcagc agcagctgca gcagctggac gaggtcaagg aggatatggt    240
caaggttctg gaggtaatgc tgctgccgca gccgctgccg ccgccgccgc cgctgcagca    300
gccggacagg gaggtcaagg tggatatggt agacaaagcc aaggtgctgg ttccgctgct    360
gctgctgctg ctgctgctgc cgctgctgct gctgcaggat ctggacaagg tggatacggt    420
ggacaaggtc aaggaggtta tggtcagagt agtgcttctg cttcagctgc tgcgtcagct    480
gctagtactg tagctaattc ggtgagtcgc ctctcatcgc cttccgcagt atctcgagtt    540
tcttcagcag tttctagctt ggtttcaaat ggtcaagtga atatggcagc gttacctaat    600
atcatttcca acatttcttc ttctgtcagt gcatctgctc ctggtgcttc tggatgtgag    660
gtcatagtgc aagctctact cgaagtcatc actgctcttg ttcaaatcgt tagttcttct    720
agtgttggat atattaatcc atctgctgtg aaccaaatta ctaatgttgt tgctaatgcc    780
atggctcaag taatgggcgg gaattcgaga gtgcagctgt tggagtctgg gggaggcttg    840
gtacagcctg ggggtccct gagactctcc tgtgcagcct ctggattcac cttcagtagt    900
tatgaaatga actgggtccg ccaggctcca gggaaggggc tggagtgggt ctcaggcatt    960
agtggtagtg gtggtttcac atactacgca gactccgtga agggccgatt caccatctcc   1020
agagacaatt ccaagaacac gctgtatctg caaatgaaca gcctgagagc cgaggacact   1080
gccatgtatt actgtgcgag agaggggtac caggatgctt ttgatatctg gggccagggt   1140
acactggtca ccgtgagcag cggtggaggc ggttcaggcg gaggtggatc cggcggtggc   1200
ggatcgcagt ctgtgctgac tcagccaccc tcagcgtctg gaccccgg gcagagggtc   1260
accatctcct gcactgggag cagctccaac atcggggcag ttatgatgt acactggtat   1320
cagcagctcc caggaacggc ccccaaactc ctcatctata gtaataatca gcggccctca   1380
ggggtccctg accgattctc tggctccaag tctggcacct cagcctccct ggccatcagt   1440
gggctccggt ccgaggatga ggctgattat tactgtgcag catgggatga cagcctgagt   1500
ggtccgcctt cgtgttcgg cggaggaacc aagctgacgg tcctaggtga caaaaactc   1560
atctcagaag aggatctgtc tggatcagcg gctgcataa                           1599

<210> SEQ ID NO 61
<211> LENGTH: 537
<212> TYPE: PRT
<213> ORGANISM: Artificial Sequence
<220> FEATURE:
<223> OTHER INFORMATION: Fusion protein

<400> SEQUENCE: 61

Met Gly Ser Ser Gly His His His His His His Met Glu Val Gln Leu
1               5                   10                  15

Leu Glu Ser Gly Gly Gly Leu Val Gln Pro Gly Gly Ser Leu Arg Leu
            20                  25                  30

Ser Cys Ala Ala Ser Gly Phe Thr Phe Ser Ser Tyr Glu Met Asn Trp
        35                  40                  45

Val Arg Gln Ala Pro Gly Lys Gly Leu Glu Trp Val Ser Gly Ile Ser
```

```
            50                  55                  60
Gly Ser Gly Gly Phe Thr Tyr Tyr Ala Asp Ser Val Lys Gly Arg Phe
 65                  70                  75                  80

Thr Ile Ser Arg Asp Asn Ser Lys Asn Thr Leu Tyr Leu Gln Met Asn
                     85                  90                  95

Ser Leu Arg Ala Glu Asp Thr Ala Met Tyr Tyr Cys Ala Arg Glu Gly
                100                 105                 110

Tyr Gln Asp Ala Phe Asp Ile Trp Gly Gln Gly Thr Leu Val Thr Val
                115                 120                 125

Ser Ser Gly Gly Gly Gly Ser Gly Gly Gly Gly Ser Gly Gly Gly Gly
130                 135                 140

Ser Gln Ser Val Leu Thr Gln Pro Pro Ser Ala Ser Gly Thr Pro Gly
145                 150                 155                 160

Gln Arg Val Thr Ile Ser Cys Thr Gly Ser Ser Ser Asn Ile Gly Ala
                165                 170                 175

Gly Tyr Asp Val His Trp Tyr Gln Gln Leu Pro Gly Thr Ala Pro Lys
                180                 185                 190

Leu Leu Ile Tyr Ser Asn Asn Gln Arg Pro Ser Gly Val Pro Asp Arg
                195                 200                 205

Phe Ser Gly Ser Lys Ser Gly Thr Ser Ala Ser Leu Ala Ile Ser Gly
210                 215                 220

Leu Arg Ser Glu Asp Glu Ala Asp Tyr Tyr Cys Ala Ala Trp Asp Asp
225                 230                 235                 240

Ser Leu Ser Gly Pro Pro Cys Val Phe Gly Gly Gly Thr Lys Leu Thr
                245                 250                 255

Val Leu Gly Glu Gln Lys Leu Ile Ser Glu Glu Asp Leu Ser Gly Ser
                260                 265                 270

Ala Ala Ala Gly Asn Ser Gly Gln Gly Gly Tyr Gly Gly Leu Gly Gln
                275                 280                 285

Gly Gly Tyr Gly Gln Gly Ala Gly Ser Ser Ala Ala Ala Ala Ala Ala
                290                 295                 300

Ala Ala Ala Ala Ala Ala Gly Gly Gln Gly Gly Gln Gly Gln Gly Gly
305                 310                 315                 320

Tyr Gly Gln Gly Ser Gly Gly Ser Ala Ala Ala Ala Ala Ala Ala Ala
                325                 330                 335

Ala Ala Ala Ala Ala Ala Gly Arg Gly Gln Gly Gly Tyr Gly Gln
                340                 345                 350

Gly Ser Gly Gly Asn Ala Ala Ala Ala Ala Ala Ala Ala Ala Ala Ala
                355                 360                 365

Ala Ala Ala Ala Gly Gln Gly Gly Gln Gly Gly Tyr Gly Arg Gln Ser
                370                 375                 380

Gln Gly Ala Gly Ser Ala Ala Ala Ala Ala Ala Ala Ala Ala Ala Ala
385                 390                 395                 400

Ala Ala Ala Gly Ser Gly Gln Gly Gly Tyr Gly Gly Gln Gly Gln Gly
                405                 410                 415

Gly Tyr Gly Gln Ser Ser Ala Ser Ala Ser Ala Ala Ala Ser Ala Ala
                420                 425                 430

Ser Thr Val Ala Asn Ser Val Ser Arg Leu Ser Ser Pro Ser Ala Val
                435                 440                 445

Ser Arg Val Ser Ser Ala Val Ser Ser Leu Val Ser Asn Gly Gln Val
                450                 455                 460

Asn Met Ala Ala Leu Pro Asn Ile Ile Ser Asn Ile Ser Ser Ser Val
465                 470                 475                 480
```

```
Ser Ala Ser Ala Pro Gly Ala Ser Gly Cys Glu Val Ile Val Gln Ala
            485                 490                 495

Leu Leu Glu Val Ile Thr Ala Leu Val Gln Ile Val Ser Ser Ser Ser
            500                 505                 510

Val Gly Tyr Ile Asn Pro Ser Ala Val Asn Gln Ile Thr Asn Val Val
            515                 520                 525

Ala Asn Ala Met Ala Gln Val Met Gly
    530                 535

<210> SEQ ID NO 62
<211> LENGTH: 532
<212> TYPE: PRT
<213> ORGANISM: Artificial Sequence
<220> FEATURE:
<223> OTHER INFORMATION: Fusion protein

<400> SEQUENCE: 62

Met His His His His His Gly Gln Gly Gly Tyr Gly Gly Leu Gly
1               5                   10                  15

Gln Gly Gly Tyr Gly Gln Gly Ala Gly Ser Ser Ala Ala Ala Ala
            20                  25                  30

Ala Ala Ala Ala Ala Ala Gly Gly Gln Gly Gly Gln Gly Gln Gly
            35                  40                  45

Gly Tyr Gly Gln Gly Ser Gly Ser Ala Ala Ala Ala Ala Ala Ala
    50                  55                  60

Ala Ala Ala Ala Ala Ala Ala Gly Arg Gly Gln Gly Gly Tyr Gly
65                  70                  75                  80

Gln Gly Ser Gly Gly Asn Ala Ala Ala Ala Ala Ala Ala Ala Ala
            85                  90                  95

Ala Ala Ala Ala Gly Gln Gly Gly Gln Gly Gly Tyr Gly Arg Gln
            100                 105                 110

Ser Gln Gly Ala Gly Ser Ala Ala Ala Ala Ala Ala Ala Ala Ala
            115                 120                 125

Ala Ala Ala Ala Gly Ser Gly Gln Gly Gly Tyr Gly Gly Gln Gly Gln
            130                 135                 140

Gly Gly Tyr Gly Gln Ser Ser Ala Ser Ala Ser Ala Ala Ser Ala
145                 150                 155                 160

Ala Ser Thr Val Ala Asn Ser Val Ser Arg Leu Ser Ser Pro Ser Ala
            165                 170                 175

Val Ser Arg Val Ser Ser Ala Val Ser Ser Leu Val Ser Asn Gly Gln
            180                 185                 190

Val Asn Met Ala Ala Leu Pro Asn Ile Ile Ser Asn Ile Ser Ser Ser
            195                 200                 205

Val Ser Ala Ser Ala Pro Gly Ala Ser Gly Cys Glu Val Ile Val Gln
            210                 215                 220

Ala Leu Leu Glu Val Ile Thr Ala Leu Val Gln Ile Val Ser Ser Ser
225                 230                 235                 240

Ser Val Gly Tyr Ile Asn Pro Ser Ala Val Asn Gln Ile Thr Asn Val
            245                 250                 255

Val Ala Asn Ala Met Ala Gln Val Met Gly Gly Asn Ser Glu Val Gln
            260                 265                 270

Leu Leu Glu Ser Gly Gly Gly Leu Val Gln Pro Gly Gly Ser Leu Arg
            275                 280                 285

Leu Ser Cys Ala Ala Ser Gly Phe Thr Phe Ser Ser Tyr Glu Met Asn
            290                 295                 300
```

-continued

```
Trp Val Arg Gln Ala Pro Gly Lys Gly Leu Glu Trp Val Ser Gly Ile
305                 310                 315                 320

Ser Gly Ser Gly Gly Phe Thr Tyr Tyr Ala Asp Ser Val Lys Gly Arg
            325                 330                 335

Phe Thr Ile Ser Arg Asp Asn Ser Lys Asn Thr Leu Tyr Leu Gln Met
        340                 345                 350

Asn Ser Leu Arg Ala Glu Asp Thr Ala Met Tyr Tyr Cys Ala Arg Glu
    355                 360                 365

Gly Tyr Gln Asp Ala Phe Asp Ile Trp Gly Gln Gly Thr Leu Val Thr
370                 375                 380

Val Ser Gly Gly Gly Gly Ser Gly Gly Gly Gly Ser Gly Gly Gly Gly
385                 390                 395                 400

Gly Ser Gln Ser Val Leu Thr Gln Pro Pro Ser Ala Ser Gly Thr Pro
            405                 410                 415

Gly Gln Arg Val Thr Ile Ser Cys Thr Gly Ser Ser Ser Asn Ile Gly
        420                 425                 430

Ala Gly Tyr Asp Val His Trp Tyr Gln Gln Leu Pro Gly Thr Ala Pro
    435                 440                 445

Lys Leu Leu Ile Tyr Ser Asn Asn Gln Arg Pro Ser Gly Val Pro Asp
450                 455                 460

Arg Phe Ser Gly Ser Lys Ser Gly Thr Ser Ala Ser Leu Ala Ile Ser
465                 470                 475                 480

Gly Leu Arg Ser Glu Asp Glu Ala Asp Tyr Tyr Cys Ala Ala Trp Asp
            485                 490                 495

Asp Ser Leu Ser Gly Pro Pro Cys Val Phe Gly Gly Gly Thr Lys Leu
        500                 505                 510

Thr Val Leu Gly Glu Gln Lys Leu Ile Ser Glu Glu Asp Leu Ser Gly
    515                 520                 525

Ser Ala Ala Ala
    530

<210> SEQ ID NO 63
<211> LENGTH: 383
<212> TYPE: PRT
<213> ORGANISM: Artificial Sequence
<220> FEATURE:
<223> OTHER INFORMATION: Fusion protein

<400> SEQUENCE: 63

Met Gly Ser Ser Gly His His His His His Met Glu Val Gln Leu
1               5                   10                  15

Leu Glu Ser Gly Gly Gly Leu Val Gln Pro Gly Gly Ser Leu Arg Leu
                20                  25                  30

Ser Cys Ala Ala Ser Gly Phe Thr Phe Ser Ser Tyr Glu Met Asn Trp
            35                  40                  45

Val Arg Gln Ala Pro Gly Lys Gly Leu Glu Trp Val Ser Gly Ile Ser
        50                  55                  60

Gly Ser Gly Gly Phe Thr Tyr Tyr Ala Asp Ser Val Lys Gly Arg Phe
65                  70                  75                  80

Thr Ile Ser Arg Asp Asn Ser Lys Asn Thr Leu Tyr Leu Gln Met Asn
                85                  90                  95

Ser Leu Arg Ala Glu Asp Thr Ala Met Tyr Tyr Cys Ala Arg Glu Gly
            100                 105                 110

Tyr Gln Asp Ala Phe Asp Ile Trp Gly Gln Gly Thr Leu Val Thr Val
        115                 120                 125
```

```
Ser Ser Gly Gly Gly Ser Gly Gly Gly Ser Gly Gly Gly
    130                 135                 140

Ser Gln Ser Val Leu Thr Gln Pro Pro Ser Ala Ser Gly Thr Pro Gly
145                 150                 155                 160

Gln Arg Val Thr Ile Ser Cys Thr Gly Ser Ser Asn Ile Gly Ala
                165                 170                 175

Gly Tyr Asp Val His Trp Tyr Gln Gln Leu Pro Gly Thr Ala Pro Lys
            180                 185                 190

Leu Leu Ile Tyr Ser Asn Asn Gln Arg Pro Ser Gly Val Pro Asp Arg
            195                 200                 205

Phe Ser Gly Ser Lys Ser Gly Thr Ser Ala Ser Leu Ala Ile Ser Gly
    210                 215                 220

Leu Arg Ser Glu Asp Glu Ala Asp Tyr Tyr Cys Ala Ala Trp Asp Asp
225                 230                 235                 240

Ser Leu Ser Gly Pro Pro Cys Val Phe Gly Gly Thr Lys Leu Thr
                245                 250                 255

Val Leu Gly Glu Gln Lys Leu Ile Ser Glu Glu Asp Leu Ser Gly Ser
                260                 265                 270

Ala Ala Ala Ser Ala Ala Ser Thr Val Ala Asn Ser Val Ser Arg Leu
            275                 280                 285

Ser Ser Pro Ser Ala Val Ser Arg Val Ser Ser Ala Val Ser Ser Leu
            290                 295                 300

Val Ser Asn Gly Gln Val Asn Met Ala Ala Leu Pro Asn Ile Ile Ser
305                 310                 315                 320

Asn Ile Ser Ser Ser Val Ser Ala Ser Ala Pro Gly Ala Ser Gly Cys
                325                 330                 335

Glu Val Ile Val Gln Ala Leu Leu Glu Val Ile Thr Ala Leu Val Gln
            340                 345                 350

Ile Val Ser Ser Ser Ser Val Gly Tyr Ile Asn Pro Ser Ala Val Asn
            355                 360                 365

Gln Ile Thr Asn Val Val Ala Asn Ala Met Ala Gln Val Met Gly
            370                 375                 380

<210> SEQ ID NO 64
<211> LENGTH: 378
<212> TYPE: PRT
<213> ORGANISM: Artificial Sequence
<220> FEATURE:
<223> OTHER INFORMATION: Fusion protein

<400> SEQUENCE: 64

Met His His His His His Ser Ala Ala Ser Thr Val Ala Asn Ser
1               5                   10                  15

Val Ser Arg Leu Ser Ser Pro Ser Ala Val Ser Arg Val Ser Ser Ala
                20                  25                  30

Val Ser Ser Leu Val Ser Asn Gly Gln Val Asn Met Ala Ala Leu Pro
            35                  40                  45

Asn Ile Ile Ser Asn Ile Ser Ser Ser Val Ser Ala Ser Ala Pro Gly
        50                  55                  60

Ala Ser Gly Cys Glu Val Ile Val Gln Ala Leu Leu Glu Val Ile Thr
65                  70                  75                  80

Ala Leu Val Gln Ile Val Ser Ser Ser Ser Val Gly Tyr Ile Asn Pro
                85                  90                  95

Ser Ala Val Asn Gln Ile Thr Asn Val Val Ala Asn Ala Met Ala Gln
                100                 105                 110
```

```
Val Met Gly Glu Val Gln Leu Leu Glu Ser Gly Gly Leu Val Gln
        115                 120                 125
Pro Gly Gly Ser Leu Arg Leu Ser Cys Ala Ala Ser Gly Phe Thr Phe
    130                 135                 140
Ser Ser Tyr Glu Met Asn Trp Val Arg Gln Ala Pro Gly Lys Gly Leu
145                 150                 155                 160
Glu Trp Val Ser Gly Ile Ser Gly Ser Gly Gly Phe Thr Tyr Tyr Ala
                165                 170                 175
Asp Ser Val Lys Gly Arg Phe Thr Ile Ser Arg Asp Asn Ser Lys Asn
            180                 185                 190
Thr Leu Tyr Leu Gln Met Asn Ser Leu Arg Ala Glu Asp Thr Ala Met
        195                 200                 205
Tyr Tyr Cys Ala Arg Glu Gly Tyr Gln Asp Ala Phe Asp Ile Trp Gly
    210                 215                 220
Gln Gly Thr Leu Val Thr Val Ser Ser Gly Gly Gly Ser Gly Gly
225                 230                 235                 240
Gly Gly Ser Gly Gly Gly Gly Ser Gln Ser Val Leu Thr Gln Pro Pro
                245                 250                 255
Ser Ala Ser Gly Thr Pro Gly Gln Arg Val Thr Ile Ser Cys Thr Gly
            260                 265                 270
Ser Ser Ser Asn Ile Gly Ala Gly Tyr Asp Val His Trp Tyr Gln Gln
        275                 280                 285
Leu Pro Gly Thr Ala Pro Lys Leu Leu Ile Tyr Ser Asn Asn Gln Arg
    290                 295                 300
Pro Ser Gly Val Pro Asp Arg Phe Ser Gly Ser Lys Ser Gly Thr Ser
305                 310                 315                 320
Ala Ser Leu Ala Ile Ser Gly Leu Arg Ser Glu Asp Glu Ala Asp Tyr
                325                 330                 335
Tyr Cys Ala Ala Trp Asp Asp Ser Leu Ser Gly Pro Pro Cys Val Phe
            340                 345                 350
Gly Gly Gly Thr Lys Leu Thr Val Leu Gly Glu Gln Lys Leu Ile Ser
        355                 360                 365
Glu Glu Asp Leu Ser Gly Ser Ala Ala Ala
    370                 375

<210> SEQ ID NO 65
<211> LENGTH: 551
<212> TYPE: PRT
<213> ORGANISM: Artificial Sequence
<220> FEATURE:
<223> OTHER INFORMATION: Fusion protein

<400> SEQUENCE: 65

Met Gly Ser Ser Gly His His His His His Met Glu Val Gln Leu
1               5                   10                  15
Leu Glu Ser Gly Gly Gly Leu Val Gln Pro Gly Gly Ser Leu Arg Leu
            20                  25                  30
Ser Cys Ala Ala Ser Gly Phe Thr Phe Ser Ser Tyr Glu Met Asn Trp
        35                  40                  45
Val Arg Gln Ala Pro Gly Lys Gly Leu Glu Trp Val Ser Gly Ile Ser
    50                  55                  60
Gly Ser Gly Gly Phe Thr Tyr Tyr Ala Asp Ser Val Lys Gly Arg Phe
65                  70                  75                  80
Thr Ile Ser Arg Asp Asn Ser Lys Asn Thr Leu Tyr Leu Gln Met Asn
                85                  90                  95
```

```
Ser Leu Arg Ala Glu Asp Thr Ala Met Tyr Tyr Cys Ala Arg Glu Gly
            100                 105                 110

Tyr Gln Asp Ala Phe Asp Ile Trp Gly Gln Gly Thr Leu Val Thr Val
            115                 120                 125

Ser Ser Gly Gly Gly Gly Ser Gly Gly Gly Ser Gly Gly Gly Gly
            130                 135                 140

Ser Gln Ser Val Leu Thr Gln Pro Pro Ser Ala Ser Gly Thr Pro Gly
145                 150                 155                 160

Gln Arg Val Thr Ile Ser Cys Thr Gly Ser Ser Ser Asn Ile Gly Ala
                165                 170                 175

Gly Tyr Asp Val His Trp Tyr Gln Gln Leu Pro Gly Thr Ala Pro Lys
            180                 185                 190

Leu Leu Ile Tyr Ser Asn Asn Gln Arg Pro Ser Gly Val Pro Asp Arg
            195                 200                 205

Phe Ser Gly Ser Lys Ser Gly Thr Ser Ala Ser Leu Ala Ile Ser Gly
            210                 215                 220

Leu Arg Ser Glu Asp Glu Ala Asp Tyr Tyr Cys Ala Ala Trp Asp Asp
225                 230                 235                 240

Ser Leu Ser Gly Pro Pro Cys Val Phe Gly Gly Gly Thr Lys Leu Thr
                245                 250                 255

Val Leu Gly Glu Gln Lys Leu Ile Ser Glu Glu Asp Leu Ser Gly Ser
            260                 265                 270

Ala Ala Ala Ser His Thr Thr Pro Trp Thr Asn Pro Gly Leu Ala Glu
                275                 280                 285

Asn Phe Met Asn Ser Phe Met Gln Gly Leu Ser Ser Met Pro Gly Phe
            290                 295                 300

Thr Ala Ser Gln Leu Asp Asp Met Ser Thr Ile Ala Gln Ser Met Val
305                 310                 315                 320

Gln Ser Ile Gln Ser Leu Ala Ala Gln Gly Arg Thr Ser Pro Asn Lys
                325                 330                 335

Leu Gln Ala Leu Asn Met Ala Phe Ala Ser Ser Met Ala Glu Ile Ala
            340                 345                 350

Ala Ser Glu Glu Gly Gly Gly Ser Leu Ser Thr Lys Thr Ser Ser Ile
            355                 360                 365

Ala Ser Ala Met Ser Asn Ala Phe Leu Gln Thr Thr Gly Val Val Asn
            370                 375                 380

Gln Pro Phe Ile Asn Glu Ile Thr Gln Leu Val Ser Met Phe Ala Gln
385                 390                 395                 400

Ala Gly Met Asn Asp Val Ser Ala Ser Ala Gly Ala Ser Ala
                405                 410                 415

Ala Ala Ser Ala Gly Ala Gly Ser Gly Asn Ser Gly Ile Gln Gly Tyr
            420                 425                 430

Gly Gln Ser Ser Ala Ser Ala Ser Ala Ala Ser Ala Ala Ser Thr
            435                 440                 445

Val Ala Asn Ser Val Ser Arg Leu Ser Ser Pro Ser Ala Val Ser Arg
            450                 455                 460

Val Ser Ser Ala Val Ser Ser Leu Val Ser Asn Gly Gln Val Asn Met
465                 470                 475                 480

Ala Ala Leu Pro Asn Ile Ile Ser Asn Ile Ser Ser Val Ser Ala
                485                 490                 495

Ser Ala Pro Gly Ala Ser Gly Cys Glu Val Ile Val Gln Ala Leu Leu
            500                 505                 510
```

```
Glu Val Ile Thr Ala Leu Val Gln Ile Val Ser Ser Ser Val Gly
            515                 520                 525
Tyr Ile Asn Pro Ser Ala Val Asn Gln Ile Thr Asn Val Val Ala Asn
530                 535                 540
Ala Met Ala Gln Val Met Gly
545                 550

<210> SEQ ID NO 66
<211> LENGTH: 546
<212> TYPE: PRT
<213> ORGANISM: Artificial Sequence
<220> FEATURE:
<223> OTHER INFORMATION: Fusion protein

<400> SEQUENCE: 66

His His His His His Met Ser His Thr Thr Pro Trp Thr Asn Pro
1               5                   10                  15
Gly Leu Ala Glu Asn Phe Met Asn Ser Phe Met Gln Gly Leu Ser Ser
                20                  25                  30
Met Pro Gly Phe Thr Ala Ser Gln Leu Asp Asp Met Ser Thr Ile Ala
            35                  40                  45
Gln Ser Met Val Gln Ser Ile Gln Ser Leu Ala Ala Gln Gly Arg Thr
    50                  55                  60
Ser Pro Asn Lys Leu Gln Ala Leu Asn Met Ala Phe Ala Ser Ser Met
65                  70                  75                  80
Ala Glu Ile Ala Ala Ser Glu Glu Gly Gly Ser Leu Ser Thr Lys
                85                  90                  95
Thr Ser Ser Ile Ala Ser Ala Met Ser Asn Ala Phe Leu Gln Thr Thr
            100                 105                 110
Gly Val Val Asn Gln Pro Phe Ile Asn Glu Ile Thr Gln Leu Val Ser
        115                 120                 125
Met Phe Ala Gln Ala Gly Met Asn Asp Val Ser Ala Ser Ala Ser Ala
    130                 135                 140
Gly Ala Ser Ala Ala Ala Ser Ala Gly Ala Gly Ser Gly Asn Ser Gly
145                 150                 155                 160
Ile Gln Gly Tyr Gly Gln Ser Ser Ala Ser Ala Ala Ala Ser
                165                 170                 175
Ala Ala Ser Thr Val Ala Asn Ser Val Ser Arg Leu Ser Ser Pro Ser
            180                 185                 190
Ala Val Ser Arg Val Ser Ser Ala Val Ser Ser Leu Val Ser Asn Gly
        195                 200                 205
Gln Val Asn Met Ala Ala Leu Pro Asn Ile Ile Ser Asn Ile Ser Ser
    210                 215                 220
Ser Val Ser Ala Ser Ala Pro Gly Ala Ser Gly Cys Glu Val Ile Val
225                 230                 235                 240
Gln Ala Leu Leu Glu Val Ile Thr Ala Leu Val Gln Ile Val Ser Ser
                245                 250                 255
Ser Ser Val Gly Tyr Ile Asn Pro Ser Ala Val Asn Gln Ile Thr Asn
            260                 265                 270
Val Val Ala Asn Ala Met Ala Gln Val Met Gly Glu Val Gln Leu Leu
        275                 280                 285
Glu Ser Gly Gly Gly Leu Val Gln Pro Gly Gly Ser Leu Arg Leu Ser
    290                 295                 300
Cys Ala Ala Ser Gly Phe Thr Phe Ser Ser Tyr Glu Met Asn Trp Val
305                 310                 315                 320
```

-continued

```
Arg Gln Ala Pro Gly Lys Gly Leu Glu Trp Val Ser Gly Ile Ser Gly
                325                 330                 335

Ser Gly Gly Phe Thr Tyr Tyr Ala Asp Ser Val Lys Gly Arg Phe Thr
            340                 345                 350

Ile Ser Arg Asp Asn Ser Lys Asn Thr Leu Tyr Leu Gln Met Asn Ser
        355                 360                 365

Leu Arg Ala Glu Asp Thr Ala Met Tyr Tyr Cys Ala Arg Glu Gly Tyr
    370                 375                 380

Gln Asp Ala Phe Asp Ile Trp Gly Gln Gly Thr Leu Val Thr Val Ser
385                 390                 395                 400

Ser Gly Gly Gly Ser Gly Gly Gly Ser Gly Gly Gly Ser
            405                 410                 415

Gln Ser Val Leu Thr Gln Pro Pro Ser Ala Ser Gly Thr Pro Gly Gln
            420                 425                 430

Arg Val Thr Ile Ser Cys Thr Gly Ser Ser Ser Asn Ile Gly Ala Gly
        435                 440                 445

Tyr Asp Val His Trp Tyr Gln Gln Leu Pro Gly Thr Ala Pro Lys Leu
    450                 455                 460

Leu Ile Tyr Ser Asn Asn Gln Arg Pro Ser Gly Val Pro Asp Arg Phe
465                 470                 475                 480

Ser Gly Ser Lys Ser Gly Thr Ser Ala Ser Leu Ala Ile Ser Gly Leu
            485                 490                 495

Arg Ser Glu Asp Glu Ala Asp Tyr Tyr Cys Ala Ala Trp Asp Asp Ser
        500                 505                 510

Leu Ser Gly Pro Pro Cys Val Phe Gly Gly Thr Lys Leu Thr Val
    515                 520                 525

Leu Gly Glu Gln Lys Leu Ile Ser Glu Glu Asp Leu Ser Gly Ser Ala
530                 535                 540

Ala Ala
545

<210> SEQ ID NO 67
<211> LENGTH: 688
<212> TYPE: PRT
<213> ORGANISM: Artificial Sequence
<220> FEATURE:
<223> OTHER INFORMATION: Fusion protein

<400> SEQUENCE: 67

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Glu Met Asn Trp Val Arg Gln Ala Pro Gly Lys Gly Leu Glu Trp
        35                  40                  45

Val Ser Gly Ile Ser Gly Ser Gly Gly Phe Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Met Tyr Tyr
            85                  90                  95

Cys Ala Arg Glu Gly Tyr Gln Asp Ala Phe Asp Ile Trp Gly Gln Gly
        100                 105                 110

Thr Leu Val Thr Val Ser Ser Gly Gly Gly Gly Ser Gly Gly Gly Gly
    115                 120                 125
```

-continued

```
Ser Gly Gly Gly Ser Gln Ser Val Leu Thr Gln Pro Pro Ser Ala
130                 135                 140

Ser Gly Thr Pro Gly Gln Arg Val Thr Ile Ser Cys Thr Gly Ser Ser
145                 150                 155                 160

Ser Asn Ile Gly Ala Gly Tyr Asp Val His Trp Tyr Gln Gln Leu Pro
            165                 170                 175

Gly Thr Ala Pro Lys Leu Leu Ile Tyr Ser Asn Asn Gln Arg Pro Ser
            180                 185                 190

Gly Val Pro Asp Arg Phe Ser Gly Ser Lys Ser Gly Thr Ser Ala Ser
            195                 200                 205

Leu Ala Ile Ser Gly Leu Arg Ser Glu Asp Glu Ala Asp Tyr Tyr Cys
210                 215                 220

Ala Ala Trp Asp Asp Ser Leu Ser Gly Pro Pro Cys Val Phe Gly Gly
225                 230                 235                 240

Gly Thr Lys Leu Thr Val Leu Gly Glu Gln Lys Leu Ile Ser Glu Glu
            245                 250                 255

Asp Leu Ser Gly Ser Ala Ala Met Lys Ala Ser His Thr Thr Pro
            260                 265                 270

Trp Thr Asn Pro Gly Leu Ala Glu Asn Phe Met Asn Ser Phe Met Gln
            275                 280                 285

Gly Leu Ser Ser Met Pro Gly Phe Thr Ala Ser Gln Leu Asp Asp Met
290                 295                 300

Ser Thr Ile Ala Gln Ser Met Val Gln Ser Ile Gln Ser Leu Ala Ala
305                 310                 315                 320

Gln Gly Arg Thr Ser Pro Asn Lys Leu Gln Ala Leu Asn Met Ala Phe
            325                 330                 335

Ala Ser Ser Met Ala Glu Ile Ala Ala Ser Glu Glu Gly Gly Gly Ser
            340                 345                 350

Leu Ser Thr Lys Thr Ser Ile Ala Ser Ala Met Ser Asn Ala Phe
            355                 360                 365

Leu Gln Thr Thr Gly Val Val Asn Gln Pro Phe Ile Asn Glu Ile Thr
370                 375                 380

Gln Leu Val Ser Met Phe Ala Gln Ala Gly Met Asn Asp Val Ser Ala
385                 390                 395                 400

Ser Ala Ser Ala Gly Ala Ser Ala Ala Ser Ala Gly Ala Ala Ser
            405                 410                 415

Gly Gln Gly Gly Tyr Gly Gly Leu Gly Gln Gly Gly Tyr Gly Gln Gly
            420                 425                 430

Ala Gly Ser Ser Ala Ala Ala Ala Ala Ala Ala Ala Ala
            435                 440                 445

Gly Gly Gln Gly Gly Gln Gly Gln Gly Gly Tyr Gly Gln Gly Ser Gly
            450                 455                 460

Gly Ser Ala Ala Ala Ala Ala Ala Ala Ala Ala Ala Ala Ala Ala
465                 470                 475                 480

Ala Gly Arg Gly Gln Gly Gly Tyr Gly Gln Gly Ser Gly Gly Asn Ala
            485                 490                 495

Ala Ala Ala Ala Ala Ala Ala Ala Ala Ala Ala Ala Ala Gly Gln
            500                 505                 510

Gly Gly Gln Gly Gly Tyr Gly Arg Gln Ser Gly Ala Gly Ser Ala
            515                 520                 525

Ala Ala Ala Ala Ala Ala Ala Ala Ala Ala Ala Ala Gly Ser Gly
            530                 535                 540

Gln Gly Gly Tyr Gly Gly Gln Gly Gln Gly Gly Tyr Gly Gln Ser Ser
```

```
                545                 550                 555                 560
Ala Ser Ala Ser Ala Ala Ser Ala Ala Ser Thr Val Ala Asn Ser
                565                 570                 575

Val Ser Arg Leu Ser Ser Pro Ser Ala Val Ser Arg Val Ser Ser Ala
                580                 585                 590

Val Ser Ser Leu Val Ser Asn Gly Gln Val Asn Met Ala Ala Leu Pro
                595                 600                 605

Asn Ile Ile Ser Asn Ile Ser Ser Val Ser Ala Ser Ala Pro Gly
                610                 615                 620

Ala Ser Gly Cys Glu Val Ile Val Gln Ala Leu Leu Glu Val Ile Thr
625                 630                 635                 640

Ala Leu Val Gln Ile Val Ser Ser Ser Val Gly Tyr Ile Asn Pro
                645                 650                 655

Ser Ala Val Asn Gln Ile Thr Asn Val Val Ala Asn Ala Met Ala Gln
                660                 665                 670

Val Met Gly Lys Leu Ala Ala Ala Leu Glu His His His His His
                675                 680                 685
```

<210> SEQ ID NO 68
<211> LENGTH: 692
<212> TYPE: PRT
<213> ORGANISM: Artificial Sequence
<220> FEATURE:
<223> OTHER INFORMATION: Fusion protein

<400> SEQUENCE: 68

```
Met Gly Ser Ser Gly His His His His His Met Lys Ala Ser His
1               5                   10                  15

Thr Thr Pro Trp Thr Asn Pro Gly Leu Ala Glu Asn Phe Met Asn Ser
                20                  25                  30

Phe Met Gln Gly Leu Ser Ser Met Pro Gly Phe Thr Ala Ser Gln Leu
                35                  40                  45

Asp Asp Met Ser Thr Ile Ala Gln Ser Met Val Gln Ser Ile Gln Ser
            50                  55                  60

Leu Ala Ala Gln Gly Arg Thr Ser Pro Asn Lys Leu Gln Ala Leu Asn
65              70                  75                  80

Met Ala Phe Ala Ser Ser Met Ala Glu Ile Ala Ala Ser Glu Glu Gly
                85                  90                  95

Gly Gly Ser Leu Ser Thr Lys Thr Ser Ser Ile Ala Ser Ala Met Ser
                100                 105                 110

Asn Ala Phe Leu Gln Thr Thr Gly Val Val Asn Gln Pro Phe Ile Asn
                115                 120                 125

Glu Ile Thr Gln Leu Val Ser Met Phe Ala Gln Ala Gly Met Asn Asp
            130                 135                 140

Val Ser Ala Ser Ala Ser Ala Gly Ala Ser Ala Ala Ser Ala Gly
145                 150                 155                 160

Ala Ala Ser Gly Gln Gly Gly Tyr Gly Gly Leu Gly Gln Gly Gly Tyr
                165                 170                 175

Gly Gln Gly Ala Gly Ser Ser Ala Ala Ala Ala Ala Ala Ala Ala
                180                 185                 190

Ala Ala Ala Gly Gly Gln Gly Gln Gly Gln Gly Gly Tyr Gly Gln
                195                 200                 205

Gly Ser Gly Gly Ser Ala Ala Ala Ala Ala Ala Ala Ala Ala Ala
                210                 215                 220

Ala Ala Ala Ala Gly Arg Gly Gln Gly Gly Tyr Gly Gln Gly Ser Gly
```

-continued

```
            225                 230                 235                 240
Gly Asn Ala Ala Ala Ala Ala Ala Ala Ala Ala Ala Ala
                245                 250                 255
Ala Gly Gln Gly Gly Gln Gly Gly Tyr Gly Arg Gln Ser Gln Gly Ala
                260                 265                 270
Gly Ser Ala Ala Ala Ala Ala Ala Ala Ala Ala Ala Ala Ala
                275                 280                 285
Gly Ser Gly Gln Gly Gly Tyr Gly Gly Gln Gly Gln Gly Gly Tyr Gly
                290                 295                 300
Gln Ser Ser Ala Ser Ala Ser Ala Ala Ala Ser Ala Ala Ser Thr Val
305                 310                 315                 320
Ala Asn Ser Val Ser Arg Leu Ser Ser Pro Ser Ala Val Ser Arg Val
                325                 330                 335
Ser Ser Ala Val Ser Ser Leu Val Ser Asn Gly Gln Val Asn Met Ala
                340                 345                 350
Ala Leu Pro Asn Ile Ile Ser Asn Ile Ser Ser Ser Val Ser Ala Ser
                355                 360                 365
Ala Pro Gly Ala Ser Gly Cys Glu Val Ile Val Gln Ala Leu Leu Glu
                370                 375                 380
Val Ile Thr Ala Leu Val Gln Ile Val Ser Ser Ser Ser Val Gly Tyr
385                 390                 395                 400
Ile Asn Pro Ser Ala Val Asn Gln Ile Thr Asn Val Val Ala Asn Ala
                405                 410                 415
Met Ala Gln Val Met Gly Lys Leu Ala Ala Leu Glu Glu Val Gln
                420                 425                 430
Leu Leu Glu Ser Gly Gly Gly Leu Val Gln Pro Gly Gly Ser Leu Arg
                435                 440                 445
Leu Ser Cys Ala Ala Ser Gly Phe Thr Phe Ser Ser Tyr Glu Met Asn
                450                 455                 460
Trp Val Arg Gln Ala Pro Gly Lys Gly Leu Glu Trp Val Ser Gly Ile
465                 470                 475                 480
Ser Gly Ser Gly Gly Phe Thr Tyr Tyr Ala Asp Ser Val Lys Gly Arg
                485                 490                 495
Phe Thr Ile Ser Arg Asp Asn Ser Lys Asn Thr Leu Tyr Leu Gln Met
                500                 505                 510
Asn Ser Leu Arg Ala Glu Asp Thr Ala Met Tyr Tyr Cys Ala Arg Glu
                515                 520                 525
Gly Tyr Gln Asp Ala Phe Asp Ile Trp Gly Gln Gly Thr Leu Val Thr
                530                 535                 540
Val Ser Ser Gly Gly Gly Gly Ser Gly Gly Gly Gly Ser Gly Gly Gly
545                 550                 555                 560
Gly Ser Gln Ser Val Leu Thr Gln Pro Pro Ser Ala Ser Gly Thr Pro
                565                 570                 575
Gly Gln Arg Val Thr Ile Ser Cys Thr Gly Ser Ser Ser Asn Ile Gly
                580                 585                 590
Ala Gly Tyr Asp Val His Trp Tyr Gln Gln Leu Pro Gly Thr Ala Pro
                595                 600                 605
Lys Leu Leu Ile Tyr Ser Asn Asn Gln Arg Pro Ser Gly Val Pro Asp
                610                 615                 620
Arg Phe Ser Gly Ser Lys Ser Gly Thr Ser Ala Ser Leu Ala Ile Ser
625                 630                 635                 640
Gly Leu Arg Ser Glu Asp Glu Ala Asp Tyr Tyr Cys Ala Ala Trp Asp
                645                 650                 655
```

-continued

Asp Ser Leu Ser Gly Pro Pro Cys Val Phe Gly Gly Thr Lys Leu
         660             665             670

Thr Val Leu Gly Glu Gln Lys Leu Ile Ser Glu Glu Asp Leu Ser Gly
         675             680             685

Ser Ala Ala Ala
         690

<210> SEQ ID NO 69
<211> LENGTH: 675
<212> TYPE: PRT
<213> ORGANISM: Artificial Sequence
<220> FEATURE:
<223> OTHER INFORMATION: Fusion protein

<400> SEQUENCE: 69

Met Gly Ser Ser Gly His His His His His Met Glu Val Gln Leu
1               5                   10                  15

Leu Glu Ser Gly Gly Gly Leu Val Gln Pro Gly Gly Ser Leu Arg Leu
            20                  25                  30

Ser Cys Ala Ala Ser Gly Phe Thr Phe Ser Ser Tyr Glu Met Asn Trp
        35                  40                  45

Val Arg Gln Ala Pro Gly Lys Gly Leu Glu Trp Val Ser Gly Ile Ser
    50                  55                  60

Gly Ser Gly Gly Phe Thr Tyr Tyr Ala Asp Ser Val Lys Gly Arg Phe
65                  70                  75                  80

Thr Ile Ser Arg Asp Asn Ser Lys Asn Thr Leu Tyr Leu Gln Met Asn
                85                  90                  95

Ser Leu Arg Ala Glu Asp Thr Ala Met Tyr Tyr Cys Ala Arg Glu Gly
            100                 105                 110

Tyr Gln Asp Ala Phe Asp Ile Trp Gly Gln Gly Thr Leu Val Thr Val
        115                 120                 125

Ser Ser Gly Gly Gly Gly Ser Gly Gly Gly Ser Gly Gly Gly Gly
    130                 135                 140

Ser Gln Ser Val Leu Thr Gln Pro Pro Ser Ala Ser Gly Thr Pro Gly
145                 150                 155                 160

Gln Arg Val Thr Ile Ser Cys Thr Gly Ser Ser Ser Asn Ile Gly Ala
                165                 170                 175

Gly Tyr Asp Val His Trp Tyr Gln Gln Leu Pro Gly Thr Ala Pro Lys
            180                 185                 190

Leu Leu Ile Tyr Ser Asn Asn Gln Arg Pro Ser Gly Val Pro Asp Arg
        195                 200                 205

Phe Ser Gly Ser Lys Ser Gly Thr Ser Ala Ser Leu Ala Ile Ser Gly
    210                 215                 220

Leu Arg Ser Glu Asp Glu Ala Asp Tyr Tyr Cys Ala Ala Trp Asp Asp
225                 230                 235                 240

Ser Leu Ser Gly Pro Pro Cys Val Phe Gly Gly Thr Lys Leu Thr
                245                 250                 255

Val Leu Gly Glu Gln Lys Leu Ile Ser Glu Glu Asp Leu Ser Gly Ser
            260                 265                 270

Ala Ala Ala Ser His Thr Thr Pro Trp Thr Asn Pro Gly Leu Ala Glu
        275                 280                 285

Asn Phe Met Asn Ser Phe Met Gln Gly Leu Ser Ser Met Pro Gly Phe
    290                 295                 300

Thr Ala Ser Gln Leu Asp Asp Met Ser Thr Ile Ala Gln Ser Met Val
305                 310                 315                 320

-continued

```
Gln Ser Ile Gln Ser Leu Ala Ala Gln Gly Arg Thr Ser Pro Asn Lys
                325                 330                 335
Leu Gln Ala Leu Asn Met Ala Phe Ala Ser Ser Met Ala Glu Ile Ala
            340                 345                 350
Ala Ser Glu Glu Gly Gly Ser Leu Ser Thr Lys Thr Ser Ser Ile
            355                 360                 365
Ala Ser Ala Met Ser Asn Ala Phe Leu Gln Thr Thr Gly Val Val Asn
            370                 375                 380
Gln Pro Phe Ile Asn Glu Ile Thr Gln Leu Val Ser Met Phe Ala Gln
385                 390                 395                 400
Ala Gly Met Asn Asp Gly Gly Thr Pro Trp Thr Asn Pro Gly Leu
                405                 410                 415
Ala Glu Asn Phe Met Asn Ser Phe Met Gln Gly Leu Ser Ser Met Pro
            420                 425                 430
Gly Phe Thr Ala Ser Gln Leu Asp Asp Met Ser Thr Ile Ala Gln Ser
            435                 440                 445
Met Val Gln Ser Ile Gln Ser Leu Ala Ala Gln Gly Arg Thr Ser Pro
    450                 455                 460
Asn Lys Leu Gln Ala Leu Asn Met Ala Phe Ala Ser Ser Met Ala Glu
465                 470                 475                 480
Ile Ala Ala Ser Glu Glu Gly Gly Ser Leu Ser Thr Lys Thr Ser
                485                 490                 495
Ser Ile Ala Ser Ala Met Ser Asn Ala Phe Leu Gln Thr Thr Gly Val
            500                 505                 510
Val Asn Gln Pro Phe Ile Asn Glu Ile Thr Gln Leu Val Ser Met Phe
            515                 520                 525
Ala Gln Ala Gly Met Asn Asp Val Ser Ala Leu Glu Ala Leu Phe Gln
            530                 535                 540
Gly Pro Asn Ser Gly Asn Ser Gly Ile Gln Gly Tyr Gly Gln Ser Ser
545                 550                 555                 560
Ala Ser Ala Ser Ala Ala Ser Ala Ala Ser Thr Val Ala Asn Ser
            565                 570                 575
Val Ser Arg Leu Ser Ser Pro Ser Ala Val Ser Arg Val Ser Ser Ala
            580                 585                 590
Val Ser Ser Leu Val Ser Asn Gly Gln Val Asn Met Ala Ala Leu Pro
            595                 600                 605
Asn Ile Ile Ser Asn Ile Ser Ser Val Ser Ala Ser Ala Pro Gly
610                 615                 620
Ala Ser Gly Cys Glu Val Ile Val Gln Ala Leu Leu Glu Val Ile Thr
625                 630                 635                 640
Ala Leu Val Gln Ile Val Ser Ser Ser Val Gly Tyr Ile Asn Pro
                645                 650                 655
Ser Ala Val Asn Gln Ile Thr Asn Val Val Ala Asn Ala Met Ala Gln
            660                 665                 670
Val Met Gly
    675
```

<210> SEQ ID NO 70
<211> LENGTH: 688
<212> TYPE: PRT
<213> ORGANISM: Artificial Sequence
<220> FEATURE:
<223> OTHER INFORMATION: Fusion protein

<400> SEQUENCE: 70

-continued

```
Met Gly His His His His His Gly Gly Gly Ser Gly Gly Gly
1               5                  10                 15

Gly Ser His His His His His Met Ser His Thr Thr Pro Trp Thr
                20                  25              30

Asn Pro Gly Leu Ala Glu Asn Phe Met Asn Ser Phe Met Gln Gly Leu
            35                  40                  45

Ser Ser Met Pro Gly Phe Thr Ala Ser Gln Leu Asp Asp Met Ser Thr
50                      55                  60

Ile Ala Gln Ser Met Val Gln Ser Ile Gln Ser Leu Ala Ala Gln Gly
65                  70                  75                  80

Arg Thr Ser Pro Asn Lys Leu Gln Ala Leu Asn Met Ala Phe Ala Ser
                85                  90                  95

Ser Met Ala Glu Ile Ala Ala Ser Glu Glu Gly Gly Gly Ser Leu Ser
            100                 105                 110

Thr Lys Thr Ser Ser Ile Ala Ser Ala Met Ser Asn Ala Phe Leu Gln
            115                 120                 125

Thr Thr Gly Val Val Asn Gln Pro Phe Ile Asn Glu Ile Thr Gln Leu
        130                 135                 140

Val Ser Met Phe Ala Gln Ala Gly Met Asn Asp Gly Gly Gly Thr Pro
145                 150                 155                 160

Trp Thr Asn Pro Gly Leu Ala Glu Asn Phe Met Asn Ser Phe Met Gln
            165                 170                 175

Gly Leu Ser Ser Met Pro Gly Phe Thr Ala Ser Gln Leu Asp Asp Met
        180                 185                 190

Ser Thr Ile Ala Gln Ser Met Val Gln Ser Ile Gln Ser Leu Ala Ala
    195                 200                 205

Gln Gly Arg Thr Ser Pro Asn Lys Leu Gln Ala Leu Asn Met Ala Phe
210                 215                 220

Ala Ser Ser Met Ala Glu Ile Ala Ala Ser Glu Glu Gly Gly Gly Ser
225                 230                 235                 240

Leu Ser Thr Lys Thr Ser Ser Ile Ala Ser Ala Met Ser Asn Ala Phe
            245                 250                 255

Leu Gln Thr Thr Gly Val Val Asn Gln Pro Phe Ile Asn Glu Ile Thr
        260                 265                 270

Gln Leu Val Ser Met Phe Ala Gln Ala Gly Met Asn Asp Val Ser Ala
    275                 280                 285

Leu Glu Ala Leu Phe Gln Gly Pro Asn Ser Gly Asn Ser Gly Ile Gln
290                 295                 300

Gly Tyr Gly Gln Ser Ser Ala Ser Ala Ser Ala Ala Ser Ala Ala
305                 310                 315                 320

Ser Thr Val Ala Asn Ser Val Ser Arg Leu Ser Ser Pro Ser Ala Val
                325                 330                 335

Ser Arg Val Ser Ser Ala Val Ser Ser Leu Val Ser Asn Gly Gln Val
            340                 345                 350

Asn Met Ala Ala Leu Pro Asn Ile Ile Ser Asn Ile Ser Ser Ser Val
            355                 360                 365

Ser Ala Ser Ala Pro Gly Ala Ser Gly Cys Glu Val Ile Val Gln Ala
    370                 375                 380

Leu Leu Glu Val Ile Thr Ala Leu Val Gln Ile Val Ser Ser Ser Ser
385                 390                 395                 400

Val Gly Tyr Ile Asn Pro Ser Ala Val Asn Gln Ile Thr Asn Val Val
            405                 410                 415
```

Ala Asn Ala Met Ala Gln Val Met Gly Val Gln Leu Leu Glu Ser
            420                 425                 430

Gly Gly Gly Leu Val Gln Pro Gly Gly Ser Leu Arg Leu Ser Cys Ala
        435                 440                 445

Ala Ser Gly Phe Thr Phe Ser Ser Tyr Glu Met Asn Trp Val Arg Gln
    450                 455                 460

Ala Pro Gly Lys Gly Leu Glu Trp Val Ser Gly Ile Ser Gly Ser Gly
465                 470                 475                 480

Gly Phe Thr Tyr Tyr Ala Asp Ser Val Lys Gly Arg Phe Thr Ile Ser
                485                 490                 495

Arg Asp Asn Ser Lys Asn Thr Leu Tyr Leu Gln Met Asn Ser Leu Arg
            500                 505                 510

Ala Glu Asp Thr Ala Met Tyr Tyr Cys Ala Arg Glu Gly Tyr Gln Asp
        515                 520                 525

Ala Phe Asp Ile Trp Gly Gln Gly Thr Leu Val Thr Val Ser Ser Gly
    530                 535                 540

Gly Gly Gly Ser Gly Gly Gly Gly Ser Gly Gly Gly Gly Ser Gln Ser
545                 550                 555                 560

Val Leu Thr Gln Pro Pro Ser Ala Ser Gly Thr Pro Gly Gln Arg Val
                565                 570                 575

Thr Ile Ser Cys Thr Gly Ser Ser Ser Asn Ile Gly Ala Gly Tyr Asp
            580                 585                 590

Val His Trp Tyr Gln Gln Leu Pro Gly Thr Ala Pro Lys Leu Leu Ile
        595                 600                 605

Tyr Ser Asn Asn Gln Arg Pro Ser Gly Val Pro Asp Arg Phe Ser Gly
    610                 615                 620

Ser Lys Ser Gly Thr Ser Ala Ser Leu Ala Ile Ser Gly Leu Arg Ser
625                 630                 635                 640

Glu Asp Glu Ala Asp Tyr Tyr Cys Ala Ala Trp Asp Ser Leu Ser
                645                 650                 655

Gly Pro Pro Cys Val Phe Gly Gly Gly Thr Lys Leu Thr Val Leu Gly
            660                 665                 670

Glu Gln Lys Leu Ile Ser Glu Glu Asp Leu Ser Gly Ser Ala Ala Ala
        675                 680                 685

<210> SEQ ID NO 71
<211> LENGTH: 1614
<212> TYPE: DNA
<213> ORGANISM: Artificial Sequence
<220> FEATURE:
<223> OTHER INFORMATION: Fusion protein
<220> FEATURE:
<221> NAME/KEY: misc_feature
<222> LOCATION: (37)..(825)
<223> OTHER INFORMATION: scFv1 domain

<400> SEQUENCE: 71
atgggcagca gcggccatca tcatcatcat catatggagg tgcagctgtt ggagtctggg      60
ggaggcttgg tacagcctgg ggggtccctg agactctcct gtgcagcctc tggattcacc     120
ttcagtagtt atgaaatgaa ctgggtccgc caggctccag gaagggggct ggagtgggtc     180
tcaggcatta gtggtagtgg tggtttcaca tactacgcag actccgtgaa gggccgattc     240
accatctcca gagacaattc caagaacacg ctgtatctgc aaatgaacag cctgagagcc     300
gaggacactg ccatgtatta ctgtgcgaga gaggggtacc aggatgcttt tgatatctgg     360
ggccagggta cactggtcac cgtgagcagc ggtggaggcg gttcaggcgg aggtggatcc     420

```
ggcggtggcg atcgcagtc tgtgctgact cagccaccct cagcgtctgg acccccggg      480
cagagggtca ccatctcctg cactgggagc agctccaaca tcggggcagg ttatgatgta     540
cactggtatc agcagctccc aggaacggcc cccaaactcc tcatctatag taataatcag    600
cggccctcag gggtccctga ccgattctct ggctccaagt ctggcacctc agcctccctg    660
gccatcagtg ggctccggtc cgaggatgag gctgattatt actgtgcagc atgggatgac    720
agcctgagtg gtccgccttg ggtgttcggc ggaggaacca agctgaccgt cctaggtgaa    780
caaaaactca tctcagaaga ggatctgtct ggatcagcgg ctgcagggaa ttcaagccat    840
accaccccgt ggaccaaccc gggcctggcg gaaaacttta tgaacagctt tatgcagggc    900
ctgagcagca tgccgggctt taccgcgagc cagctggatg atatgagcac cattgcgcag    960
agcatggtgc agagcattca gagcctggcg gcgcagggcc gcaccagccc gaacaaactg   1020
caggcgctga acatggcgtt tgcgagcagc atggcggaaa ttgcggcgag cgaagaaggc   1080
ggcggcagcc tgagcaccaa accagcagc attgcgagcg cgatgagcaa cgcgtttctg   1140
cagaccaccg gcgtggtgaa ccagccgttt attaacgaaa ttacccagct ggtgagcatg   1200
tttgcgcagg cgggcatgaa cgatgtgagc gcgggcaatt cagggatcca aggttatggt   1260
cagagtagtg cttctgcttc agctgctgcg tcagctgcta gtactgtagc taattcggtg   1320
agtcgcctct catcgccttc cgcagtatct cgagtttctt cagcagtttc tagcttggtt   1380
tcaaatggtc aagtgaatat ggcagcgtta cctaatatca tttccaacat tcttcttct    1440
gtcagtgcat ctgctcctgg tgcttctgga tgtgaggtca tagtgcaagc tctactcgaa    1500
gtcatcactg ctcttgttca aatcgttagt tcttctagtg ttggatatat taatccatct   1560
gctgtgaacc aaattactaa tgttgttgct aatgccatgg ctcaagtaat gggc          1614
```

```
<210> SEQ ID NO 72
<211> LENGTH: 538
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (13)..(275)
<223> OTHER INFORMATION: scFv1 domain

<400> SEQUENCE: 72

Met Gly Ser Ser Gly His His His His His His Met Glu Val Gln Leu
1               5                   10                  15

Leu Glu Ser Gly Gly Gly Leu Val Gln Pro Gly Gly Ser Leu Arg Leu
            20                  25                  30

Ser Cys Ala Ala Ser Gly Phe Thr Phe Ser Ser Tyr Glu Met Asn Trp
        35                  40                  45

Val Arg Gln Ala Pro Gly Lys Gly Leu Glu Trp Val Ser Gly Ile Ser
    50                  55                  60

Gly Ser Gly Gly Phe Thr Tyr Tyr Ala Asp Ser Val Lys Gly Arg Phe
65                  70                  75                  80

Thr Ile Ser Arg Asp Asn Ser Lys Asn Thr Leu Tyr Leu Gln Met Asn
                85                  90                  95

Ser Leu Arg Ala Glu Asp Thr Ala Met Tyr Tyr Cys Ala Arg Glu Gly
            100                 105                 110

Tyr Gln Asp Ala Phe Asp Ile Trp Gly Gln Gly Thr Leu Val Thr Val
        115                 120                 125

Ser Ser Gly Gly Gly Gly Ser Gly Gly Gly Gly Ser Gly Gly Gly Gly
```

```
        130             135             140
Ser Gln Ser Val Leu Thr Gln Pro Pro Ser Ala Ser Gly Thr Pro Gly
145                 150                 155                 160

Gln Arg Val Thr Ile Ser Cys Thr Gly Ser Ser Ser Asn Ile Gly Ala
                165                 170                 175

Gly Tyr Asp Val His Trp Tyr Gln Gln Leu Pro Gly Thr Ala Pro Lys
            180                 185                 190

Leu Leu Ile Tyr Ser Asn Asn Gln Arg Pro Ser Gly Val Pro Asp Arg
        195                 200                 205

Phe Ser Gly Ser Lys Ser Gly Thr Ser Ala Ser Leu Ala Ile Ser Gly
    210                 215                 220

Leu Arg Ser Glu Asp Glu Ala Asp Tyr Tyr Cys Ala Ala Trp Asp Asp
225                 230                 235                 240

Ser Leu Ser Gly Pro Pro Trp Val Phe Gly Gly Gly Thr Lys Leu Thr
                245                 250                 255

Val Leu Gly Glu Gln Lys Leu Ile Ser Glu Glu Asp Leu Ser Gly Ser
            260                 265                 270

Ala Ala Ala Gly Asn Ser Ser His Thr Thr Pro Trp Thr Asn Pro Gly
        275                 280                 285

Leu Ala Glu Asn Phe Met Asn Ser Phe Met Gln Gly Leu Ser Ser Met
    290                 295                 300

Pro Gly Phe Thr Ala Ser Gln Leu Asp Asp Met Ser Thr Ile Ala Gln
305                 310                 315                 320

Ser Met Val Gln Ser Ile Gln Ser Leu Ala Ala Gln Gly Arg Thr Ser
                325                 330                 335

Pro Asn Lys Leu Gln Ala Leu Asn Met Ala Phe Ala Ser Ser Met Ala
            340                 345                 350

Glu Ile Ala Ala Ser Glu Glu Gly Gly Gly Ser Leu Ser Thr Lys Thr
        355                 360                 365

Ser Ser Ile Ala Ser Ala Met Ser Asn Ala Phe Leu Gln Thr Thr Gly
    370                 375                 380

Val Val Asn Gln Pro Phe Ile Asn Glu Ile Thr Gln Leu Val Ser Met
385                 390                 395                 400

Phe Ala Gln Ala Gly Met Asn Asp Val Ser Ala Gly Asn Ser Gly Ile
                405                 410                 415

Gln Gly Tyr Gly Gln Ser Ser Ala Ser Ala Ser Ala Ala Ala Ser Ala
            420                 425                 430

Ala Ser Thr Val Ala Asn Ser Val Ser Arg Leu Ser Ser Pro Ser Ala
        435                 440                 445

Val Ser Arg Val Ser Ser Ala Val Ser Leu Val Ser Asn Gly Gln
    450                 455                 460

Val Asn Met Ala Ala Leu Pro Asn Ile Ile Ser Asn Ile Ser Ser Ser
465                 470                 475                 480

Val Ser Ala Ser Ala Pro Gly Ala Ser Gly Cys Glu Val Ile Val Gln
                485                 490                 495

Ala Leu Leu Glu Val Ile Thr Ala Leu Val Gln Ile Val Ser Ser Ser
            500                 505                 510

Ser Val Gly Tyr Ile Asn Pro Ser Ala Val Asn Gln Ile Thr Asn Val
        515                 520                 525

Val Ala Asn Ala Met Ala Gln Val Met Gly
    530                 535

<210> SEQ ID NO 73
```

```
<211> LENGTH: 1197
<212> TYPE: DNA
<213> ORGANISM: Artificial Sequence
<220> FEATURE:
<223> OTHER INFORMATION: Fusion protein
<220> FEATURE:
<221> NAME/KEY: misc_feature
<222> LOCATION: (28)..(816)
<223> OTHER INFORMATION: scFv1 domain

<400> SEQUENCE: 73
atgggccatc atcatcatca tcatatggag gtgcagctgt tggagtctgg gggaggcttg      60
gtacagcctg gggggtccct gagactctcc tgtgcagcct ctggattcac cttcagtagt     120
tatgaaatga actgggtccg ccaggctcca gggaaggggc tggagtgggt ctcaggcatt     180
agtggtagtg gtggtttcac atactacgca gactccgtga agggccgatt caccatctcc     240
agagacaatt ccaagaacac gctgtatctg caaatgaaca gcctgagagc cgaggacact     300
gccatgtatt actgtgcgag agaggggtac caggatgctt ttgatatctg gggccagggt     360
acactggtca ccgtgagcag cggtggaggc ggttcaggcg gaggtggatc cggcggtggc     420
ggatcgcagt ctgtgctgac tcagccaccc tcagcgtctg gaccccccgg gcagagggtc     480
accatctcct gcactgggag cagctccaac atcgggcag gttatgatgt acactggtat     540
cagcagctcc caggaacggc ccccaaactc ctcatctata gtaataatca gcggccctca     600
ggggtccctg accgattctc tggctccaag tctggcacct cagcctccct ggccatcagt     660
gggctccggt ccgaggatga ggctgattat tactgtgcag catgggatga cagcctgagt     720
ggtccgcctt gggtgttcgg cggaggaacc aagctgacgg tcctaggtga acaaaaactc     780
atctcagaag aggatctgtc tggatcagcg gctgcaggga attcagggat ccaaggttat     840
ggtcagagta gtgcttctgc ttcagctgct gcgtcagctg ctagtactgt agctaattcg     900
gtgagtcgcc tctcatcgcc ttccgcagta tctcgagttt cttcagcagt ttctagcttg     960
gtttcaaatg gtcaagtgaa tatggcagcg ttacctaata tcatttccaa catttcttct    1020
tctgtcagtg catctgctcc tggtgcttct ggatgtgagg tcatagtgca agctctactc    1080
gaagtcatca ctgctcttgt tcaaatcgtt agttcttcta gtgttggata tattaatcca    1140
tctgctgtga accaaattac taatgttgtt gctaatgcca tggctcaagt aatgggc       1197

<210> SEQ ID NO 74
<211> LENGTH: 399
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (10)..(272)
<223> OTHER INFORMATION: scFv1 domain

<400> SEQUENCE: 74

Met Gly His His His His His His Met Glu Val Gln Leu Leu Glu Ser
1               5                   10                  15

Gly Gly Gly Leu Val Gln Pro Gly Gly Ser Leu Arg Leu Ser Cys Ala
            20                  25                  30

Ala Ser Gly Phe Thr Phe Ser Ser Tyr Glu Met Asn Trp Val Arg Gln
        35                  40                  45

Ala Pro Gly Lys Gly Leu Glu Trp Val Ser Gly Ile Ser Gly Ser Gly
    50                  55                  60

Gly Phe Thr Tyr Tyr Ala Asp Ser Val Lys Gly Arg Phe Thr Ile Ser
```

-continued

```
             65                  70                  75                  80
Arg Asp Asn Ser Lys Asn Thr Leu Tyr Leu Gln Met Asn Ser Leu Arg
                 85                  90                  95

Ala Glu Asp Thr Ala Met Tyr Tyr Cys Ala Arg Glu Gly Tyr Gln Asp
                100                 105                 110

Ala Phe Asp Ile Trp Gly Gln Gly Thr Leu Val Thr Val Ser Ser Gly
                115                 120                 125

Gly Gly Gly Ser Gly Gly Gly Ser Gly Gly Gly Gly Ser Gln Ser
            130                 135                 140

Val Leu Thr Gln Pro Pro Ser Ala Ser Gly Thr Pro Gly Gln Arg Val
145                 150                 155                 160

Thr Ile Ser Cys Thr Gly Ser Ser Asn Ile Gly Ala Gly Tyr Asp
                165                 170                 175

Val His Trp Tyr Gln Gln Leu Pro Gly Thr Ala Pro Lys Leu Leu Ile
                180                 185                 190

Tyr Ser Asn Asn Gln Arg Pro Ser Gly Val Pro Asp Arg Phe Ser Gly
                195                 200                 205

Ser Lys Ser Gly Thr Ser Ala Ser Leu Ala Ile Ser Gly Leu Arg Ser
        210                 215                 220

Glu Asp Glu Ala Asp Tyr Tyr Cys Ala Ala Trp Asp Asp Ser Leu Ser
225                 230                 235                 240

Gly Pro Pro Trp Val Phe Gly Gly Gly Thr Lys Leu Thr Val Leu Gly
                245                 250                 255

Glu Gln Lys Leu Ile Ser Glu Glu Asp Leu Ser Gly Ser Ala Ala Ala
                260                 265                 270

Gly Asn Ser Gly Ile Gln Gly Tyr Gly Gln Ser Ser Ala Ser Ala Ser
            275                 280                 285

Ala Ala Ala Ser Ala Ala Ser Thr Val Ala Asn Ser Val Ser Arg Leu
            290                 295                 300

Ser Ser Pro Ser Ala Val Ser Arg Val Ser Ser Ala Val Ser Ser Leu
305                 310                 315                 320

Val Ser Asn Gly Gln Val Asn Met Ala Ala Leu Pro Asn Ile Ile Ser
                325                 330                 335

Asn Ile Ser Ser Ser Val Ser Ala Ser Ala Pro Gly Ala Ser Gly Cys
                340                 345                 350

Glu Val Ile Val Gln Ala Leu Leu Glu Val Ile Thr Ala Leu Val Gln
            355                 360                 365

Ile Val Ser Ser Ser Ser Val Gly Tyr Ile Asn Pro Ser Ala Val Asn
        370                 375                 380

Gln Ile Thr Asn Val Val Ala Asn Ala Met Ala Gln Val Met Gly
385                 390                 395
```

US 9,856,308 B2

SPIDER SILK FUSION PROTEIN STRUCTURES INCORPORATING IMMUNOGLOBULIN FRAGMENTS AS AFFINITY LIGANDS

TECHNICAL FIELD OF THE INVENTION

The present invention relates to the field of recombinant fusion proteins, and more specifically to novel fusion proteins comprising moieties derived from spider silk proteins (spidroins). The present invention provides methods for providing a protein structure which is a polymer comprising a recombinant fusion protein, which is comprising moieties derived from spidroins. There is also provided novel protein structures for binding to an organic target.

BACKGROUND TO THE INVENTION

In applied protein chemistry, it is a common problem how to formulate or present a biologically active peptide or protein to the relevant site of activity, typically an organic target, such as a nucleic acid, a protein, a complex of proteins, or a complex of a protein(s) and/or lipids and/or carbohydrates and/or a nucleic acid(s). The simplest solution is simply to provide an aqueous solution of the biologically active peptide or protein. Many applications do however require some further means to achieve the desired goal. For instance, the peptides/proteins may be associated with a lipid mixture or chemically immobilized to a support structure.

Applications for peptides/proteins immobilized to a support structure include preparative and analytical separation procedures, such as bioprocesses, chromatography, cell capture and culture, active filters, and diagnostics. Structures based on extracellular matrix proteins, e.g. collagen, are disclosed in EP 704 532 and EP 985 732.

It has also been suggested to use spider silk proteins in a supporting structure. Spider silks are nature's high-performance polymers, obtaining extraordinary toughness and extensibility due to a combination of strength and elasticity. Spiders have up to seven different glands which produce a variety of silk types with different mechanical properties and functions. Dragline silk, produced by the major ampullate gland, is the toughest fiber. It consists of two main polypeptides, mostly referred to as major ampullate spidroin (MaSp) 1 and 2, but e.g. as ADF-3 and ADF-4 in *Araneus diadematus*. These proteins have molecular masses in the range of 200-720 kDa. Spider dragline silk proteins, or MaSps, have a tripartite composition; a non-repetitive N-terminal domain, a central repetitive region comprised of many iterated poly-Ala/Gly segments, and a non-repetitive C-terminal domain. It is generally believed that the repetitive region forms intermolecular contacts in the silk fibers, while the precise functions of the terminal domains are less clear. It is also believed that in association with fiber formation, the repetitive region undergoes a structural conversion from random coil and α-helical conformation to β-sheet structure. The C-terminal region of spidroins is generally conserved between spider species and silk types.

WO 07/078239 and Stark, M. et al., Biomacromolecules 8: 1695-1701, (2007) disclose a miniature spider silk protein consisting of a repetitive fragment with a high content of Ala and Gly and a C-terminal fragment of a protein, as well as soluble fusion proteins comprising the spider silk protein. Fibers of the spider silk protein are obtained spontaneously upon liberation of the spider silk protein from its fusion partner.

Rising, A. et al., CMLS 68(2): 169-184 (2010) reviews advances in the production of spider silk proteins.

US 2009/0263430 discloses chemical coupling of the enzyme β-galactosidase to films of a miniature spider silk protein. However, chemical coupling may require conditions which are unfavourable for protein stability and/or function. Proteins containing multiple repeats of a segment derived from the repetitive region of spider silk proteins have been designed to include a RGD cell-binding segment (Bini, E et al., Biomacromolecules 7:3139-3145 (2006)) and/or a R5 peptide (Wong Po Foo, C et al., Proc Natl Acad Sci 103 (25): 9428-9433 (2006)) or other protein segments involved in mineralization (Huang, J et al., Biomaterials 28: 2358-2367 (2007); WO 2006/076711). In these prior art documents, films are formed by solubilizing the fusion proteins in the denaturing organic solvent hexafluoroisopropanol (HFIP) and drying.

US 2005/261479 A1 discloses a method of for purification of recombinant silk proteins consisting of a repetitive fragment and an affinity tag, involving magnetic affinity separation of individual silk proteins from complex mixtures without formation of silk protein fibers or other polymer structures.

Known supporting structures and associated techniques have certain drawbacks with regard to e.g. economy, efficiency, stability, regenerating capacity, bioactivity and biocompatibility.

SUMMARY OF THE INVENTION

It is an object of the present invention to provide novel recombinant fusion proteins which are capable of selective interaction with an organic target.

It is an object of the present invention to provide a novel protein structure that is capable of selective interaction with an organic target.

It is also an object of the present invention to provide a protein structure that is capable of selective interaction with an organic target, wherein the structure is formed without use of harsh solvents which may have an unpredictable effect on the secondary structure or activity of the protein and/or remain in the protein structure.

It is one object of the present invention to provide a stable protein structure that is capable of selective interaction with an organic target, which protein structure can readily be regenerated after use, e.g. with chemical treatment.

It is another object of the present invention to provide a stable protein structure that is biocompatible and suitable for cell culture and as an implant.

It is yet another object of the invention to provide a protein structure with a high density of evenly spaced functionalities that are capable of selective interaction with an organic target.

It is a further object of the invention to provide a protein structure which maintains its selective binding ability upon storage at +4° C. or at room temperature for months.

It is also an object of the invention to provide a protein structure which is autoclavable, i.e. maintains its selective binding ability after sterilizing heat treatment.

It is a further object of the present invention to provide a protein structure that is useful in protein microarray diagnostics.

For these and other objects that will be evident from the following disclosure, the present invention provides according to a first aspect a fusion protein and a protein structure consisting of polymers comprising as a repeating structural unit the fusion protein as set out in the claims.

According to a related aspect, the present invention provides an isolated nucleic acid encoding the fusion protein and a method of producing the fusion protein as set out in the claims.

The present invention provides according to another aspect a method for providing a protein structure as set out in the claims.

The present invention provides according to a further aspect an affinity medium as set out in the claims.

The present invention provides according to one aspect a cell scaffold material as set out in the claims. According to a related aspect, the present invention also provides a combination of cells and a cell scaffold material according to the claims.

The present invention provides according to an aspect novel uses of a protein structure and a fusion protein as set out in the claims.

The present invention provides according to another aspect a method for separation of an organic target from a sample as set out in the claims.

The present invention provides according to a further aspect a method for immobilization and optionally cultivation of cells as set out in the claims.

BRIEF DESCRIPTION OF THE DRAWINGS

FIG. 1 shows a sequence alignment of spidroin C-terminal domains.

FIG. 2 shows a sequence alignment of spidroin N-terminal domains.

FIG. 4 shows binding of biotinylated antigen to a fusion protein according to the invention, detected with Alexa647-labelled streptavidin.

Figure 3:
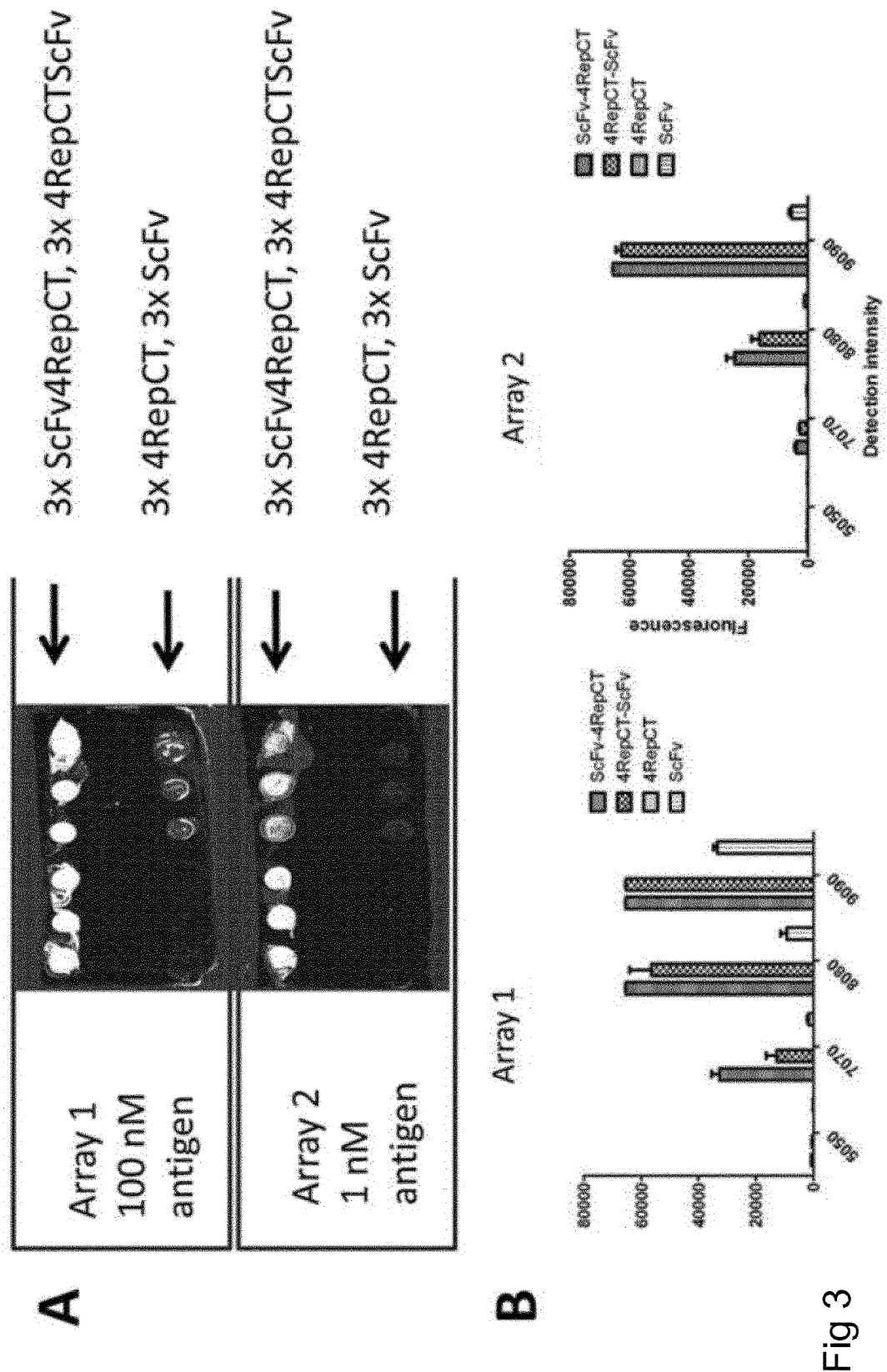
FIG. 3 shows binding of Alexa647-labelled antigen to a fusion protein according to the invention.

| List of appended sequences | |
|---|---|
| SEQ ID NO | |
| 1 | 4Rep |
| 2 | 4RepCT |
| 3 | NT4Rep |
| 4 | NT5Rep |
| 5 | NT4RepCTHis |
| 6 | NT |
| 7 | CT |
| 8 | consensus NT sequence |
| 9 | consensus CT sequence |
| 10 | repetitive sequence from *Euprosthenops australis* MaSp1 |
| 11 | consensus G segment sequence 1 |
| 12 | consensus G segment sequence 2 |
| 13 | consensus G segment sequence 3 |
| 14 | CT *Euprosthenops* sp MaSp1 |
| 15 | CT *Euprosthenops australis* MaSp1 |
| 16 | CT *Argiope trifasciata* MaSp1 |
| 17 | CT *Cyrtophora moluccensis* Sp1 |
| 18 | CT *Latrodectus geometricus* MaSp1 |
| 19 | CT *Latrodectus hesperus* MaSp1 |
| 20 | CT *Macrothele holsti* Sp1 |
| 21 | CT *Nephila clavipes* MaSp1 |
| 22 | CT *Nephila pilipes* MaSp1 |
| 23 | CT *Nephila madagascariensis* MaSp1 |
| 24 | CT *Nephila senegalensis* MaSp1 |
| 25 | CT *Octonoba varans* Sp1 |
| 26 | CT *Psechrus sinensis* Sp1 |

| List of appended sequences | |
|---|---|
| SEQ ID NO | |
| 27 | CT *Tetragnatha kauaiensis* MaSp1 |
| 28 | CT *Tetragnatha versicolor* MaSp1 |
| 29 | CT *Araneus bicentenarius* Sp2 |
| 30 | CT *Argiope amoena* MaSp2 |
| 31 | CT *Argiope aurantia* MaSp2 |
| 32 | CT *Argiope trifasciata* MaSp2 |
| 33 | CT *Gasteracantha mammosa* MaSp2 |
| 34 | CT *Latrodectus geometricus* MaSp2 |
| 35 | CT *Latrodectus hesperus* MaSp2 |
| 36 | CT *Nephila clavipes* MaSp2 |
| 37 | CT *Nephila madagascariensis* MaSp2 |
| 38 | CT *Nephila senegalensis* MaSp2 |
| 39 | CT *Dolomedes tenebrosus* Fb1 |
| 40 | CT *Dolomedes tenebrosus* Fb2 |
| 41 | CT *Araneus diadematus* ADF-1 |
| 42 | CT *Araneus diadematus* ADF-2 |
| 43 | CT *Araneus diadematus* ADF-3 |
| 44 | CT *Araneus diadematus* ADF-4 |
| 45 | NT *Euprosthenops australis* MaSp1 |
| 46 | NT *Latrodectus geometricus* MaSp1 |
| 47 | NT *Latrodectus hesperus* MaSp1 |
| 48 | NT *Nephila clavipes* MaSp1 |
| 49 | NT *Argiope trifasciata* MaSp2 |
| 50 | NT *Latrodectus geometricus* MaSp2 |
| 51 | NT *Latrodectus hesperus* MaSp2 |
| 52 | NT *Nephila inaurata madagascariensis* MaSp2 |
| 53 | NT *Nephila clavipes* MaSp2 |
| 54 | NT *Argiope bruennichi* cylindriform spidroin 1 |
| 55 | NT *Nephila clavata* cylindriform spidroin 1 |
| 56 | NT *Latrodectus hesperus* tubuliform spidroin |
| 57 | NT *Nephila clavipes* flagelliform silk protein |
| 58 | NT *Nephila inaurata madagascariensis* flagelliform silk protein |
| 59 | $His_6ScFvRep_4CT$ (DNA) |
| 60 | $His_6Rep_4CTScFv$ (DNA) |
| 61 | $His_6ScFvRep_4CT$ |
| 62 | $His_6Rep_4CTScFv$ |
| 63 | $His_6ScFvCT$ |
| 64 | $His_6CTScFv$ |
| 65 | $His_6ScFvNT-CT$ |
| 66 | $His_6NT-CTScFv$ |
| 67 | $His_6ScFvNTRep_4CT$ |
| 68 | $His_6NTRep_4CTScFv$ |
| 69 | $His_6ScFvNTNT-CT$ |
| 70 | $His_6NTNT-CTScFv$ |
| 71 | $His_6-scFv1-NTCT$ (DNA) |
| 72 | $His_6-scFv1-NTCT$ |
| 73 | $His_6-scFv1-CT$ (DNA) |
| 74 | $His_6-scFv1-CT$ |

DETAILED DESCRIPTION OF THE INVENTION

The present invention is generally based on the insight that solid protein structures capable of selective interaction with an organic target can be prepared in the form of polymers of a recombinant fusion protein as a repeating structural unit. The fusion protein is comprising at least one immunoglobulin (Ig) fragment that is capable of selective interaction with the organic target (an antigen/epitope), and a moiety corresponding to at least the C-terminal fragment of a spider silk protein. Surprisingly, the moiety derived from the spider silk protein can be induced to rearrange structurally and as a result form polymeric, solid structures, while the moiety comprising the immunoglobulin fragment(s), comprising e.g. a paratope, is not structurally rearranged but maintains its desirable structure and function, i.e. capability of selective interaction with the organic target. The protein structures can be obtained without a chemical coupling step or a denaturing method step, which facilitates the procedure and improves the chances of obtaining a fusion protein with maintained functionality of its moieties, in particular when the functions are dependent on the secondary structure of the moieties. The formation of these fusion protein polymers can be tightly controlled, and this insight has been developed into further novel protein structures, methods of producing the protein structures and uses of the protein structures in various applications and methods.

The fusion protein according to the invention thus harbors both the desired selective interaction activity and an internal solid support activity that is employed in the protein structure under physiological conditions. It must be considered as surprising that the binding activity of the fusion protein is maintained although the moiety comprising the immunoglobulin fragment(s) is covalently attached to the spidroin moiety when the latter is structurally rearranged to form polymeric, solid structures. In fact, the heat and/or chemical stability and/or binding activity of the moiety providing the selective interaction activity may be increased when integrated in a fusion protein structure according to the invention. The protein structure also provides a high and predictable density of the selective interaction activity towards an organic target. Losses of valuable protein moieties with selective interaction activity are minimized, since all expressed protein moieties are associated with the solid support.

The polymers which are formed from the fusion proteins according to the invention are solid structures and are useful for their physical properties, especially the useful combination of high strength, elasticity and light weight. A particularly useful feature is that the spidroin-derived moieties of the fusion protein are biochemically robust and suitable for regeneration, e.g. with acid, base or chaotropic agents, and suitable for heat sterilization, e.g. autoclaving at 120° C. for 20 min. The polymers are also useful for their ability to support cell adherence and growth. The properties derived from dragline silk are attractive in development of new materials for medical or technical purposes. In particular, protein structures according to the invention are useful in preparative and analytical separation procedures, such as chromatography, cell capture, selection and culture, active filters, and diagnostics.

By way of a preferred example, protein structures according to the invention are also useful for immobilizing antibody fragments in protein microarray diagnostics. Among many advantages which are understood from the present disclosure, it is contemplated that the protein structures according to the invention provide an increased sensitivity. Many diseases are today difficult to diagnose and select correct treatment for. In the arena of multiplexed molecular diagnostics, one can demonstrate a trend over time from DNA to mRNA and now to proteins. Because the information content of proteins is far richer than that of nucleic acids, the potential for more refined diagnoses based on protein patterns is the key to solve the more difficult-to-diagnose disease states as well as the personalized medicine needs. In addition, these diagnoses should be more able to reflect temporal changes in disease and health of a patient's status, unattainable by the static view afforded by germinal DNA.

By thorough investigation of changes in protein content of patient samples (e.g. serum) the understanding of disease-associated changes on a molecular level will help elucidating the underlying mechanisms of disease biology. A survey of the disease related molecular profile could serve as a foundation for improved diagnosis, prognosis and classification of patients. Also, it could be a helpful tool for selecting patients eligible for a particular therapy and monitoring the effects of therapeutic interventions. Specific protein domains, such as engineered antibody fragments, e.g. Single chain Fragment Variable (ScFv), are invaluable tools for analysis of the specific protein content within a sample. One of the most challenging tasks is immobilizing the antibody fragments onto surfaces in such a way that their three-dimensional structure, functionality and binding sites are maintained and accessible. Many important disease markers are proteins that are low abundant in easily obtained samples such as serum. In order to achieve highly accurate molecular profiling, one therefore has to increase the sensitivity of current conventional technologies. Herein we describe a new strategy for immobilisation of antibody fragments onto a protein-based environment made of recombinant spider silk. This mild immobilisation technique help to keep the antibody fragment stable and hinder denaturation, and thereby increases the sensitivity to specific proteins in a patient sample.

Spider silk has very attractive physical and physiological properties. The recombinant miniature spider silk protein $Rep_4CT$ can be produced in *Escherichia coli* and purified under non-denaturing conditions. The pure $Rep_4CT$ can be further processed into various solid structures, or formats, such as fibers, transparent films and three-dimensional porous foams. Other protein domains can be produced in fusion with CT or $Rep_4CT$, and thereafter processed into solid formats that are functionalized with specific protein functions. In this way, antibody fragments can be covalently linked to CT or $Rep_4CT$, and thereafter processed into small, yet strong, spots that are functionalised with antigen binding functions. These silk-immobilised antibody fragments can also be spotted onto a microarray chip surface, and used to detect disease molecules in a body sample, e.g. serum.

Using this strategy the antibody fragments are contained in a protein-based environment and the major fraction of antibody fragments will be in its active form. The new strategy can be compared to the conventional direct drying of antibody fragments onto a surface, where a larger fraction of fragments will be randomly orientated and denatured and, hence, not able to bind antigen. Moreover, when linked to the spider silk, the antibody fragment will be oriented with the antigen binding site towards the molecules in the solution. Since the sensitivity is coupled to the number of active antibody fragments, the higher the fraction of available and active antibody fragments, the higher the sensitivity.

Protein structures according to the invention are also useful in medical devices, such as implants and medical products, such as wound closure systems, band-aids, sutures, wound dressings, and scaffolds for cell immobilization, cell culture, tissue engineering and guided cell regeneration.

The present invention provides a recombinant fusion protein that is capable of selective interaction with an organic target, which fusion protein is comprising the moieties B and CT, and optionally REP and/or NT. The present invention also provides a protein structure that is capable of selective interaction with an organic target, wherein said protein structure is a polymer comprising, and optionally consisting of, the recombinant fusion protein according to the invention, i.e. comprising, and optionally consisting of, the moieties B and CT, and optionally REP and/or NT.

Although the CT, REP and NT moieties of the fusion proteins in the examples by necessity relate to specific proteins, e.g. proteins derived from major spidroin 1 (MaSp1) from *Euprosthenops australis*, it is considered that the present disclosure is applicable to any structurally similar moieties for the purpose of producing fusion protein structures according to the invention. Furthermore, although the B moiety which provides the selective interaction activity of the fusion proteins in the examples by necessity relate to specific protein moieties, e.g. moieties derived from immunoglobulins, it is considered that the present disclosure is applicable to any structurally and/or functionally similar B moiety for the purpose of producing fusion protein structures according to the invention, capable of selective interaction with an organic target.

Specific fusion proteins according to the invention are defined by the formulas $B_x$-CT-$B_z$, $B_x$-REP-$B_y$-CT-$B_z$ and $B_x$-CT-$B_y$-REP-$B_z$, wherein x, y and z are integers from 0 to 5; and $x+y+z\geq 1$, optionally further containing one NT moiety at either end of the fusion protein or between any two protein moieties in the fusion protein. If $x+y+z>1$, i.e. if there are two or more B moieties, they may be identical or different. The two or more B moieties may have capacity of selective interaction with the same organic target or with different organic targets. It is preferred that the two or more B moieties are substantially identical, each having capacity of selective interaction with the same organic target. Alternatively, it is preferred that the two or more B moieties are not identical, and that they together provide the capacity of selective interaction with the organic target.

In preferred fusion proteins according to the invention, x, y and z are integers from 0 to 2, preferably from 0 to 1. In certain preferred fusion proteins according to the invention, y=0. In more preferred specific fusion proteins according to the invention, y=0 and either x or z are 0, i.e. the fusion proteins are defined by the formulas $B_x$-CT, CT-$B_E$, $B_x$-REP-CT, $B_x$-CT-REP, REP-CT-$B_z$ and CT-REP-$B_z$, wherein x and z are integers from 1 to 5. In preferred fusion proteins according to the invention, y=0, x and z are integers from 0 to 1; and x+z=1. Thus, certain preferred fusion proteins according to the invention are defined by the formulas B-CT, CT-B, B-REP-CT, B-CT-REP, REP-CT-B and CT-REP-B. In preferred fusion proteins according to the invention, the optional REP moiety is missing. In fusion proteins lacking a REP moiety, non-specific binding of the B moiety to other molecules than its antigen target has advantageously been observed to decrease. It is particularly surprising that solid structures are formed spontaneously from fusion proteins lacking a REP moiety. In further preferred fusion proteins according to the invention, the optional NT moiety is missing.

The term "fusion protein" implies here a protein that is made by expression from a recombinant nucleic acid, i.e. DNA or RNA that is created artificially by combining two or more nucleic acid sequences that would not normally occur together (genetic engineering). The fusion proteins according to the invention are recombinant proteins, and they are therefore not identical to naturally occurring proteins. In particular, wildtype spidroins are not fusion proteins according to the invention, because they are not expressed from a recombinant nucleic acid as set out above. The combined nucleic acid sequences encode different proteins, partial proteins or polypeptides with certain functional properties. The resulting fusion protein, or recombinant fusion protein, is a single protein with functional properties derived from each of the original proteins, partial proteins or polypeptides. Furthermore, the fusion protein according to the invention and the corresponding genes are chimeric, i.e. the protein/gene moieties are derived from at least two different species. The CT moiety, as well as the optional REP and NT moiety, are all derived from a spider silk protein. For avoidance of doubt, the B moiety according to the invention is a non-spidroin protein or polypeptide, i.e. it is not derived from a spider silk protein. In particular, the B moiety according to the invention is not derived from the C-terminal, repetitive or N-terminal fragments of a spider silk protein.

The fusion protein typically consists of from 170 to 2000 amino acid residues, such as from 170 to 1000 amino acid residues, such as from 170 to 600 amino acid residues, preferably from 170 to 500 amino acid residues, such as from 170 to 400 amino acid residues. The small size is advantageous because longer proteins containing spider silk protein fragments may form amorphous aggregates, which require use of harsh solvents for solubilisation and polymerisation. The recombinant fusion protein may contain more than 2000 residues, in particular in cases where the spider silk protein more than one B moiety and/or when it contains a NT moiety, e.g. 1-2 NT moieties.

The terms "spidroins" and "spider silk proteins" are used interchangeably throughout the description and encompass all known spider silk proteins, including major ampullate spider silk proteins which typically are abbreviated "MaSp", or "ADF" in the case of *Araneus diadematus*. These major ampullate spider silk proteins are generally of two types, 1 and 2. These terms furthermore include non-natural proteins with a high degree of identity and/or similarity to the known spider silk proteins.

Consequently, the term "non-spidroin" implies proteins that are not derived from a spider silk protein, i.e. with a low (or no) degree of identity and/or similarity to spider silk proteins.

The protein structure according to the invention is capable of selective interaction with an organic target. This capacity resides in the fusion protein according to the invention, and more specifically in the B moiety of the fusion protein. Any interactions of the CT moiety, as well as the optional REP and NT moiety, with organic molecules are not encompassed by the term "capable of selective interaction with an organic target". For avoidance of doubt, the term "capable of selective interaction with an organic target" does not encompass dimerization, oligomerization or polymerization of the fusion proteins according to the invention that rely on interactions involving the CT moiety, as well as the optional REP and NT moieties.

The term "organic target" encompasses all chemical molecules containing carbon with the exception of what is traditionally considered inorganic molecules by the skilled person, e.g. carbonates, simple oxides of carbon, cyanides, diamond and graphite. For avoidance of doubt, inorganic molecules, salts and ions, such as silica and calcium chloride, are not organic. The organic target may be a complex containing or consisting of organic molecules, e.g. a receptor complex on a cell surface. The organic target may be a monomer, dimer, oligomer or polymer of one or more organic molecule types, which may be held together by covalent bonds or other types of association. It may of course also simply be a single organic molecule. Preferred organic targets according to the invention include, but are not limited to, nucleic acids, proteins and polypeptides, lipids and carbohydrates, as well as combinations thereof. Further preferred organic targets according to the invention include, but are not limited to, immunoglobulins, molecules comprising immunoglobulin or derivatives thereof, albumin, molecules comprising albumin or derivatives thereof, biotin, molecules comprising biotin or derivatives or analogues thereof, and biological disease markers, e.g. from blood, serum, urine, saliva or other samples from body tissues.

In the context of the present invention, "specific" or "selective" interaction of a ligand, e.g. a B moiety of the fusion protein according to the invention with its target means that the interaction is such that a distinction between specific and non-specific, or between selective and non-selective, interaction becomes meaningful. The interaction between two proteins is sometimes measured by the dissociation constant. The dissociation constant describes the strength of binding (or affinity) between two molecules. Typically the dissociation constant between an antibody and its antigen (epitope) is from $10^{-7}$ to $10^{-11}$ M. However, high specificity does not necessarily require high affinity. Molecules with low affinity (in the molar range) for its counterpart have been shown to be as specific as molecules with much higher affinity. In the case of the present invention, a specific or selective interaction refers to the extent to which a particular method can be used to determine the presence and/or amount of a specific protein, the target protein or a fragment thereof, under given conditions in the presence of other proteins in a sample of a naturally occurring or processed biological or biochemical fluid. In other words, specificity or selectivity is the capacity to distinguish between related proteins. Specific and selective are sometimes used interchangeably in the present description.

The fusion protein according to the invention may also contain one or more linker peptides. The linker peptide(s) may be arranged between any moieties of the fusion protein, e.g. between two B moieties, between B and CT moieties, between CT and REP moieties, and between B and REP moieties, or may be arranged at either terminal end of the fusion protein. If the B moiety contains two or more Ig fragments, the linker peptide(s) may also be arranged in between two Ig fragments. If the fusion protein contains two or more B moieties, the linker peptide(s) may also be arranged in between two B moieties. The linker(s) may provide a spacer between the functional units of the fusion protein, but may also constitute a handle for identification and purification of the fusion protein, e.g. a His and/or a Trx tag. If the fusion protein contains two or more linker peptides for identification and purification of the fusion protein, it is preferred that they are separated by a spacer sequence, e.g. $His_6$-spacer-$His_6$-. The linker may also constitute a signal peptide, such as a signal recognition particle, which directs the fusion protein to the membrane and/or causes secretion of the fusion protein from the host cell into the surrounding medium. The fusion protein may also include a cleavage site in its amino acid sequence, which allows for cleavage and removal of the linker(s) and/or other relevant moieties, typically the B moiety or moieties. Various cleavage sites are known to the person skilled in the art, e.g. cleavage sites for chemical agents, such as CNBr after Met residues and hydroxylamine between Asn-Gly residues, cleavage sites for proteases, such as thrombin or protease 3C, and self-splicing sequences, such as intein self-splicing sequences.

The CT and B are linked directly or indirectly to one another. A direct linkage implies a direct covalent binding between the moieties without intervening sequences, such as linkers. An indirect linkage also implies that the moieties are linked by covalent bonds, but that there are intervening sequences, such as linkers and/or one or more further moieties, e.g. a REP and/or a NT moiety.

The B moiety or moieties may be arranged internally or at either end of the fusion protein, i.e. C-terminally arranged or N-terminally arranged. It is preferred that the B moiety or moieties are arranged at the N-terminal end of the fusion protein. If the fusion protein contains one or more linker peptide(s) for identification and purification of the fusion protein, e.g. a His or Trx tag(s), it is preferred that it is arranged at the N-terminal end of the fusion protein.

A preferred fusion protein has the form of an N-terminally arranged B moiety, coupled by a linker peptide of 1-30 amino acid residues, such as 1-10 amino acid residues, to C-terminally arranged REP and CT moieties. The linker peptide may contain a cleavage site. Optionally, the fusion protein has an N-terminal or C-terminal linker peptide, which may contain a purification tag, such as a His tag, and a cleavage site.

Another preferred fusion protein has the form of an N-terminally arranged B moiety coupled directly to C-terminally arranged REP and CT moieties. Optionally, the fusion protein has an N-terminal or C-terminal linker peptide, which may contain a purification tag, such as a His tag, and a cleavage site.

The protein structure according to the invention is a polymer comprising as a repeating structural unit recombinant fusion proteins according to the invention, which implies that it contains an ordered plurality of fusion proteins according to the invention, typically well above 100 fusion protein units, e.g. 1000 fusion protein units or more. Optionally, the polymer may comprise as a further repeating structural unit complementary proteins without a B moiety, preferably proteins derived from spider silk. This may be advantageous if the B moiety of the fusion protein is large and/or bulky. These complementary proteins typically comprise a REP moiety and a CT moiety, and optionally an NT moiety, e.g. 1-2 NT moieties. Preferred complementary proteins according to the invention can have any of the structures set out herein with a deleted B moiety. It is preferred that the complementary fusion protein is substantially identical to the fusion protein with a deleted B moiety. However, it is preferred that the protein structure according to the invention is a polymer consisting of recombinant fusion proteins according to the invention as a repeating structural unit, i.e. that the protein structure according to the invention is a polymer of the recombinant fusion protein according to the invention.

The magnitude of fusion units in the polymer implies that the protein structure obtains a significant size. In a preferred embodiment, the protein structure has a size of at least 0.1 µm in at least two dimensions. Thus, the term "protein structure" as used herein relates to fusion protein polymers having a thickness of at least 0.1 µm, preferably macroscopic polymers that are visible to the human eye, i.e. having a thickness of at least 1 µm. The term "protein structure" does not encompass unstructured aggregates or precipitates. While monomers of the fusion protein are water soluble, it is understood that the protein structures according to the invention are solid structures, i.e. not soluble in water. The protein structures are polymers comprising as a repeating structural unit monomers of the recombinant fusion proteins according to the invention.

It is preferable that the protein structure according to the invention is in a physical form selected from the group consisting of fiber, film, foam, net, mesh, sphere and capsule.

It is preferable that the protein structure according to the invention is a fiber or film with a thickness of at least 1 nm, such as at least 0.1 µm, preferably at least 1 µm. It is preferred that the fiber or film has a thickness in the range of 1 nm-400 µm, such as 1-400 µm, and preferably 60-120 µm. It is preferred that fibers have a length in the range of 0.5-300 cm, preferably 1-100 cm. Other preferred ranges are 0.5-30 cm and 1-20 cm. The fiber has the capacity to remain intact during physical manipulation, i.e. can be used for spinning, weaving, twisting, crocheting and similar procedures. The film is advantageous in that it is coherent and adheres to solid structures, e.g. the plastics in microtiter plates. This property of the film facilitates washing and regeneration procedures and is very useful for separation purposes.

It is also preferred that the protein structure according to the invention has a tensile strength above 1 MPa, preferably above 2 MPa, more preferably 10 MPa or higher. It is preferred that the protein structure according to the invention has a tensile strength above 100 MPa, more preferably 200 MPa or higher.

The CT moiety is a protein fragment containing from 70 to 120 amino acid residues and is derived from the C-terminal fragment of a spider silk protein. The expression "derived from" implies in the context of the CT moiety according to the invention that it has a high degree of similarity to the C-terminal amino acid sequence of spider silk proteins. As shown in FIG. 1, this amino acid sequence is well conserved among various species and spider silk proteins, including MaSp1 and MaSp2. A consensus sequence of the C-terminal regions of MaSp1 and MaSp2 is provided as SEQ ID NO: 9. In FIG. 1, the following MaSp proteins are aligned, denoted with GenBank accession entries where applicable (SEQ ID NOS: 14-44):

TABLE 1

Spidroin CT moieties

| Species and spidroin protein | Entry |
| --- | --- |
| *Euprosthenops* sp MaSp1 (Pouchkina-Stantcheva, NN & McQueen-Mason, SJ, ibid) | Cthyb_Esp |
| *Euprosthenops australis* MaSp1 | CTnat_Eau |
| *Argiope trifasciata* MaSp1 | AF350266_At1 |
| *Cyrtophora moluccensis* Sp1 | AY666062_Cm1 |
| *Latrodectus geometricus* MaSp1 | AF350273_Lg1 |
| *Latrodectus hesperus* MaSp1 | AY953074_Lh1 |
| *Macrothele holsti* Sp1 | AY666068_Mh1 |
| *Nephila clavipes* MaSp1 | U20329_Nc1 |
| *Nephila pilipes* MaSp1 | AY666076_Np1 |
| *Nephila madagascariensis* MaSp1 | AF350277_Nm1 |
| *Nephila senegalensis* MaSp1 | AF350279_Ns1 |
| *Octonoba varians* Sp1 | AY666057_Ov1 |
| *Psechrus sinensis* Sp1 | AY666064_Ps1 |
| *Tetragnatha kauaiensis* MaSp1 | AF350285_Tk1 |
| *Tetragnatha versicolor* MaSp1 | AF350286_Tv1 |
| *Araneus bicentenarius* Sp2 | ABU20328_Ab2 |
| *Argiope amoena* MaSp2 | AY365016_Aam2 |
| *Argiope aurantia* MaSp2 | AF350263_Aau2 |
| *Argiope trifasciata* MaSp2 | AF350267_At2 |
| *Gasteracantha mammosa* MaSp2 | AF350272_Gm2 |
| *Latrodectus geometricus* MaSp2 | AF350275_Lg2 |
| *Latrodectus hesperus* MaSp2 | AY953075_Lh2 |
| *Nephila clavipes* MaSp2 | AY654293_Nc2 |
| *Nephila madagascariensis* MaSp2 | AF350278_Nm2 |
| *Nephila senegalensis* MaSp2 | AF350280_Ns2 |
| *Dolomedes tenebrosus* Fb1 | AF350269_DtFb1 |
| *Dolomedes tenebrosus* Fb2 | AF350270_DtFb2 |
| *Araneus diadematus* ADF-1 | U47853_ADF1 |
| *Araneus diadematus* ADF-2 | U47854_ADF2 |
| *Araneus diadematus* ADF-3 | U47855_ADF3 |
| *Araneus diadematus* ADF-4 | U47856_ADF4 |

It is not critical which specific CT moiety is present in spider silk proteins according to the invention, as long as the CT moiety is not entirely missing. Thus, the CT moiety according to the invention can be selected from any of the amino acid sequences shown in FIG. 1 and Table 1 (SEQ ID NOS: 14-44) or sequences with a high degree of similarity. A wide variety of C-terminal sequences can be used in the spider silk protein according to the invention.

The sequence of the CT moiety according to the invention has at least 50% identity, preferably at least 60%, more preferably at least 65% identity, or even at least 70% identity, to the consensus amino acid sequence SEQ ID NO: 9, which is based on the amino acid sequences of FIG. 1 (SEQ ID NOS: 14-44).

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

A representative CT moiety according to the invention is the *Euprosthenops australis* sequence SEQ ID NO: 7, Thus, according to a preferred aspect of the invention, the CT moiety has at least 80%, preferably at least 90%, such as at least 95%, identity to SEQ ID NO: 7 or any individual amino acid sequence of FIG. 1 and Table 1 (SEQ ID NOS: 14-44). In preferred aspects of the invention, the CT moiety is identical to SEQ ID NO: 7 or any individual amino acid sequence of FIG. 1 and Table 1.

The CT moiety typically consists of from 70 to 120 amino acid residues. It is preferred that the CT moiety contains at least 70, or more than 80, preferably more than 90, amino acid residues. It is also preferred that the CT moiety contains at most 120, or less than 110 amino acid residues. A typical CT moiety contains approximately 100 amino acid residues.

The optional REP moiety is a protein fragment containing from 70 to 300 amino acid residues and is derived from the repetitive fragment of a spider silk protein. This implies that the REP moiety has a repetitive character, alternating between alanine-rich stretches and glycine-rich stretches. The REP moiety generally contains more than 70, such as more than 140, and less than 300, preferably less than 240, such as less than 200, amino acid residues, and can itself be divided into several L (linker) segments, A (alanine-rich) segments and G (glycine-rich) segments, as will be explained in more detail below. Typically, said linker segments, which are optional, are located at the REP moiety terminals, while the remaining segments are in turn alanine-rich and glycine-rich. Thus, the REP moiety can generally have either of the following structures, wherein n is an integer:

L(AG)$_n$L, such as LA$_1$G$_1$A$_2$G$_2$A$_3$G$_3$A$_4$G$_4$A$_5$G$_5$L;
L(AG)$_n$AL, such as LA$_1$G$_1$A$_2$G$_2$A$_3$G$_3$A$_4$G$_4$A$_5$G$_5$A$_6$L;
L(GA)$_n$L, such as LG$_1$A$_1$G$_2$A$_2$G$_3$A$_3$G$_4$A$_4$G$_5$A$_5$L; or
L(GA)$_n$GL, such as LG$_1$A$_1$G$_2$A$_2$G$_3$A$_3$G$_4$A$_4$G$_5$A$_5$G$_6$L.

It follows that it is not critical whether an alanine-rich or a glycine-rich segment is adjacent to the N-terminal or C-terminal linker segments. It is preferred that n is an integer from 2 to 10, preferably from 2 to 8, preferably from 4 to 8, more preferred from 4 to 6, i.e. n=4, n=5 or n=6.

In preferred embodiments, the alanine content of the REP moiety according to the invention is above 20%, preferably above 25%, more preferably above 30%, and below 50%, preferably below 40%, more preferably below 35%. This is advantageous, since it is contemplated that a higher alanine content provides a stiffer and/or stronger and/or less extendible structure.

In certain embodiments, the REP moiety is void of proline residues, i.e. there are no proline residues in the REP moiety.

Now turning to the segments that constitute the REP moiety according to the invention, it shall be emphasized that each segment is individual, i.e. any two A segments, any two G segments or any two L segments of a specific REP moiety may be identical or may not be identical. Thus, it is not a general feature of the invention that each type of segment is identical within a specific REP moiety. Rather, the following disclosure provides the skilled person with guidelines how to design individual segments and gather them into a REP moiety which is thereby considered to be derived from the repetitive fragment of a spider silk protein, and which constitutes a part of a functional fusion protein according to the invention.

Each individual A segment is an amino acid sequence having from 8 to 18 amino acid residues. It is preferred that each individual A segment contains from 13 to 15 amino acid residues. It is also possible that a majority, or more than two, of the A segments contain from 13 to 15 amino acid residues, and that a minority, such as one or two, of the A segments contain from 8 to 18 amino acid residues, such as 8-12 or 16-18 amino acid residues. A vast majority of these amino acid residues are alanine residues. More specifically, from 0 to 3 of the amino acid residues are not alanine residues, and the remaining amino acid residues are alanine residues. Thus, all amino acid residues in each individual A segment are alanine residues, with no exception or the exception of one, two or three amino acid residues, which can be any amino acid. It is preferred that the alanine-replacing amino acid(s) is (are) natural amino acids, preferably individually selected from the group of serine, glutamic acid, cysteine and glycine, more preferably serine. Of course, it is possible that one or more of the A segments are all-alanine segments, while the remaining A segments contain 1-3 non-alanine residues, such as serine, glutamic acid, cysteine or glycine.

In a preferred embodiment, each A segment contains 13-15 amino acid residues, including 10-15 alanine residues and 0-3 non-alanine residues as described above. In a more preferred embodiment, each A segment contains 13-15 amino acid residues, including 12-15 alanine residues and 0-1 non-alanine residues as described above.

It is preferred that each individual A segment has at least 80%, preferably at least 90%, more preferably 95%, most preferably 100% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 10. Each sequence of this group corresponds to a segment of the naturally occurring sequence of *Euprosthenops australis* MaSp1 protein, which is deduced from cloning of the corresponding cDNA, see WO 2007/078239. Alternatively, each individual A segment has at least 80%, preferably at least 90%, more preferably 95%, most preferably 100% identity to an amino acid sequence selected from the group of amino acid residues 143-152, 174-186, 204-218, 233-247 and 265-278 of SEQ ID NO: 3. Each sequence of this group corresponds to a segment of expressed, non-natural spider silk proteins, which proteins have capacity to form silk structures under appropriate conditions. Thus, in certain embodiments according to the invention, each individual A segment is identical to an amino acid sequence selected from the above-mentioned amino acid segments. Without wishing to be bound by any particular theory, it is envisaged that A segments according to the invention form helical structures or beta sheets.

Furthermore, it has been concluded from experimental data that each individual G segment is an amino acid sequence of from 12 to 30 amino acid residues. It is preferred that each individual G segment consists of from 14 to 23 amino acid residues. At least 40% of the amino acid residues of each G segment are glycine residues. Typically the glycine content of each individual G segment is in the range of 40-60%.

It is preferred that each individual G segment has at least 80%, preferably at least 90%, more preferably 95%, most preferably 100% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 10. Each sequence of this group corresponds to a segment of the naturally occurring sequence of *Euprosthenops australis* MaSp1 protein, which is deduced from cloning of the corresponding cDNA, see WO 2007/078239. Alternatively, each individual G segment has at least 80%, preferably at least 90%, more preferably 95%, most preferably 100% identity to an amino acid sequence selected from the group of amino acid residues 153-173, 187-203, 219-232, 248-264 and 279-296 of SEQ ID NO: 3. Each sequence of this group corresponds to a segment of expressed, non-natural spider silk proteins, which proteins have capacity to form silk structures under appropriate conditions. Thus, in certain embodiments according to the invention, each individual G segment is identical to an amino acid sequence selected from the above-mentioned amino acid segments.

In certain embodiments, the first two amino acid residues of each G segment according to the invention are not -Gln-Gln-.

There are the three subtypes of the G segment according to the invention. This classification is based upon careful analysis of the *Euprosthenops australis* MaSp1 protein sequence (WO 2007/078239), and the information has been employed and verified in the construction of novel, non-natural spider silk proteins.

The first subtype of the G segment according to the invention is represented by the amino acid one letter consensus sequence GQG(G/S)QGG(Q/Y)GG (L/Q)GQG-GYGQGA GSS (SEQ ID NO: 11). This first, and generally the longest, G segment subtype typically contains 23 amino acid residues, but may contain as little as 17 amino acid residues, and lacks charged residues or contain one charged residue. Thus, it is preferred that this first G segment subtype contains 17-23 amino acid residues, but it is contemplated that it may contain as few as 12 or as many as 30 amino acid residues. Without wishing to be bound by any particular theory, it is envisaged that this subtype forms coil structures or $3_1$-helix structures. Representative G segments of this first subtype are amino acid residues 20-42, 84-106, 148-170, 212-234, 307-329, 371-393, 435-457, 530-552, 595-617, 689-711, 753-775, 817-839, 881-903, 946-968, 1043-1059 and 1074-1092 of SEQ ID NO: 10. In certain embodiments, the first two amino acid residues of each G segment of this first subtype according to the invention are not -Gln-Gln-.

The second subtype of the G segment according to the invention is represented by the amino acid one letter consensus sequence GQGGQGQG(G/R)Y GQG(A/S)G(S/G)S (SEQ ID NO: 12). This second, generally mid-sized, G segment subtype typically contains 17 amino acid residues and lacks charged residues or contain one charged residue. It is preferred that this second G segment subtype contains 14-20 amino acid residues, but it is contemplated that it may contain as few as 12 or as many as 30 amino acid residues. Without wishing to be bound by any particular theory, it is envisaged that this subtype forms coil structures. Representative G segments of this second subtype are amino acid residues 249-265, 471-488, 631-647 and 982-998 of SEQ ID NO: 10; and amino acid residues 187-203 of SEQ ID NO: 3.

The third subtype of the G segment according to the invention is represented by the amino acid one letter consensus sequence G(R/Q)GQG(G/R)YGQG (A/S/V)GGN (SEQ ID NO: 13). This third G segment subtype typically contains 14 amino acid residues, and is generally the shortest of the G segment subtypes according to the invention. It is preferred that this third G segment subtype contains 12-17 amino acid residues, but it is contemplated that it may contain as many as 23 amino acid residues. Without wishing to be bound by any particular theory, it is envisaged that this subtype forms turn structures. Representative G segments of this third subtype are amino acid residues 57-70, 121-134, 184-197, 280-293, 343-356, 407-420, 503-516, 567-580, 662-675, 726-739, 790-803, 854-867, 918-931, 1014-1027 of SEQ ID NO: 10; and amino acid residues 219-232 of SEQ ID NO: 3.

Thus, in preferred embodiments, each individual G segment has at least 80%, preferably 90%, more preferably 95%, identity to an amino acid sequence selected from SEQ ID NO: 11, SEQ ID NO: 12 and SEQ ID NO: 13.

In a preferred embodiment of the alternating sequence of A and G segments of the REP moiety, every second G segment is of the first subtype, while the remaining G segments are of the third subtype, e.g. . . . $A_1G_{short}A_2G_{long}A_3G_{short}A_4G_{long}A_5G_{short}$ . . . . In another preferred embodiment of the REP moiety, one G segment of the second subtype interrupts the G segment regularity via an insertion, e.g. . . . $A_1G_{short}A_2G_{long}A_3G_{mid}A_4G_{short}A_5G_{long}$ . . . .

Each individual L segment represents an optional linker amino acid sequence, which may contain from 0 to 20 amino acid residues, such as from 0 to 10 amino acid residues. While this segment is optional and not functionally critical for the spider silk protein, its presence still allows for fully functional spider silk fusion proteins, forming protein structures according to the invention. There are also linker amino acid sequences present in the repetitive part (SEQ ID NO:

10) of the deduced amino acid sequence of the MaSp1 protein from *Euprosthenops australis*. In particular, the amino acid sequence of a linker segment may resemble any of the described A or G segments, but usually not sufficiently to meet their criteria as defined herein.

Representative L segments are amino acid residues 1-6 and 1093-1110 of SEQ ID NO: 10; and amino acid residues 138-142 of SEQ ID NO: 3, but the skilled person in the art will readily recognize that there are many suitable alternative amino acid sequences for these segments. In one embodiment of the REP moiety according to the invention, one of the L segments contains 0 amino acids, i.e. one of the L segments is void. In another embodiment of the REP moiety according to the invention, both L segments contain 0 amino acids, i.e. both L segments are void. Thus, these embodiments of the REP moieties according to the invention may be schematically represented as follows: $(AG)_nL$, $(AG)_n$ AL, $(GA)_nL$, $(GA)_nGL$; $L(AG)_n$, $L(AG)_nA$, $L(GA)_n$, $L(GA)_nG$; and $(AG)_n$, $(AG)_nA$, $(GA)_n$, $(GA)_nG$. Any of these REP moieties are suitable for use with any CT moiety as defined below.

The optional NT moiety is a protein fragment containing from 100 to 160 amino acid residues and is derived from the N-terminal fragment of a spider silk protein. The expression "derived from" implies in the context of the NT moiety according to the invention that it has a high degree of similarity to the N-terminal amino acid sequence of spider silk proteins. As shown in FIG. 2, this amino acid sequence is well conserved among various species and spider silk proteins, including MaSp1 and MaSp2. In FIG. 2, the following spidroin NT moieties are aligned, denoted with GenBank accession entries where applicable (SEQ ID NOS: 45-58):

TABLE 2

Spidroin NT moieties

| Code | Species and spidroin protein | GenBank acc. no. |
|---|---|---|
| Ea MaSp1 | *Euprosthenops australis* MaSp 1 | AM259067 |
| Lg MaSp1 | *Latrodectus geometricus* MaSp 1 | ABY67420 |
| Lh MaSp1 | *Latrodectus hesperus* MaSp 1 | ABY67414 |
| Nc MaSp1 | *Nephila clavipes* MaSp 1 | ACF19411 |
| At MaSp2 | *Argiope trifasciata* MaSp 2 | AAZ15371 |
| Lg MaSp2 | *Latrodectus geometricus* MaSp 2 | ABY67417 |
| Lh MaSp2 | *Latrodectus hesperus* MaSp 2 | ABR68855 |
| Nim MaSp2 | *Nephila inaurata madagascariensis* MaSp 2 | AAZ15322 |
| Nc MaSp2 | *Nephila clavipes* MaSp 2 | ACF19413 |
| Ab CySp1 | *Argiope bruennichi* cylindriform spidroin 1 | BAE86855 |
| Ncl CySp1 | *Nephila clavata* cylindriform spidroin 1 | BAE54451 |
| Lh TuSp1 | *Latrodectus hesperus* tubuliform spidroin | ABD24296 |
| Nc Flag | *Nephila clavipes* flagelliform silk protein | AF027972 |
| Nim Flag | *Nephila inaurata* madagascariensis flagelliform silk protein | AF218623 (translated) |

Only the part corresponding to the N-terminal moiety is shown for each sequence, omitting the signal peptide. Nc flag and Nlm flag are translated and edited according to Rising A. et al. Biomacromolecules 7, 3120-3124 (2006)).

It is not critical which specific NT moiety is present in spider silk proteins according to the invention. Thus, the NT moiety according to the invention can be selected from any of the amino acid sequences shown in FIG. 2 and Table 2 (SEQ ID NOS: 45-58) or sequences with a high degree of similarity. A wide variety of N-terminal sequences can be used in the spider silk protein according to the invention. Based on the homologous sequences of FIG. 2, the following sequence constitutes a consensus NT amino acid sequence:

(SEQ ID NO: 8)
QANTPWSSPNLADAFINSF(M/L)SA(A/I)SSSGAFSADQLDDMSTI

G(D/N/Q)TLMSAMD(N/S/K)MGRSG(K/R)STKSKLQALNMAFASS

MAEIAAAESGG(G/Q)SVGVKTNAISDALSSAFYQTTGSVNPQFV (N/S)EIRSLI(G/N)M(F/L)(A/S)QASANEV.

The sequence of the NT moiety according to the invention has at least 50% identity, preferably at least 60% identity, to the consensus amino acid sequence SEQ ID NO: 8, which is based on the amino acid sequences of FIG. 2. In a preferred embodiment, the sequence of the NT moiety according to the invention has at least 65% identity, preferably at least 70% identity, to the consensus amino acid sequence SEQ ID NO: 8. In preferred embodiments, the NT moiety according to the invention has furthermore 70%, preferably 80%, similarity to the consensus amino acid sequence SEQ ID NO: 8.

A representative NT moiety according to the invention is the *Euprosthenops australis* sequence SEQ ID NO: 6. According to a preferred embodiment of the invention, the NT moiety has at least 80% identity to SEQ ID NO: 6 or any individual amino acid sequence in FIG. 2 (SEQ ID NOS: 45-58). In preferred embodiments of the invention, the NT moiety has at least 90%, such as at least 95% identity, to SEQ ID NO: 6 or any individual amino acid sequence in FIG. 2. In preferred embodiments of the invention, the NT moiety is identical to SEQ ID NO: 6 or any individual amino acid sequence in FIG. 2 (SEQ ID NOS: 45-58), in particular to Ea MaSp1 (SEQ ID NO: 45).

The NT moiety contains from 100 to 160 amino acid residues. It is preferred that the NT moiety contains at least 100, or more than 110, preferably more than 120, amino acid residues. It is also preferred that the NT moiety contains at most 160, or less than 140 amino acid residues. A typical NT moiety contains approximately 130-140 amino acid residues.

The B moiety is a protein or polypeptide fragment comprising more than 15 amino acid residues, such as 15-22 amino acid residues. The B moiety is preferably comprising more than 30 amino acid residues, such as more than 50 amino acid residues, such as more than 100 amino acid residues. The B moiety is preferably comprising less than 1000 amino acid residues, such as less than 400 amino acid residues, more preferably less than 300 amino acid residues. It is capable of selective interaction with the organic target, and it is the B moiety in the fusion protein which provides the capacity of selective interaction with the organic target.

The B moiety is a non-spidroin moiety. This implies that it is not derived from a spider silk protein, i.e. it has a low (or no) degree of identity and/or similarity to spider silk proteins. The sequence of the B moiety according to the invention preferably has less than 30% identity, such as less than 20% identity, preferably less than 10% identity, to any of the spidroin amino acid sequences disclosed herein, and specifically to any of SEQ ID NO: 6-10.

It is regarded as within the capabilities of those of ordinary skill in the art to select the B moiety. Nevertheless, examples of affinity ligands that may prove useful as B moieties, as well as examples of formats and conditions for detection and/or quantification, are given below for the sake of illustration.

The biomolecular diversity needed for selection of affinity ligands may be generated by combinatorial engineering of one of a plurality of possible scaffold molecules, and specific and/or selective affinity ligands are then selected using a suitable selection platform. Non-limiting examples of such structures, useful for generating affinity ligands against the organic target, are immunoglobulins and fragments of immunoglobulins.

The above-mentioned examples include scaffold proteins presenting a single randomized loop used for the generation of novel binding specificities, protein scaffolds with a rigid secondary structure where side chains protruding from the protein surface are randomized for the generation of novel binding specificities, and scaffolds exhibiting a non-contiguous hyper-variable loop region used for the generation of novel binding specificities. For selection of the desired affinity ligand from a pool of variants of any of the scaffold structures mentioned above, a number of selection platforms are available for the isolation of a specific novel ligand against a target protein of choice. Selection platforms include, but are not limited to, phage display (Smith G P (1985) Science 228:1315-1317), ribosome display (Hanes J and Pluckthun A (1997) Proc. Natl. Acad. Sci. U.S.A. 94:4937-4942), yeast two-hybrid system (Fields S and Song 0 (1989) Nature 340:245-246), yeast display (Gai S A and Wittrup K D (2007) Curr Opin Struct Biol 17:467-473), mRNA display (Roberts R W and Szostak J W (1997) Proc. Natl. Acad. Sci. U.S.A. 94:12297-12302), bacterial display (Daugherty P S (2007) Curr Opin Struct Biol 17:474-480, Kronqvist N et al. (2008) Protein Eng Des Sel 1-9, Harvey B R et al. (2004) PNAS 101(25):913-9198), microbead display (Nord O et al. (2003) J Biotechnol 106:1-13, WO01/05808), SELEX (System Evolution of Ligands by Exponential Enrichment) (Tuerk C and Gold L (1990) Science 249:505-510) and protein fragment complementation assays (PCA) (Remy I and Michnick S W (1999) Proc. Natl. Acad. Sci. U.S.A. 96:5394-5399).

A group of preferred B moieties are immunoglobulin fragments and molecules comprising immunoglobulin fragments or derivatives thereof. It is preferred that each immunoglobulin fragment of the B moiety is selected from immunoglobulin variable regions. It is further preferred that the B moiety is comprising at least one heavy chain variable region ($V_H$) and at least one light chain variable region ($V_L$).

A particularly preferred group of B moieties are single-chain variable fragments (scFv) of the variable regions of the heavy ($V_H$) and light ($V_L$) chains of immunoglobulins, optionally connected with a short linker peptide. The linker peptide is typically containing e.g. 10-25 amino acid residues and is rich in glycine, serine or threonine. The single-chain variable fragments according to the invention lack the constant Fc region found in complete antibody molecules. Preferred single-chain variable fragments according to the invention are thus characterized by that they do not bind to Protein G, but bind to Protein L from *Peptostreptococcus magnus*, since Protein L interacts with the variable region of kappa light chains.

One preferred group of B moieties are the fragment antigen-binding (Fab fragments) from immunoglobulins, i.e. the region on an antibody that binds to antigens. It is composed of one constant and one variable domain of each of the heavy and the light chain. The two variable domains bind the epitope on their specific antigens. A specific variant includes the $F(ab')_2$ fragments, i.e. an immunoglobulin monomer where the Fc fragment has been removed, e.g. by cleavage with pepsin.

Another preferred group of B moieties are domain antibodies (dAbs) or single domain antibodies (sdABs), also termed Nanobodies, occurring naturally in heavy chain immunoglobulins from camels. dAbs/sdABs are the smallest known antigen-binding fragments of antibodies, ranging from 11 kDa to 15 kDa. dAbs/sdAbs are the robust variable regions of the heavy ($V_H$) and/or light ($V_L$) chains of immunoglobulins. They are highly expressed in microbial cell culture, show favorable biophysical properties including solubility and temperature stability, and are well suited to selection and affinity maturation by in vitro selection systems such as phage display. They are also useful to create drugs with prolonged serum half-lives or other pharmacological activities.

Specific fusion proteins and protein structures according to the invention are provided in the Examples. These preferred fusion proteins form the group consisting of SEQ ID NOS 61-70, 72 and 74. Further preferred fusion proteins are having at least 80%, preferably at least 90%, more preferably at least 95%, identity to any of these sequences.

The present invention further provides isolated nucleic acids encoding a fusion protein according to the invention. In particular, specific nucleic acids are provided in the Examples and the appended sequence listing, e.g. SEQ ID NOS 59-60, 71 and 73. Further preferred nucleic acids encode fusion proteins having at least 80%, preferably at least 90%, more preferably at least 95%, identity to any of SEQ ID NOS 61-70, 72 and 74.

The nucleic acids according to the invention are useful for producing the fusion proteins according to the invention. The present invention provides a method of producing a fusion protein. The first step involves expressing in a suitable host a fusion protein according to the invention. Suitable hosts are well known to a person skilled in the art and include e.g. bacteria and eukaryotic cells, such as yeast, insect cell lines and mammalian cell lines. Typically, this step involves expression of a nucleic acid molecule which encodes the fusion protein in E. coli.

The second method step involves obtaining a mixture containing the fusion protein. The mixture may for instance be obtained by lysing or mechanically disrupting the host cells. The mixture may also be obtained by collecting the cell culture medium, if the fusion protein is secreted by the host cell. The thus obtained protein can be isolated using standard procedures. If desired, this mixture can be subjected to centrifugation, and the appropriate fraction (precipitate or supernatant) be collected. The mixture containing the fusion protein can also be subjected to gel filtration, chromatography, e.g. anion exchange chromatography, dialysis, phase separation or filtration to cause separation. Optionally, lipopolysaccharides and other pyrogens are actively removed at this stage. If desired, linker peptides may be removed by cleavage in this step.

Proteins structures, or formats, according to the invention are assembled spontaneously from the fusion proteins according to the invention under suitable conditions, and the assembly into polymers is promoted by the presence of shearing forces and/or an interface between two different phases e.g. between a solid and a liquid phase, between air and a liquid phase or at a hydrophobic/hydrophilic interface, e.g. a mineral oil-water interface. The presence of the resulting interface stimulates polymerization at the interface or in the region surrounding the interface, which region extends into the liquid medium, such that said polymerizing initiates at said interface or in said interface region. Various protein structures can be produced by adapting the conditions during the assembly. For instance, if the assembly is allowed to occur in a container that is gently wagged from side to side, a fiber is formed at the air-water interface. If the mixture is allowed to stand still, a film is formed at the air-water interface. If the mixture is evaporated, a film is formed at the bottom of the container. If oil is added on top of the aqueous mixture, a film is formed at the oil-water interface, either if allowed to stand still or if wagged. If the mixture is foamed, e.g. by bubbling of air or whipping, the foam is stable and solidifies if allowed to dry.

The present invention thus provides a method for providing a protein structure displaying a binding activity towards an organic target. In the first method step, there is provided a recombinant fusion protein according to the invention. The fusion protein may e.g. be provided by expressing it in a suitable host from a nucleic acid according to the invention. In the second method step, the fusion protein is subjected to conditions to achieve formation of a polymer comprising the recombinant fusion protein. Notably, although the spontaneously assembled protein structures can be solubilized in hexafluoroisopropanol, the solubilized fusion proteins are then not able to spontaneously reassemble into e.g. fibers.

The protein structure is useful as part of an affinity medium for immobilization of an organic target, wherein the B moiety is capable of selective interaction with the organic target. A sample, e.g. a biological sample, may be applied to a fusion protein or a protein structure according to the invention which is capable of binding to an organic target present in the biological sample, and the fusion protein or protein structure is then useful for separation of the organic target from the sample. A biological sample, such as blood, serum or plasma which has been removed from a subject may be subjected to detection, separation and/or quantification of the organic target.

The present invention thus provides a method for separation of an organic target from a sample. A sample, e.g. a biological sample such as blood, serum or plasma, containing the organic target is provided. The biological sample may be an earlier obtained sample. If using an earlier obtained sample in a method, no steps of the method are practiced on the human or animal body.

An affinity medium according to the invention is provided, comprising a fusion protein or a protein structure according to the invention. In certain embodiments, the affinity medium is consisting of the fusion protein or protein structure according to the invention. The affinity medium is capable of selective interaction with the organic target by means of the B moiety in the fusion protein according to the invention. The affinity medium is contacted with the sample under suitable conditions to achieve binding between the affinity medium and the organic target. Non-bound sample is removed under suitable conditions to maintain selective binding between the affinity medium and the organic target. This method results in an organic target immobilized to the affinity medium, and specifically to the fusion protein, according to the invention.

In a preferred method according to the invention, the fusion protein in the affinity medium is present as a protein structure according to the invention when contacting the affinity medium with the sample to achieve binding between the affinity medium and the organic target. The protein structures according to the invention are advantageous in that they adheres to solid supports, e.g. the plastics in microtiter plates. This property of the protein structure facilitates washing and regeneration procedures and is very useful for separation purposes.

It has surprisingly been observed that the alkali stability of the B moiety may even be enhanced when being part of a fusion protein according to the invention in a protein structure according to the invention. This property may be very useful for washing and regeneration purposes, e.g. allowing for high concentrations of NaOH, such as 0.1 M, 0.5 M, 1 M or even above 1 M, e.g. 2 M, and/or for high concentrations of urea, e.g. 6-8 M. The chemical stability may also be useful to allow for repeated cycles of use of the B moiety for selective interaction with an organic molecule or affinity purification. Furthermore, it has advantageously been shown that the fusion proteins according to the invention are heat stable. This allows for sterilization by heat with maintained solid protein format/structure as well as binding ability.

Another advantage of the fusion proteins according to the invention is that the resulting protein structure has a high density of B moieties. It is contemplated that this high density provides a high binding capacity. Altogether, these properties of the fusions proteins are very attractive for various B moieties with good production economy. These properties are also useful in other formats than in traditional gel bead affinity columns, e.g. in filter-like formats.

The immobilized organic target is capable of selective interaction with a second organic target. The method is then further comprising the step of contacting said affinity medium and the immobilized organic target with a second organic target, which is capable of selective interaction with the first organic target, under suitable conditions to achieve binding between the first and second organic targets.

The immobilized organic target is detectable and/or quantifiable. The detection and/or quantification of the organic target may be accomplished in any way known to the skilled person for detection and/or quantification of binding reagents in assays based on various biological or non-biological interactions. The organic targets may be labeled themselves with various markers or may in turn be detected by secondary, labeled affinity ligands to allow detection, visualization and/or quantification. This can be accomplished using any one or more of a multitude of labels, which can be conjugated to the organic target or to any secondary affinity ligand, using any one or more of a multitude of techniques known to the skilled person, and not as such involving any undue experimentation. Non-limiting examples of labels that can be conjugated to organic targets and/or secondary affinity ligands include fluorescent dyes or metals (e.g., fluorescein, rhodamine, phycoerythrin, fluorescamine), chromophoric dyes (e.g., rhodopsin), chemiluminescent compounds (e.g., luminal, imidazole) and bioluminescent proteins (e.g., luciferin, luciferase), haptens (e.g., biotin). A variety of other useful fluorophores and chromophores are described in Stryer L (1968) Science 162:526-533 and Brand L and Gohlke J R (1972) Annu. Rev. Biochem. 41:843-868. Organic targets and/or secondary affinity ligands can also be labeled with enzymes (e.g., horseradish peroxidase, alkaline phosphatase, beta-lactamase), radioisotopes (e.g., $^3$H, $^{14}$O, $^{32}$P, $^{35}$S or $^{125}$I) and particles (e.g., gold). In the context of the present disclosure, "particles" refer to particles, such as metal particles, suitable for labeling of molecules. Further, the affinity ligands may also be labeled with fluorescent semiconductor nanocrystals (quantum dots). Quantum dots have superior quantum yield and are more photostable compared to organic fluorophores and are therefore more easily detected (Chan et al. (2002) *Curr Opi Biotech.* 13: 40-46). The different types of labels can be conjugated to an organic target or a secondary affinity ligand using various chemistries, e.g., the amine reaction or the thiol reaction. However, other reactive groups than amines and thiols can be used, e.g., aldehydes, carboxylic acids and glutamine.

If the detection and/or quantification involves exposure to a second organic target or secondary affinity ligand, the affinity medium is washed once again with buffers to remove unbound secondary affinity ligands. As an example, the secondary affinity ligand may be an antibody or a fragment or a derivative thereof. Thereafter, organic targets may be detected and/or quantified with conventional methods. The binding properties for a secondary affinity ligand may vary, but those skilled in the art should be able to determine operative and optimal assay conditions for each determination by routine experimentation.

The detection, localization and/or quantification of a labeled molecule may involve visualizing techniques, such as light microscopy or immunofluoresence microscopy. Other methods may involve the detection via flow cytometry or luminometry. The method of visualization of labels may include, but is not restricted to, fluorometric, luminometric and/or enzymatic techniques. Fluorescence is detected and/or quantified by exposing fluorescent labels to light of a specific wavelength and thereafter detecting and/or quantifying the emitted light in a specific wavelength region. The presence of a luminescently tagged molecule may be detected and/or quantified by luminescence developed during a chemical reaction. Detection of an enzymatic reaction is due to a color shift in the sample arising from chemical reaction. Those of skill in the art are aware that a variety of different protocols can be modified in order for proper detection and/or quantification.

One available method for detection and/or quantification of the organic target is by linking it or the secondary affinity ligand to an enzyme that can then later be detected and/or quantified in an enzyme immunoassay (such as an EIA or ELISA). Such techniques are well established, and their realization does not present any undue difficulties to the skilled person. In such methods, the biological sample is brought into contact with a protein structure according to the invention which binds to the organic target, which is then detected and/or quantified with an enzymatically labeled secondary affinity ligand. Following this, an appropriate substrate is brought to react in appropriate buffers with the enzymatic label to produce a chemical moiety, which for example is detected and/or quantified using a spectrophotometer, fluorometer, luminometer or by visual means.

The organic target or the secondary affinity ligands can be labeled with radioisotopes to enable detection and/or quantification. Non-limiting examples of appropriate radiolabels in the present disclosure are $^3$H, $^{14}$C, $^{32}$P, $^{35}$S or $^{125}$I. The specific activity of the labeled affinity ligand is dependent upon the half-life of the radiolabel, isotopic purity, and how the label has been incorporated into the affinity ligand. Affinity ligands are preferably labeled using well-known techniques (Wensel T G and Meares C F (1983) in: *Radioimmunoimaging and Radioimmunotherapy* (Burchiel S W and Rhodes B A eds.) Elsevier, New York, pp 185-196). A thus radiolabeled affinity ligand can be used to visualize the organic target by detection of radioactivity. Radionuclear scanning can be performed with e.g. a gamma camera, magnetic resonance spectroscopy, emission tomography, gamma/beta counters, scintillation counters and radiographies.

Thus, the sample may be applied to the protein structure for detection, separation and/or quantification of the organic target. This procedure enables not only detection of the organic target, but may in addition show the distribution and relative level of expression thereof. Optionally, the organic target may be released from the affinity medium and collected. Thus, the use may comprise affinity purification on an affinity medium onto which the organic target has been immobilized. The protein structure may for example be arranged in a column or in well plates (such as 96 well plates), or on magnetic beads, agarose beads or sepharose beads. Further, the use may comprise use of the protein structures on a soluble matrix, for example using a dextran matrix, or use in a surface plasmon resonance instrument, such as a Biacore™ instrument, wherein the analysis may for example comprise monitoring the affinity for the immobilized organic target or a number of potential affinity ligands.

The protein structures according to the invention can be washed and regenerated with various cleaning agents, including acid, base and chaotropic agents. Particularly useful cleaning agents include NaOH, such as 0.1, 0.5 or 1 M NaOH, and urea, such as 6-8 M urea, Since the protein structures according to the invention are surprisingly resistant to chemical treatment and/or sterilizing heat treatment, the methods according to the invention involving use of the protein structures may comprise a final step of regenerating the protein structure. The methods preferably comprise a final step of regenerating the affinity medium by chemical treatment and/or sterilizing heat treatment. It is preferred that the chemical treatment comprises treatment with NaOH, such as 0.1, 0.5 or 1 M NaOH, and/or urea, such as 6-8 M urea, Fusion proteins according to the invention can be also be allowed to bind to an organic target in solution, i.e. prior to allowing the fusion protein to polymerize and form a protein structure, such as a film, a foam or a fibre. Both the spidroin-derived moieties (e.g. CT) as such and the corresponding fusion proteins incorporating a B moiety polymerise into solid structures even in the presence of contaminating proteins, without appreciable incorporation of contaminants into the material, and the functional (B) moieties retain their expected binding properties. It is therefore contemplated that the binding properties of the B moiety can be used to capture compounds or cells from the surrounding solution and incorporate the captured compounds or cells into or on a protein structure according to the invention.

Thus, in another preferred method according to the invention, the fusion protein in the affinity medium is present in solution when contacting the affinity medium with the sample to achieve binding between the affinity medium and the organic target. The complex of fusion protein bound to the organic target is then allowed to form a fusion protein structure according to the invention.

This method may be particularly useful when the purpose is to "fish out" specific molecules or cells from a solution, e.g. to obtain target molecules from the media in large scale eukaryotic cell production systems when the target proteins are secreted. Since the binding of target molecules and formation of solid structures by the spidroin-derived moieties can take place at physiological conditions and since the spidroin-derived moieties are cytocompatible, the method can be applied repeatedly to an ongoing production process.

The protein structure according to the invention is also useful in separation, immobilization and/or cultivation of cells. A particularly useful protein structure in this respect is a film, a fiber or a foam. The film is advantageous in that it adheres to solid structures, e.g. the plastics in microtiter plates. This property of the film facilitates washing and regeneration procedures and is very useful for selective detection and separation purposes.

The present invention thus provides a cell scaffold material for cultivation of cells having an organic target that is present on the cell surface. The cell scaffold material is comprising a protein structure according to the invention. In certain embodiments, the cell scaffold material is consisting of the protein structure according to the invention.

It has been found by the present inventors that a cell scaffold material comprising a polymer comprising, and optionally consisting of, the fusion protein according to the invention provides a beneficial environment for the cultivation of cells, and preferably eukaryotic cells, in a variety of different settings. Furthermore, this environment enables the establishment of cultures of cells that are otherwise very difficult, very costly or even impossible to culture in a laboratory, and for the establishment of cell-containing materials useful for tissue engineering and/or transplantation.

The invention also provides a combination of cells, preferably eukaryotic cells, and the cell scaffold material according to the invention. Such a combination according to the invention may be presented in a variety of different formats, and tailored to suit the needs of a specific situation. It is contemplated, for example, that the inventive combination may be useful as a cell-containing implant for the replacement of cells in damaged or diseased tissue.

The cell scaffold material can be utilized to capture cells either directly or indirectly. In direct capture, the B moiety is capable of selective interaction with an organic target that is present on the cell surface. Alternatively, the B moiety is capable of selective interaction with and is bound to an intermediate organic target, and that intermediate organic target is capable of selective interaction with an organic target that is present on the cell surface. Thus, in indirect capture, the cell scaffold material is further comprising an intermediate organic target, and the B moiety is capable of selective interaction with and is bound to said intermediate organic target. The intermediate organic target, in turn, is capable of selective interaction with the organic target that is present on the cell surface.

In one embodiment of the cell scaffold materials as disclosed herein, the fusion protein is further comprises an oligopeptide cell-binding motif. In connection with the cultivation of certain cells in certain situations, the presence of oligopeptide cell-binding motifs has been observed to improve or maintain cell viability, and the inclusion of such a motif into the cell scaffold material as a part of the spider silk protein is thought to provide additional benefits. The cell-binding motif is an oligopeptide coupled to the rest of the fusion protein via at least one peptide bond. For example, it may be coupled to the N-terminal or the C-terminal of the rest of the fusion protein, or at any position within the amino acid sequence of the rest of the spider silk protein. With regard to the selection of oligopeptidic cell-binding motifs, the skilled person is aware of several alternatives. The coupling of an oligopeptide cell-binding motif to the rest of the spider silk protein is readily accomplished by the skilled person using standard genetic engineering or chemical coupling techniques. Thus, in some embodiments, the cell-binding motif is introduced via genetic engineering, i.e. forming part of a genetic fusion between a nucleic acid encoding a fusion protein and the cell-binding motif. As an additional beneficial characteristic of such embodiments, the cell-binding motif will be present in a 1:1 ratio to the monomers of fusion protein in the polymer making up the cell scaffold material.

The polymer in the cell scaffold material used in the methods or combination described herein may adopt a variety of physical forms, and use of a specific physical form may offer additional advantages in different specific situations. For example, in an embodiment of the methods or combination, said cell scaffold material is in a physical form selected from the group consisting of film, foam, capsules, fiber and fiber-mesh.

The present invention accordingly provides a method for immobilization of cells. A sample e.g. a biological sample such as blood, comprising cells of interest is provided. The biological sample may be an earlier obtained sample. If using an earlier obtained sample in a method, no steps of the method are practiced on the human or animal body.

The sample is applied to a cell scaffold material according to the invention under suitable conditions to allow selective interaction between the cell scaffold material and an organic target that is present on the surface of the cells of interest. The cells are allowed to immobilize to said cell scaffold material by binding between the organic target on the cell surface and said cell scaffold material. Non-bound sample is removed under suitable conditions to maintain selective binding between the cell scaffold material and the organic target. This method results in cells exhibiting the organic target being immobilized to the cell scaffold material, and specifically to the protein structure, according to the invention.

As set out above, the cell scaffold material can be utilized to capture cells either directly or indirectly. In direct capture, the B moiety is capable of selective interaction with an organic target that is present on the cell surface. Alternatively, the B moiety is capable of selective interaction with and is bound to an intermediate organic target, and that intermediate organic target is capable of selective interaction with an organic target that is present on the cell surface. Thus, in indirect capture, the cell scaffold material is further comprising an intermediate organic target, and the B moiety is capable of selective interaction with and is bound to said intermediate organic target. The intermediate organic target, in turn, is capable of selective interaction with the organic target that is present on the cell surface.

Regardless of capture method, the captured cells may be released from the fusion protein by cleavage of the fusion protein to release the moiety involved in cell capture from the cell scaffold material. As mentioned hereinabove, the fusion protein may include a cleavage site in its amino acid sequence, which allows for cleavage and removal of the relevant moiety, typically the B moiety or a cell-binding motif. Various cleavage sites are known to the person skilled in the art, e.g. cleavage sites for chemical agents, such as CNBr after Met residues and hydroxylamine between Asn-Gly residues, cleavage sites for proteases, such as thrombin or protease 3C, and self-splicing sequences, such as intein self-splicing sequences.

The present invention also provides a method for cultivation of cells. Cells of interest are immobilized to the cell scaffold material using the method disclosed hereinabove. The combination of the cell scaffold material and the immobilized cells are maintained under conditions suitable for cell culture.

In the context of the present invention, the terms "cultivation" of cells, "cell culture" etc are to be interpreted broadly, such that they encompass for example situations in which cells divide and/or proliferate, situations in which cells are maintained in a differentiated state with retention of at least one functional characteristic exhibited by the cell type when present in its natural environment, and situations in which stem cells are maintained in an undifferentiated state.

The present invention will in the following be further illustrated by the following non-limiting examples.

EXAMPLES

Example 1—Cloning, Expression and Fiber Formation of ScFv-Rep$_4$CT Fusion Proteins To prove the fusion protein concept, a Rep$_4$CT protein (a REP moiety with 4 internal repeats and a CT moiety) was produced in fusion with the single chain fragment variable (ScFv) (a B moiety). ScFv consist of VH and VL joined genetically together via a flexible polypeptide linker. This is the smallest (27 kDa) entity with intact antigen binding capacity. The aim was to investigate whether it is possible to produce structures, such as fibers, films and membranes, from a fusion protein consisting of the ScFv fused to Rep$_4$CT and still retain the antigen-binding ability of ScFv, as well as the structure forming properties of Rep$_4$CT. In order to do so one fusion protein consisting of the ScFv N-terminally and one C-terminally to Rep$_4$CT was cloned.

Cloning

Genes (SEQ ID NOS: 59-60) encoding the His$_6$ScFvRep$_4$CT and His$_6$Rep$_4$CTScFv fusion proteins (SEQ ID NOS: 61-62) were constructed. The vectors were transformed into chemocompetent *Escherichia coli* (*E. coli*) BL21 (DE3) cells that were allowed to grow onto agar plates supplemented with kanamycin (70 μg/ml). Colonies were thereafter picked and PCR screened for correct insert and subsequently also sequenced to confirm the DNA sequence.

Production

*E. coli* BL21 (DE3) cells possessing the pT7His$_6$ScFvRep$_4$CT or pT7His$_6$ScFvRep$_4$CT vector were grown in Luria-Bertani medium (6 liter in total) supplemented with kanamycin (70 μg/ml) to an OD$_{600}$ value of 1-1.5 in 30° C., followed by induction of expression with 300 μM IPTG (isopropyl β-D-1-thiogalactopyranoside) and further incubation in 20° C. for approximately 2 h. Next, the cells were harvested by a 20 min centrifugation at 4 700 rpm, and the resulting cell pellets were dissolved in 20 mM Tris (pH 8.0).

Purification

Cell pellets dissolved in 20 mM Tris (pH 8.0) were supplemented with lysozyme and DNase I in order to lyse the bacterial cells, whereupon the cell lysates were recovered after 15 000 rpm of centrifugation for 30 min. Next, the recovered cell lysates were divided and loaded onto a total of four Chelating Sepharose Fast Flow Zn$^{2+}$ columns, keeping the protein bound to the column matrix via the His$_6$ tag. After washing, bound proteins were eluted with 20 mM Tris/300 mM imidazole (pH 8.0). Next, the pooled eluate liquid was dialysed against 5 liters of 20 mM Tris (pH 8.0) over night, concentrated to 1 mg/ml and finally allowed to form fibers or films.

The fact that macroscopic fibers of His$_6$ScFvRep$_4$CT as well as His$_6$Rep$_4$CTScFv could be obtained although Rep$_4$CT has been fused to another protein, i.e. the 27 kDa ScFv, demonstrates that Rep$_4$CT still retains its fiber forming properties despite fused to ScFv.

Analysis of Binding to ScFv

Two different methods were used for detection of antigen binding to the ScFv alone or in fusions with Rep$_4$CT: A) Direct addition of a Alexa647-labelled antigen, wash, and subsequent fluorescence measurement. B) Addition of biotynilated serum samples, wash, addition of Alexa647-labelled steptavidin, wash, and subsequent fluorescence measurements.

Results

Both ScFvRep$_4$CT and Rep$_4$CTScFv could be expressed, purified and assembled into films or fibers. All following experiments were done on films. Analysis of antigen binding using direct addition of Alex647-labelled antigen showed that both ScFv4repCT and 4RepCTScFv gave more intense spots, and thus bound more antigen than ScFv did when alone (FIG. 3A). The intensity of the spots were measured at different detection intensities and ploted in FIG. 3B.

FIG. 3 shows analysis of binding of Alexa647-labelled antigen:

A) Fluorographs of spots with bound antigen. The whiter dots, the more antigen.

B) Measurements of the intensity of the dots, using different detection intensities.

Analysis of biotinylated antigen from serum samples and subsequent steptavin binding showed that both ScFvRep$_4$CT and Rep$_4$CTScFv gave more intense spots, and thus bound more antigen than ScFv alone (FIG. 4). However, unspecific binding to spots with only Rep$_4$CT can also be seen, although giving much lower signal than ScFvRep$_4$CT and Rep$_4$CTScFv. This could be due to unspecific binding of either something else in the serum (e.g. albumin) or streptavidin.

FIG. 4 shows analysis of binding of biotinylated antigen detected with Alexa647-labelled streptavidin. A) Fluorographs of spots with bound antigen and streptavidin. The whiter dots the more antigen. B) Measurements of the intensity of the dots, using different detection intensities.

Conclusions

Films spotted from ScFv fusions with Rep$_4$CT proteins bind >10 times more pure antigen compared to ScFv alone. However, if a biotinylated serum sample is analyzed with fluorophore labeled streptavidin, there are some unspecific binding (approx. 5 times lower) to Rep$_4$CT films that does not contain ScFv.

Example 2—Cloning, Expression and Fiber Formation of ScFv-CT Fusion Proteins

To prove the fusion protein concept, a CT protein (a CT moiety) is produced in fusion with the single chain fragment variable (ScFv) (a B moiety). The aim is to investigate whether it is possible to produce structures, such as fibers, films and membranes, from a fusion protein consisting of the ScFv fused to CT and still retain the antigen-binding ability of ScFv, as well as the structure forming properties of CT. In order to do so one fusion protein consisting of the ScFv N-terminally and one C-terminally to CT is cloned.

Cloning

Genes encoding the His$_6$ScFvCT and His$_6$CTScFv fusion proteins (SEQ ID NOS: 63-64) are constructed. The vectors are transformed into chemocompetent *E. coli* BL21 (DE3) cells that are allowed to grow onto agar plates supplemented with kanamycin (70 μg/ml). Colonies are thereafter picked and PCR screened for correct insert and subsequently also sequenced to confirm the DNA sequence.

Production

*E. coli* BL21 (DE3) cells possessing the pT7His$_6$ScFvCT or pT7His$_6$ScFvCT vector are grown in Luria-Bertani medium (6 liter in total) supplemented with kanamycin (70 μg/ml) to an OD$_{600}$ value of 1-1.5 in 30° C., followed by induction of expression with 300 μM IPTG and further incubation in 20° C. for approximately 2 h. Next, the cells are harvested by a 20 min centrifugation at 4 700 rpm, and the resulting cell pellets are dissolved in 20 mM Tris (pH 8.0).

Purification

Cell pellets dissolved in 20 mM Tris (pH 8.0) are supplemented with lysozyme and DNase I in order to lyse the bacterial cells, whereupon the cell lysates are recovered after 15 000 rpm of centrifugation for 30 min. Next, the recovered cell lysates are divided and loaded onto a total of four Chelating Sepharose Fast Flow Zn$^{2+}$ columns, keeping the protein bound to the column matrix via the His$_6$ tag. After washing, bound proteins are eluted with 20 mM Tris/300 mM imidazole (pH 8.0). Next, the pooled eluate liquid is dialysed against 5 liters of 20 mM Tris (pH 8.0) over night, concentrated to 1 mg/ml and finally allowed to form fibers or films.

Analysis of Binding to ScFv

Two different methods are used for detection of antigen binding to the ScFv alone or in fusions with CT: A) Direct addition of a Alexa647-labelled antigen, wash, and subsequent fluorescence measurement. B) Addition of biotinylated serum samples, wash, addition of Alexa647-labelled steptavidin, wash, and subsequent fluorescence measurements.

Example 3—Cloning, Expression and Fiber Formation of ScFv-NTCT Fusion Proteins

To prove the fusion protein concept, a NT-CT protein (a NT and a CT moiety) is produced in fusion with the single chain fragment variable (ScFv) (a B moiety). The aim is to investigate whether it is possible to produce structures, such as fibers, films and membranes, from a fusion protein consisting of the ScFv fused to NT-CT and still retain the antigen-binding ability of ScFv, as well as the structure forming properties of NT-CT. In order to do so one fusion protein consisting of the ScFv N-terminally and one C-terminally to NTCT is cloned.

Cloning

Genes encoding the His$_6$ScFvNT-CT and His$_6$NT-CTScFv fusion proteins (SEQ ID NOS: 65-66) are constructed. The vectors were transformed into chemocompetent *E. coli* BL21 (DE3) cells that are allowed to grow onto agar plates supplemented with kanamycin (70 μg/ml). Colonies are thereafter picked and PCR screened for correct insert and subsequently also sequenced to confirm the DNA sequence.

Production

*E. coli* BL21 (DE3) cells possessing the pT7His$_6$ScFvNT-CT or pT7His$_6$ScFvNT-CT vector are grown in Luria-Bertani medium (6 liter in total) supplemented with kanamycin (70 μg/ml) to an OD$_{600}$ value of 1-1.5 in 30° C., followed by induction of expression with 300 μM IPTG and further incubation in 20° C. for approximately 2 h. Next, the cells are harvested by a 20 min centrifugation at 4 700 rpm, and the resulting cell pellets are dissolved in 20 mM Tris (pH 8.0).

Purification

Cell pellets dissolved in 20 mM Tris (pH 8.0) are supplemented with lysozyme and DNase I in order to lyse the bacterial cells, whereupon the cell lysates were recovered after 15 000 rpm of centrifugation for 30 min. Next, the recovered cell lysates were divided and loaded onto a total of four Chelating Sepharose Fast Flow Zn$^{2+}$ columns, keeping the protein bound to the column matrix via the His$_6$ tag. After washing, bound proteins are eluted with 20 mM Tris/300 mM imidazole (pH 8.0). Next, the pooled eluate liquid is dialysed against 5 liters of 20 mM Tris (pH 8.0) over night, concentrated to 1 mg/ml and finally allowed to form fibers or films.

Analysis of Binding to ScFv

Two different methods are used for detection of antigen binding to the ScFv alone or in fusions with NTCT: A) Direct addition of a Alexa647-labelled antigen, wash, and subsequent fluorescence measurement. B) Addition of biotynilated serum samples, wash, addition of Alexa647-labelled steptavidin, wash, and subsequent fluorescence measurements.

Example 4—Cloning, Expression and Fiber Formation of ScFv-NTRep$_4$CT Fusion Proteins To prove the fusion protein concept, a NTRep$_4$CT protein (a NT, a REP moiety with 4 internal repeats and a CT moiety) is produced in fusion with the single chain fragment variable (ScFv) (a B moiety). The aim is to investigate whether it is possible to produce structures, such as fibers, films and membranes, from a fusion protein consisting of the ScFv fused to NT-CT and still retain the antigen-binding ability of ScFv, as well as the structure forming properties of NTRep$_4$CT. In order to do so one fusion protein consisting of the ScFv N-terminally and one C-terminally to NTRep$_4$CT is cloned.

Cloning

Genes encoding the His$_6$ScFvNTRep$_4$CT and His$_6$NTRep$_4$CTScFv fusion proteins (SEQ ID NOS: 67-68) are constructed. The vectors are transformed into chemocompetent E. coli BL21 (DE3) cells that are allowed to grow onto agar plates supplemented with kanamycin (70 µg/ml). Colonies are thereafter picked and PCR screened for correct insert and subsequently also sequenced to confirm the DNA sequence.

Production

E. coli BL21 (DE3) cells possessing the pT7His$_6$ScFvNTRep$_4$CT or pT7His$_6$ScFvNTRep$_4$CT vector are grown in Luria-Bertani medium (6 liter in total) supplemented with kanamycin (70 µg/ml) to an OD$_{600}$ value of 1-1.5 in 30° C., followed by induction of expression with 300 µM IPTG and further incubation in 20° C. for approximately 2 h. Next, the cells are harvested by a 20 min centrifugation at 4 700 rpm, and the resulting cell pellets are dissolved in 20 mM Tris (pH 8.0).

Purification

Cell pellets dissolved in 20 mM Tris (pH 8.0) are supplemented with lysozyme and DNase I in order to lyse the bacterial cells, whereupon the cell lysates are recovered after 15 000 rpm of centrifugation for 30 min. Next, the recovered cell lysates are divided and loaded onto a total of four Chelating Sepharose Fast Flow Zn$^{2+}$ columns, keeping the protein bound to the column matrix via the His$_6$ tag. After washing, bound proteins are eluted with 20 mM Tris/300 mM imidazole (pH 8.0). Next, the pooled eluate liquid is dialysed against 5 liters of 20 mM Tris (pH 8.0) over night, concentrated to 1 mg/ml and finally allowed to form fibers or films.

Analysis of Binding to ScFv

Two different methods are used for detection of antigen binding to the ScFv alone or in fusions with NTRep$_4$CT: A) Direct addition of a Alexa647-labelled antigen, wash, and subsequent fluorescence measurement. B) Addition of biotynilated serum samples, wash, addition of Alexa647-labelled steptavidin, wash, and subsequent fluorescence measurements.

Example 5—Cloning, Expression and Fiber Formation of ScFv-NTNTCT Fusion Proteins To prove the fusion protein concept, a NTNT-CT protein (two NT and one CT moieties) is produced in fusion with the single chain fragment variable (ScFv) (a B moiety). The aim is to investigate whether it is possible to produce structures, such as fibers, films and membranes, from a fusion protein consisting of the ScFv fused to NT-CT and still retain the antigen-binding ability of ScFv, as well as the structure forming properties of NT-CT. In order to do so one fusion protein consisting of the ScFv N-terminally and one C-terminally to NTNTCT is cloned.

Cloning

Genes encoding the His$_6$ScFvNTNT-CT and His$_6$NTNT-CTScFv fusion proteins (SEQ ID NOS: 69-70) are constructed. The vectors are transformed into chemocompetent E. coli BL21 (DE3) cells that are allowed to grow onto agar plates supplemented with kanamycin (70 µg/ml). Colonies are thereafter picked and PCR screened for correct insert and subsequently also sequenced to confirm the DNA sequence.

Production

E. coli BL21 (DE3) cells possessing the pT7His$_6$ScFvNTNT-CT or pT7His$_6$ScFvNTNT-CT vector are grown in Luria-Bertani medium (6 liter in total) supplemented with kanamycin (70 µg/ml) to an OD$_{600}$ value of 1-1.5 in 30° C., followed by induction of expression with 300 µM IPTG (isopropyl β-D-1-thiogalactopyranoside) and further incubation in 20° C. for approximately 2 h. Next, the cells are harvested by a 20 min centrifugation at 4 700 rpm, and the resulting cell pellets are dissolved in 20 mM Tris (pH 8.0).

Purification

Cell pellets dissolved in 20 mM Tris (pH 8.0) are supplemented with lysozyme and DNase I in order to lyse the bacterial cells, whereupon the cell lysates are recovered after 15 000 rpm of centrifugation for 30 min. Next, the recovered cell lysates are divided and loaded onto a total of four Chelating Sepharose Fast Flow Zn$^{2+}$ columns, keeping the protein bound to the column matrix via the His$_6$ tag. After washing, bound proteins are eluted with 20 mM Tris/300 mM imidazole (pH 8.0). Next, the pooled eluate liquid is dialysed against 5 liters of 20 mM Tris (pH 8.0) over night, concentrated to 1 mg/ml and finally allowed to form fibers or films.

Analysis of Binding to ScFv

Two different methods are used for detection of antigen binding to the ScFv alone or in fusions with NTNT-CT: A) Direct addition of a Alexa647-labelled antigen, wash, and subsequent fluorescence measurement. B) Addition of biotynilated serum samples, wash, addition of Alexa647-labelled steptavidin, wash, and subsequent fluorescence measurements.

Example 6—Cloning, Expression and Formation of Structures of scFv1-NTCT and scFv1-CT Fusion Proteins NTCT and CT were produced in fusion with an engineered antibody fragment named single chain fragment variable 1 (scFv1). scFv1 is a 27-kDa monovalent, engineered antibody fragment that recognizes the antigens specific for an autoimmune disease, Systemic Lupus Erythematosus (SLE). Our aim was to investigate whether it is possible to produce structures, such as fibers and films, from the fusion proteins consisting of the scFv1 protein domain fused to NTCT (denoted His$_6$-scFv1-NTCT, SEQ ID NO: 72) and to CT (denoted His$_6$-scFv1-CT, SEQ ID NO: 74) respectively, and still retain the antigen detection ability of scFv1 domain as well as the structure forming properties of NTCT and CT. In order to do so, two fusion proteins consisting of the scFv1 domain fused N-terminally to NTCT and to CT were cloned.

Cloning

A gene (SEQ ID NO: 73) encoding the $His_6$-scFv1-CT fusion protein (SEQ ID NO: 74) was constructed as follows. Primers were designed in order to generate PCR fragments of domain scFv1 from a vector containing such a scFv1 sequence. Also, the primers contained recognition sites for the restriction endonucleases NdeI and EcoRI. The resulting PCR products were then treated with the restriction endonucleases NdeI and EcoRI, as was the target vector (denoted pAff8$His_6$TrxHis$_6$CT, harbouring a kanamycin resistance gene). Upon restriction cleavage of the target vector, the $His_6$TrxHis$_6$ part was cleaved off. Cleaved PCR fragments and target vector were joined together with the aid of a T4 DNA Ligase, whereupon the resulting correctly ligated vector (pT7$His_6$-scFv1-CT) was transformed into chemocompetent E. coli BL21 (DE3) cells that were allowed to grow onto agar plates supplemented with kanamycin (50 μg/ml). Colonies were thereafter picked and screened for correct insert and subsequently also sequenced to confirm the DNA sequence of inserted scFv1 into the target vector.

Cloning of a gene (SEQ ID NO: 71) encoding the $His_6$-scFv1-NTCT fusion protein (SEQ ID NO: 72) was performed in the same way as described for $His_6$-scFv1-CT, but the primers used for the amplification of NTCT contained sites for the restriction endonucleases EcoRI and HindIII and the target vector here was denoted by pT7$His_6$scFv1-RepCT, where the RepCT part was cleaved off upon treatment with EcoRI and HindIII. The correctly ligated vector is denoted as pT7$His_6$scFv1-NTCT.

Production

E. coli BL21 (DE3) cells possessing the pT7$His_6$-scFv1-CT vector were grown in Luria-Bertani medium (3 liters in total) supplemented with kanamycin (50 μg/ml) to an $OD_{600}$ value of 1-1.5 in 30° C., followed by induction of pT7$His_6$-scFv1-CT expression with 300 μM IPTG and further incubation at 14° C. for approximately 17 h. Next, the cells were harvested by a 20 min centrifugation at 4 700 rpm, and the resulting cell pellet was dissolved in 20 mM Tris (pH 8.0).

Production of pT7$His_6$-scFv1-NTCT was performed in the same way as described for pT7$His_6$-scFv1-CT except for the total volume of the culture media used (6 liters) in its production.

Purification

The cell pellet dissolved in 20 mM Tris (pH 8.0) was supplemented with lysozyme and DNase I in order to lyse the bacterial cells, followed by the addition of NaCl and imidazole to a final concentration of 200 mM and 10 mM, respectively. After 30 min of centrifugation (15 000 rpm) the cell lysate was recovered. Next, the recovered cell lysate was loaded onto a Chelating Sepharose Fast Flow $Zn^{2+}$ column, keeping the $His_6$-scFv1-CT (SEQ ID NO: 74) protein bound to the column matrix via the $His_6$ tag. After washing, bound proteins were eluted with 20 mM Tris/200 mM imidazole (pH 8.0)/300 mM NaCl. The eluate contained 0.93 mg of $His_6$-scFv1-CT protein according to an $A_{280}$ measurement. Next, the eluted protein was dialyzed against 3 liters of 20 mM Tris (pH 8.0) over night and thereafter concentrated to 0.87 mg/ml, yielding a final amount of 0.348 mg $His_6$-scFv1-CT fusion protein (SEQ ID NO: 74).

The same purification procedure was carried out for $His_6$-scFv1-NTCT (SEQ ID NO: 72), whose eluate contained 4.86 mg of fusion protein. After protein concentration to 2.14 mg/ml, a final amount of 2.57 mg $His_6$-scFv1-NTCT was obtained.

Film, Foam and Fiber Formation

Films of $His_6$-scFv1-CT were spotted onto microarray slides (plastic MaxiSorp, Nunc) from 1 μl of 5 μM soluble fusion protein per film. The films were then allowed to solidify over night in a climate controlled room. The same procedure was followed for casting films of $His_6$-scFv1-NTCT from 1 μl of 5 μM protein solution.

Figure 5:
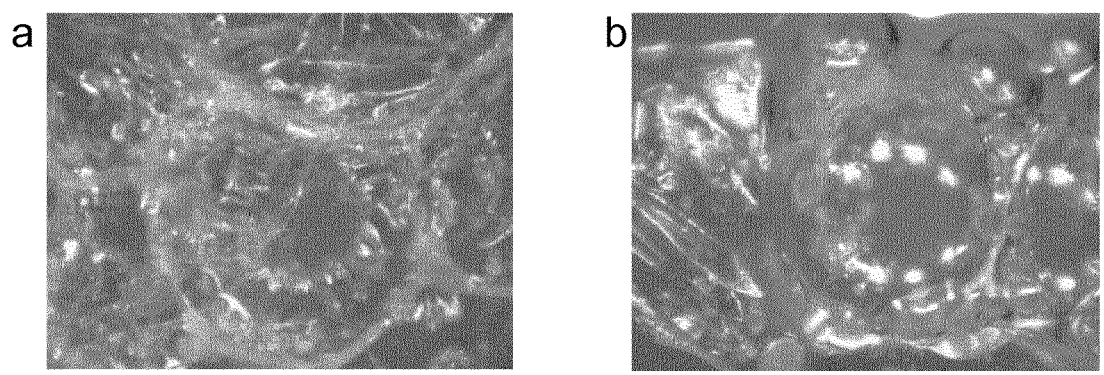
FIG. 5 shows microscopic pictures of silk fused antibody fragments in foam format.

Fiber was made for $His_6$-scFv1-NTCT from 0.49 mg/ml (data not shown) and foams were made for both $His_6$-scFv1-NTCT and $His_6$-scFv1-CT from 30 μl of 0.22 and 0.38 mg/ml of soluble fusion protein, respectively (FIGS. 5a and 5b). The fact that macroscopic fiber and foam for His6-scFv1-NTCT and His6-scFv1-CT respectively, could be obtained although NTCT or CT has been fused to another protein, i.e. the 263 amino acids long scFv1 domain, demonstrates that NTCT and CT still retains there structure forming properties despite fused to the scFv1 domain.

Analysis

Pure antibody (scFv1, control) and silk fused antibody (scFv1-NTCT) were spotted in the microarray format manually by adding 1 μL of 5 μM protein solution onto clear and black polymer MaxiSorp microarray slides (NUNC, 25×76 mm) resulting in 135 μmoles of pure antibody (scFv1) and 274 pmoles of silk fused antibody (scFv1-NTCT) in the spotted films, respectively. After spotting the proteins in film format, the films were dried overnight in a climate controlled room. The arrays were then blocked by applying 200 μl of sample buffer (1% (w/v) fat-free milk powder and 1% (v/v) Tween-20 in PBS) for 90 min and then washed three times by applying 200-300 μl of wash buffer (0.05% (v/v) Tween-20 in PBS). All incubations were performed at room temperature on gentle agitation. Next, 100-200 μl of biotinylated antigen sample (10 nM) diluted in sample buffer was applied and incubated for 1 h. The arrays were then washed three times by applying 200-300 μl of wash buffer and to detect the bound antigens, 100-200 μl of Alexa-647-labeled streptavidin (1 μg/ml) diluted in sample buffer, was applied onto the arrays and incubated for 1 h. Finally, the arrays were washed three times with 200-300 μl of wash buffer and dried under a stream of nitrogen gas. The arrays were then scanned using a confocal microarray fluorescence scanner (ScanArray Express, Perkin-Elmer Life & Analytical Sciences). The ScanArray Express software V2.0 (Perkin-Elmer Life & Analytical Sciences) was used to quantify the intensity of each spot. The same analysis procedure was carried out for analyzing His6-scFv1-CT fusion protein.

Figure 6:
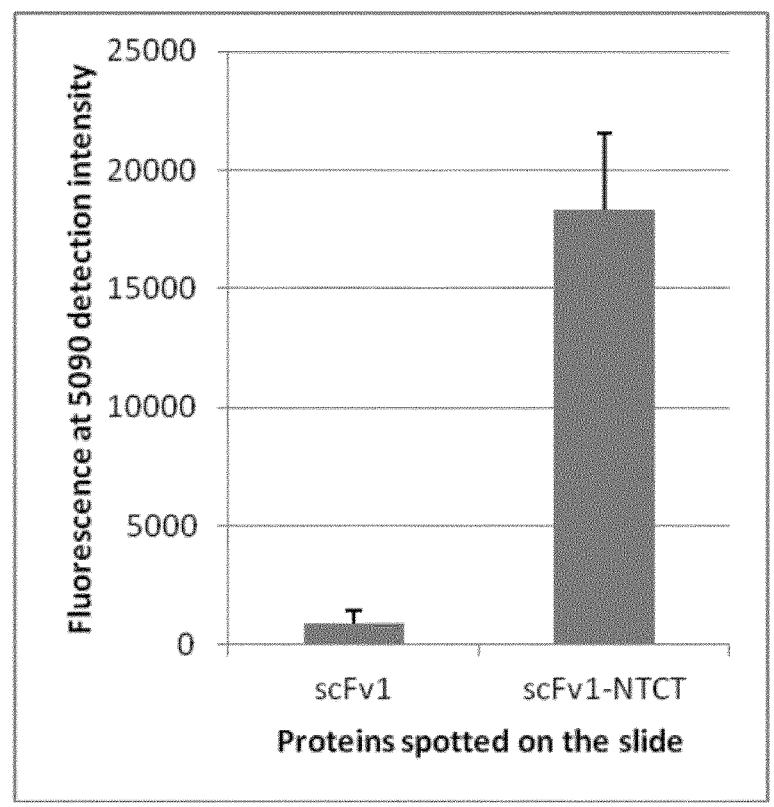
FIG. 6 shows an antigen binding analysis of pure and silk fused antibody fragments.

In order to detect the low abundant serum proteins which can be of potential biomarkers, scFv1 was fused to N-terminal of NTCT or CT giving rise to $His_6$-scFv1-NTCT and $His_6$-scFv1-CT, respectively. Pure antibody (control) and silk fused antibody fragments were spotted onto the microarray slide and their antigen binding capacity was analyzed using biotinylated antigen sample. Alexa-647-labeled streptavidin was then used to detect the bound antigens. FIG. 6 shows an antigen binding analysis of pure (control) and silk fused antibody fragments. Intensity of the spots was measured at 5090 detection intensity. The analysis showed that the antigen recognition of silk fused antibody ($His_6$-scFv1-NTCT) fragment was increased by 25 times compared to the scFv1 control alone, and no sign of cross reactivity with other antigens was observed for $His_6$-scFv1-NTCT.

The invention claimed is:

1. A recombinant fusion protein comprising the moieties B and CT, and optionally REP, wherein:
   B is comprising at least one immunoglobulin fragment, which provides the capacity of selective interaction with an organic target;
   CT is a moiety of from 70 to 120 amino acid residues and is derived from the C-terminal fragment of a spider silk protein, wherein the CT moiety has at least 50% identity to SEQ ID NO: 9 or at least 80% identity to SEQ ID NO: 7; and REP is a moiety of from 70 to 300 amino acid residues and is derived from the repetitive fragment of a spider silk protein wherein the REP moiety is selected from the group consisting of at least one of $L(AG)_nL$, $L(AG)_nAL$, $L(GA)_nL$, and $L(GA)_nGL$, wherein n is an integer from 2 to 10;

wherein each individual A segment is an amino acid sequence of from 8 to 18 amino acid residues, wherein from 0 to 3 of the amino acid residues are not Ala, and the remaining amino acid residues are Ala;

wherein each individual G segment is an amino acid sequence of from 12 to 30 amino acid residues, wherein at least 40% of the amino acid residues are Gly; and wherein each individual L segment is a linker amino acid sequence of from 0 to 20 amino acid residues.

2. The recombinant fusion protein according to claim 1, wherein each immunoglobulin fragment of the B moiety is selected from immunoglobulin variable regions.

3. The recombinant fusion protein according to claim 1, wherein the B moiety is comprising at least one heavy chain variable region ($V_H$) and at least one light chain variable region ($V_L$).

4. The recombinant fusion protein according to claim 1, wherein the B moiety is selected from the group consisting of single-chain variable fragments (scFv fragments), fragment antigen-binding (Fab fragments), F(ab')$_2$ fragments, domain antibodies (dAbs) and single domain antibodies (sdABs).

5. The recombinant fusion protein according to claim 4, wherein the B moiety is a single-chain variable fragment (scFv).

6. The recombinant fusion protein according to claim 1, wherein the B moiety contains 30-1000 amino acid residues, or 150-400 amino acid residues.

7. The recombinant fusion protein according to claim 1, selected from the group of proteins defined by the formulas $B_x$-CT-$B_z$, $B_x$-REP-$B_y$-CT-$B_z$ and $B_x$-CT-$B_y$-REP-$B_z$, wherein x, y and z are integers from 0 to 5; and x+y+z≥1.

8. The recombinant fusion protein according to claim 7, selected from the group of proteins defined by the formulas $B_x$-CT, CT-$B_z$, $B_x$-REP-CT, $B_x$-CT-REP, REP-CT-$B_z$ and CT-REP-$B_z$;

wherein x and z are integers from 1 to 5.

9. The recombinant fusion protein according to claim 8, selected from the group of proteins defined by the formulas B-CT, CT-B, B-REP-CT, B-CT-REP, REP-CT-B and CT-REP-B.

10. The recombinant fusion protein according to claim 1, selected from the group consisting of SEQ ID NOS: 61-70; and proteins having at least 80% identity to any of these sequences.

11. A protein structure capable of selective interaction with an organic target, wherein said protein structure is a polymer comprising as a repeating structural unit the recombinant fusion protein according to claim 1, wherein the B moiety provides the capacity of selective interaction with the organic target.

12. The protein structure according to claim 11, wherein said protein structure has a size of at least 0.1 μm in at least two dimensions.

13. The protein structure according to claim 11, wherein said protein structure is in a physical form selected from the group consisting of fiber, film, foam, net, mesh, sphere and capsule.

14. A method for separation of an organic target from a sample, comprising the steps of:

providing a sample containing the organic target;

providing an affinity medium for immobilization of and selective interaction with the organic target, said affinity medium comprising the fusion protein according to claim 1, wherein the B moiety is capable of selective interaction with the organic target;

contacting said affinity medium with said sample under suitable conditions to achieve binding between the affinity medium and the organic target; and removing non-bound sample.

15. The method according to claim 14, further comprising the step of contacting said affinity medium and the immobilized organic target with a second organic target, which is capable of selective interaction with the first organic target, under suitable conditions to achieve binding between the first and second organic targets.

16. A method for separation of an organic target from a sample, comprising the steps of:

providing a sample containing the organic target;

providing an affinity medium for immobilization of and selective interaction with the organic target, said affinity medium comprising a recombinant fusion protein comprising the moieties B and CT, and optionally REP, wherein:

B is comprising at least one immunoglobulin fragment, which provides the capacity of selective interaction with an organic target;

CT is a moiety of from 70 to 120 amino acid residues and is derived from the C-terminal fragment of a spider silk protein, wherein the CT moiety has at least 50% identity to SEQ ID NO: 9 or at least 80% identity to SEQ ID NO: 7; and REP is a moiety of from 70 to 300 amino acid residues and is derived from the repetitive fragment of a spider silk protein, wherein the B moiety is capable of selective interaction with the organic target, wherein the REP moiety is selected from the group consisting of at least one of $L(AG)_nL$, $L(AG)_nAL$, $L(GA)_nL$, and $L(GA)_nGL$, wherein n is an integer from 2 to 10;

wherein each individual A segment is an amino acid sequence of from 8 to 18 amino acid residues, wherein from 0 to 3 of the amino acid residues are not Ala, and the remaining amino acid residues are Ala;

wherein each individual G segment is an amino acid sequence of from 12 to 30 amino acid residues, wherein at least 40% of the amino acid residues are Gly; and wherein each individual L segment is a linker amino acid sequence of from 0 to 20 amino acid residues;

contacting said affinity medium with said sample under suitable conditions to achieve binding between the affinity medium and the organic target; and removing non-bound sample, wherein the fusion protein in the affinity medium is present as the protein structure according to claim 11 when contacting said affinity medium with said sample to achieve binding between the affinity medium and the organic target.

17. A method for separation of an organic target from a sample, comprising the steps of:

providing a sample containing the organic target;

providing an affinity medium for immobilization of and selective interaction with the organic target, said affinity medium comprising a recombinant fusion protein comprising the moieties B and CT, and optionally REP, wherein:

B is comprising at least one immunoglobulin fragment, which provides the capacity of selective interaction with an organic target;

CT is a moiety of from 70 to 120 amino acid residues and is derived from the C-terminal fragment of a spider silk protein, wherein the CT moiety has at least 50% identity to SEQ ID NO: 9 or at least 80% identity to SEQ ID NO: 7; and REP is a moiety of from 70 to 300 amino acid residues and is derived from the repetitive fragment of a spider silk protein, wherein the B moiety is capable of selective interaction with the organic target, wherein the REP moiety is selected from the group consisting of at least one of $L(AG)_nL$, $L(AG)_nAL$, $L(GA)_nL$, and $L(GA)_nGL$, wherein n is an integer from 2 to 10;

wherein each individual A segment is an amino acid sequence of from 8 to 18 amino acid residues, wherein from 0 to 3 of the amino acid residues are not Ala, and the remaining amino acid residues are Ala;

wherein each individual G segment is an amino acid sequence of from 12 to 30 amino acid residues, wherein at least 40% of the amino acid residues are Gly; and wherein each individual L segment is a linker amino acid sequence of from 0 to 20 amino acid residues;

contacting said affinity medium with said sample under suitable conditions to achieve binding between the affinity medium and the organic target; and removing non-bound sample, wherein the fusion protein in the affinity medium is present in solution when contacting said affinity medium with said sample to achieve binding between the affinity medium and the organic target, and wherein the complex of fusion protein bound to the organic target is allowed to form the protein structure according to claim 11.

18. The method according to claim 14, further comprising the step of detecting, and optionally quantifying, the presence of the immobilized target on said affinity medium.

19. The method according to claim 14, further comprising the step of releasing and collecting the organic target from the affinity medium.

20. The method according to claim 14, further comprising the final step of regenerating the affinity medium by chemical treatment and/or sterilizing heat treatment.

21. The method according to claim 20, wherein the chemical treatment comprises treatment with NaOH and/or urea.

* * * * *